US009382231B2

(12) United States Patent
Li et al.

(10) Patent No.: US 9,382,231 B2
(45) Date of Patent: Jul. 5, 2016

(54) BIPYRAZOLE DERIVATIVES AS JAK INHIBITORS

(71) Applicant: Incyte Corporation, Wilmington, DE (US)

(72) Inventors: Yun-Long Li, Chadds Ford, PA (US); Jincong Zhuo, Garnet Valley, PA (US); Ding-Quan Qian, Newark, DE (US); Song Mei, Wilmington, DE (US)

(73) Assignee: Incyte Corporation, Wilmington, DE (US)

(*) Notice: Subject to any disclaimer, the term of this patent is extended or adjusted under 35 U.S.C. 154(b) by 71 days.

(21) Appl. No.: 14/279,929

(22) Filed: May 16, 2014

(65) Prior Publication Data

US 2014/0343030 A1 Nov. 20, 2014

Related U.S. Application Data

(60) Provisional application No. 61/824,683, filed on May 17, 2013.

(51) Int. Cl.
*C07D 403/14* (2006.01)

(52) U.S. Cl.
CPC .................................... *C07D 403/14* (2013.01)

(58) Field of Classification Search
None
See application file for complete search history.

(56) References Cited

U.S. PATENT DOCUMENTS

| | | | |
|---|---|---|---|
| 7,598,257 B2 | 10/2009 | Rodgers et al. | |
| 7,834,022 B2 | 11/2010 | Rodgers et al. | |
| 8,410,265 B2 | 4/2013 | Zhou et al. | |
| 8,415,362 B2 | 4/2013 | Rodgers et al. | |
| 8,486,902 B2 | 7/2013 | Rodgers et al. | |
| 8,604,043 B2 | 12/2013 | Li et al. | |
| 8,691,807 B2 | 4/2014 | Yao et al. | |
| 8,716,303 B2 | 5/2014 | Rodgers et al. | |
| 8,765,734 B2 | 7/2014 | Huang et al. | |
| 8,933,085 B2 | 1/2015 | Rodgers et al. | |
| 8,987,443 B2 | 3/2015 | Liu et al. | |
| 9,034,884 B2 | 5/2015 | Rodgers et al. | |
| 9,181,271 B2 | 11/2015 | Li et al. | |
| 9,193,733 B2 | 11/2015 | Rodgers et al. | |
| 2008/0312259 A1 | 12/2008 | Rodgers et al. | |
| 2009/0233903 A1 | 9/2009 | Rodgers et al. | |
| 2010/0113416 A1 | 5/2010 | Friedman et al. | |
| 2011/0059951 A1 | 3/2011 | Rodgers et al. | |
| 2011/0288107 A1 | 11/2011 | Parikh et al. | |
| 2013/0045963 A1 | 2/2013 | Rodgers et al. | |
| 2013/0060026 A1 | 3/2013 | Zhou et al. | |
| 2014/0005166 A1 * | 1/2014 | Rodgers ............... | C07D 487/04 514/210.21 |
| 2014/0135350 A1 | 5/2014 | Ni et al. | |
| 2015/0065484 A1 | 3/2015 | Yeleswara et al. | |
| 2015/0087662 A1 | 3/2015 | Li et al. | |
| 2015/0246046 A1 | 9/2015 | Vaddi | |
| 2015/0342952 A1 | 12/2015 | Leopold et al. | |
| 2015/0344497 A1 | 12/2015 | Zhou et al. | |

FOREIGN PATENT DOCUMENTS

| | | |
|---|---|---|
| WO | WO 00/09495 | 2/2000 |
| WO | WO 00/53595 | 9/2000 |
| WO | WO 01/14402 | 3/2001 |
| WO | WO 01/64655 | 9/2001 |
| WO | WO 02/00196 | 1/2002 |
| WO | WO 03/024967 | 3/2003 |
| WO | WO 03/037347 | 5/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | WO 2012/177606 | 12/2012 |

OTHER PUBLICATIONS

Barabino et al., "Tear film and ocular surface tests in animal models of dry eye: uses and limitations," Experimental Eye Research, 2004, 79: 613-621.

Beck et al., "Brief Report: Alleviation of Systemic Manifestations of Castleman's Disease by Monoclonal Anti-Interleukin-6 Antibody," N. Engl. J. Med., 1994, 330(9): 602-605.

Bennett et al., "Proposals for the classification of the myelodysplastic syndromes," British Journal of Haematology, 1982, 51: 189-199.

Berge et al., "Pharmaceutical Salts," J. Pharma. Science, 1977, 66(1): 1-19.

Bhattacharya et al., "Brittain, ed. Polymorphism in Pharmaceutical Solids," 2009, p. 327-345.

Bioreversible Carriers in Drug Design, ed. Edward B. Roche, American Pharmaceutical Association and Pergamon Press, 1987* too voluminous to provide.

(Continued)

*Primary Examiner* — Kamal Saeed
(74) *Attorney, Agent, or Firm* — Fish & Richardson P.C.

(57) ABSTRACT

The present invention provides compounds of Formula I:

I

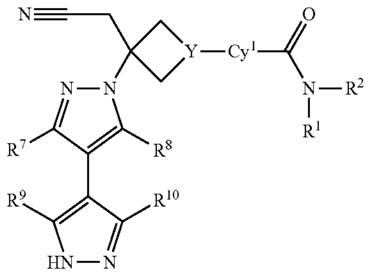

or pharmaceutically acceptable salts thereof, as well as their compositions and methods of use, that inhibit the activity of Janus kinase (JAK) and are useful in the treatment of diseases related to the activity of JAK including, for example, inflammatory disorders, autoimmune disorders, cancer, and other diseases.

30 Claims, 16 Drawing Sheets

(56) References Cited

OTHER PUBLICATIONS

Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chormatography—Mass Spectrometry," J. Comb. Chem., 2002, 4: 295-301.
Bock et al. "Managing drug resistance in cancer: lessons from HIV therapy." Nature, Jul. 2012, vol. 12, pp. 494-501.
Bolen, "Nonreceptor tyrosine protein kinases", Oncogene, 1993, 8(8):2025-31.
Bollrath et al., "130-Meidated Stat3 Activation in Enterocytes Regulates Cell Survival and Cell-Cycle Progression during Colitis-Associated Tumorigenesis," Cancer Cell, 15: 91-102 (2009).
Bori et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.
Bosworth, "JAK1/JAK2 Inhibitor Ruxolitinib Is a Rising Start," Clinical Oncology, Apr. 2011, 06:04, 3 pages.
Boudny, et al., "JAK/STAT signaling pathways and cancer", Neoplasm, 49:349-355, 2002.
Bowman, et al. "STATs in oncogenesis", Oncogene, 19:2474-2488, 2000.
Bromberg et al., "Inflammation and Cancer: IL-6 and STA T3 Complete the Link," Cancer Cell, 15:79-80 (2009).
Bunning and Germing, "Myelodysplastic syndromes/neoplasms" in Chapter 5, Swerdlow, et al, eds. WHO Classification of Tumours of Haematopoietic and Lymphoid Tissues. (ed. 4th edition): Lyon, France: IARC Press;2008:88-103.
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger, et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immunodeficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia*, 2013, 13(33):333-337.
Chen et al., "Blockade of interleukin-6 signaling augments regulatory T-cell reconstitution and attenuates the severity of graft-versusl-host disease," Blood, Jul. 2009, 114(4): 891-900.
Chen et al., "Induction of myelodysplasia by myeloid-derived suppressor cells," J Clin Invest, Nov. 2013, 123(11): 4595-611.
Chen, et al., "Stat3 Activation in Human Endometrial and Cervical Cancer", British Journal of Cancer, 96, 591-599, 2007.
Cheson et al., "Report of an international working group to standardize response criteria for myelodysplastic syndromes," Blood, Dec. 2000, 96(12): 3671-4.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Cilloni et al., "Emerging drugs for chronic myeloid leukemia", Expert Opinion on Emerging Drugs, (Jun. 2010) vol. 15, No. 2, pp. 175-184.
Claessens et al., "In vitro proliferation and differentitation of erythyroid progenitors from patients with myelodysplastic syndromes: evidence for Fas-dependent apoptosis," Blood, Mar. 2012, 1594-1601.
Clark et al., "Discovery and Development of Janus Kinase (JAK) inhibitors for Inflammatory Diseases," J Med Chem., 2014, pp. A-P.
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Coligan, J.E. et al, Wiley Press; Methods in Molecular Biology: vol. 225, Inflammation Protocols., Winyard, P.G. and Willoughby, D.A., Humana Press (2003)* too voluminous to provide.
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deuse, T. et al., "Novel Immunosuppression: R348, a JAK3- and Syk-Inhibitor Attenuates Acute Cardiac Allograft Rejection", Transplantation, 2008, 85(6) 885-892.
Dudley et al., "A VEGF/JAK2/STAT5 axis may partially mediate endothelial cell tolerance to hypoxia," Biochem J, Sep. 2005, 390(Pt 2): 427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonseca et al., "Interleukin-6 as a key player in systemic inflammation and joint destruction," Autoimmun Rev, Jun. 2009, 8(7): 538-42.
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).

(56) References Cited

OTHER PUBLICATIONS

Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Gaestel et al., "Targeting innate immunity protein kinase signalling in inflammation," Nat Rev Drug Discov., Jun. 2009, 8(6):480-99.
Goodman, et al., "IL-6 Signaling in Psoriasis Prevents Immune Suppression by Regulatory T Cells," J. Immunol., Sep. 2009, 183: 3170-3176.
Gorre, M.E. et al., "Clinical Resistance to STI-571 Cancer Therapy Caused by BCR-ABL Gene Mutation or Amplification." Science, 293:876, 2001.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic—contact hypersensitivity", Immunol Today, Jan. 19(1):37-44 (1998) (only 1 page provide and marked "best available copy").
Greenberg, "The myelodysplastic syndromes" in Hoffman, et al, eds. Hematology: Basic Principles and Practice (3rd ed.), Churchill Livingston; 2000:1106-1129.
Greene, Protective Groups in Organic Synthesis, 4th ed., John Wiley & Sons: New Jersey, (2007).
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, Nov. 2003, 58(11): 1101-13.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guschin, et al, "A major role for the protein tyrosine kinase JAK1 in the JAKISTAT signal transduction pathway in response to interleukin-6", Embo J 14:1421-1429 (1995).
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "World Health Organization classification of neoplastic diseases of the hematopoietic and lymphoid tissues: report of the Clinical Advisory Committee meeting-Airlie House, Virginia, Nov. 1997," J Clin Oncol, Dec. 1999, 17(12): 3835-49.
Huang, "Inhibition of STAT3 activity with AG490 decreases the invasion of human pancreatic cancer cells in vitro", Cancer Sci. 97(12):1417-23 (2006).
Hyung-Bae et al., *Transplantation*, 2010, 90(8):825-835.
International Search Report and Written Opinion in International Application No. PCT/US2014/038388, dated Sep. 1, 2014, 9 pages.
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (−)-CP55,940", Organic Letters, 2005; 7(19); 4181-4183.
Jädersten et al., "Long-term outcome of treatment of anemia in MDS with erythropoietin and G-CSF," Blood, Aug. 2005, 106(3): 803-11.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron, Interact., 1(3):193-207 (2001).
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).
Kantarjian et al., "Decitabine improves patient outcomes in myelodysplastic syndromes: results of phase III randomized study," Cancer, Apr. 2006, 106(8): 1794-803.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase. Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Dec. 2006, 86(12): 1243-1260.
Kiss, Robert, "Recent developments on JAK2 inhibitors: A patent review", Expert Opinion on Therapeutic Patents, (Apr. 2010) vol. 20, No. 4, pp. 471-495.
Kola, Nature Reviews Drug Discovery 3, pp. 711-715 (2004).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai, et al., "Mechanistic Study on the Inactivation of General Acyl-CoA Dehydrogenase by a Metabolite of Hypoglycin A", J. Am. Chem. Soc. 113: 7388-7397 (1991).
Larson, "Myelodysplasia: when to treat and how," Best Pract Res Clin Haematol, 2006, 19(2): 293-300.
Lemp, "The Definition and Classification of Dry Eye Disease: Report of the Definition and Classification Subcommittee of the International Eye Workshop," The Ocular Surface, 5(2): 75-92.
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 a Selective Janus Kinase 1/2 Inhibitor" Presentation at the 50th American Society of Hematology Annual Meeting (ASH), Dec. 8, 2008.

(56) References Cited

OTHER PUBLICATIONS

Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
List et al., "Efficacy of lenalidomide in myelodysplastic syndromes," N Engl J Med, Feb. 2005, 352(6): 549-57.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert, et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCOD)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Maxson et al., "Oncogenic *CSF3R* Mutations in Chronic Neutrophilic Leukemia and Atypical CML," *N. Engl. J. Med*., 2013, 368(19):1781-1790.
McMillan, "The systemic inflammation-based Glasgow Prognostic Score: a decade of experience in patients with cancer," Cancer Treat Rev, Aug. 2013, 39(5): 534-40.
Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Meydan et al., "Inhibition of acute lymphoblastic leukaemia by a Jak-2 inhibitor", Nature. Feb. 15, 1996;379(6566):645-8.
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.
Miyoshi et al., "Interleukin-8 concentrations in conjunctival epithelium brush cytology samples correlate with neutrophil, eosinophil infiltration, and corneal damage", Cornea, 2001;20:743-7.
Molldrem, et al., "Antithymocyte globulin for patients with myelodysplastic syndrome," Br J Haematol, Dec. 1997, 99(3): 699-705.
Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Mullighan, et al, "JAK mutations in high-risk childhood acute lymphoblastic leukemia", Proc Natl Acad Sci USA. 106:9414-8 (2009).
Mundle, et al. Am J Hematol 1999;60:36-47.
Naka T., "The paradigm of IL-6: from basic science to medicine", Arthritis Res., 2002;4 Suppl 3:S233-42.
Nakagawara, Akira, "Trk receptor tyrosine kinases. A bridge between cancer and neural development." Cancer Letters, 169:107-114, 2001.
Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Neidle, Stephen, Cancer Drug Design and Discovery, (Elsevier/Academic Press, 2008) pp. 427-431.
Neubauer, H., et al., "Jak2 Deficiency Defines an Essential Developmental Checkpoint in Definitive Hematopoiesis", Cell, 93(3): 397-409 (1998).
Neuner, et al., J. Invest. Dermatol. 1991, 97, 27-33.
Nicholoff et al., "Recent Insights into the immunopathogenesis of psoriasis provide new therapeutic opportunities", J. Clin. Invest., 113; 1664-1675 (2004).
Nishimoto et. al., "Improvement in Castleman's disease by humanized anti-interleukin-6 receptor antibody theraphy," *Blood*, 2000, 95(1):56-61.
Norman, "Selective JAK1 inhibitor and selective Tyk2 inhibitor patents," *Expert Opinion,*Informa Healthcare. 2012, available at: <http://informahealthcare.com/dol/pdfplus/10.1517/13543776.2012.723693>.
Ortmann, et al., "Janus kinases and signal transducers and activators of transcription: their roles in cytokine signaling, development and immunoregulation " Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.

(56) References Cited

OTHER PUBLICATIONS

Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Pedranzini, et al., Cancer Res., 66(19):9714-9721 (2006).
Pernis, et al., "JAK-STAT signaling in asthma" J Clin Invest, 109(10): 1279-83 (2002).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Raza et al., "Novel insights into the biology of myelodysplastic syndromes: excessive apoptosis and the role of cytokines," Int J Hematol, Jun. 1996, 63(4): 265-78.
Raza et al., "The myelodysplastic syndromes in 1996: complex stem cell disorders confounded by dual actions of cytokines," Leuk Res, Nov.-Dec. 1996, 20(11-12): 881-90.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Remington's Pharmaceutical Sciences, 17th ed., Mack Publishing Company, Easton, Pa., 1985, p. 1418.
Roberts et al., "Trends in the risks and benefits to patients with cancer participating in phase 1 clinical trials," JAMA, Nov. 2004, 292(17): 2130-40.
Rodig, et al., "Disruption of the Jak1 gene demonstrates obligatory and nonredundant roles of the Jaks in cytokine-induced biologic responses." Cell, 93(3): 373-83 (1998).
Roudebush et al., "Pharmacologic manipulation of a four day murine delayed type hypersensitivity model," Agents Actions, Jan. 1993, 38(1-2): 116-21.
Rousvoal, G. et al. "Janus kinase 3 inhibition with Cp-690,550 prevents allograft vasculopathy", Transpl Int., 2006 19(12):1014-21.
Samanta et al., "Janus kinase 2: a critical target in chronic myelogenous leukemia", Cancer Res. Jul. 1, 2006;66(13):6468-72.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling", Adv Pharmacol. 2000; 47:113-74.
Schrader et al., "Animal models of dry eye," Dev Opthalmol, 2008, 41:298-312.
Scott, et al., "Jaks, STATs, Cytokines, and Sepsis." Clin Diagn Lab Immunol, 9(6): 1153-9 (2002).
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia" Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al., "Basic pathogenic mechanisms operating in experimental models of acute anteriior uveitis," Immunol Cell Biol, Dec. 1998, 76(6): 497-512.
Smolen, et al, "Effect of interleukin-6 receptor inhibition with tocilizumab in patients with rheumatoid arthritis (OPTION study): a double-blind, placebo-controlled, randomized trial", Lancet 371:987, 2008 (2008).
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, Jun. 2014, 123(24): 3832-42.
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Symington et al., "The relationship of serum IL-6 levels to acute graft-versus-host disease and hepatorenal disease after human bone marrow transplantation," Transplantation, Sep. 1992, 54(3): 457-62.
Takemoto, et al. (1997). "Proliferation of adult T cell leukemia/lymphoma cells is associated with the constitutive activation of JAK/STAT proteins." Proc Natl Acad Sci U S A, 94(25): 1387-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Toyonaga, "Blockade of constitutively activated Janus kinase/signal transducer and activator of transcription-3 pathway inhibits growth of human pancreatic cancer", Cancer Lett. 201(1):107-16 (2003).

(56) References Cited

OTHER PUBLICATIONS

Trikha et al., "Targeted anti-interleukin-6 monoclonal antibody therapy for cancer: a review of the rationale and clinical evidence," Clinical Cancer Research, 2003, 9: 4653-4665.
Vanhoutte, Arthritis Rheum 64.10 (2012): S1051-1.
Vannucchi A. et al., "The mTOR Inhibitor, RAD001, Inhibits the Growth of Cells From Patients with Myeloproliferative Neoplasms", Blood: ASH Annual Meeting Absracts, 51$^{st}$ Annual Meeting of the American Society of Hematology, vol. 114, No. 22 (2009) 2 pages.
Vannucchi, A. et al, "Inhibitorsof PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vardiman et al., "The 2008 revision of the World Health Organization (WHO) classification of myeloid neoplasms and acute leukemia: rationale and important changes," Blood, Jul. 2009, 114(5): 937-51.
Vardiman et al., "The World Health Organization (WHO) classification of the myeloid neoplasms," Blood, Oct. 2002, 100(7): 2292-302.
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).
Wagh et al., "Polymers used in ocular dosage form and drug delivery systems," Asian J. Pharma, 12-17.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Xiaoyang et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Yongjun et al., "Advances in research of tyrosine kinases inhibitor of vascular endothelial growth factor receptor," Chinese J New Drugs, Dec. 31, 2008, 17(7):544-550.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," Journal of Clinical Oncology, Nov. 2012, 30(33): 4161-4167.
Yu, et al., "Constitutive activation of the Janus kinase-STAT pathway in T lymphoma overexpressing the Lck protein tyrosine kinase" J Immunol. 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zou, et al., "Signaling Pathways Activated by Oncogenic Forms of Abl Tyrosine Kinase." Journal of Biological Chemistry, 274(26):18141-18144, 1999.

* cited by examiner

BIPYRAZOLE DERIVATIVES AS JAK INHIBITORS

This application claims the benefit of priority of U.S. Provisional Appl. No. 61/824,683, filed May 17, 2013, which is incorporated herein by reference in its entirety.

TECHNICAL FIELD

The present invention provides bipyrazole derivatives, as well as their compositions and methods of use, that modulate the activity of Janus kinase (JAK) and are useful in the treatment of diseases related to the activity of JAK including, for example, inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides, inter alia, compounds of Formula I:

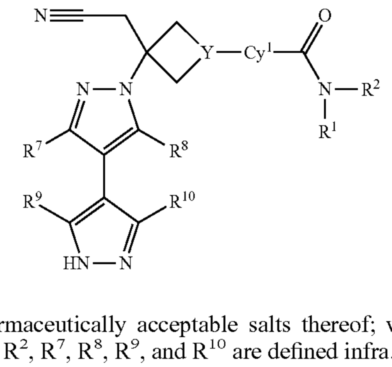

I and pharmaceutically acceptable salts thereof; wherein Y, $Cy^1$, $R^1$, $R^2$, $R^7$, $R^8$, $R^9$, and $R^{10}$ are defined infra.

The present invention further provides compositions comprising a compound of Formula I, or a pharmaceutically acceptable salt thereof, and a pharmaceutically acceptable carrier.

The present invention further provides methods of modulating an activity of JAK1 comprising contacting JAK1 with a compound of Formula I, or a pharmaceutically acceptable salt thereof.

The present invention further provides methods of treating a disease or a disorder associated with abnormal kinase expression or activity in a patient by administering to a patient a therapeutically effective amount of a compound of Formula I, or a pharmaceutically acceptable salt thereof.

The present invention further provides methods of treating an autoimmune disease, a cancer, a myeloproliferative disorder, a myelodysplastic syndrome (MDS), an inflammatory disease, a bone resorption disease, or organ transplant rejection in a patient in need thereof, comprising administering to said patient a therapeutically effective amount of a compound of Formula I, or a pharmaceutically acceptable salt thereof.

The present invention also provides compounds of Formula I, or pharmaceutically acceptable salts thereof, as described herein for use in treatment of autoimmune diseases, cancer, myeloproliferative disorders, myelodysplastic syndromes (MDS), inflammatory diseases, a bone resorption disease, or organ transplant rejection.

The present invention further provides compounds of Formula I as described herein, or pharmaceutically acceptable salts thereof, for use in modulating JAK1.

The present invention also provides uses of compounds of Formula I as described herein, or pharmaceutically acceptable salts thereof, for the preparation of medicaments for use in methods of modulating JAK1.

DETAILED DESCRIPTION

Figure 1:
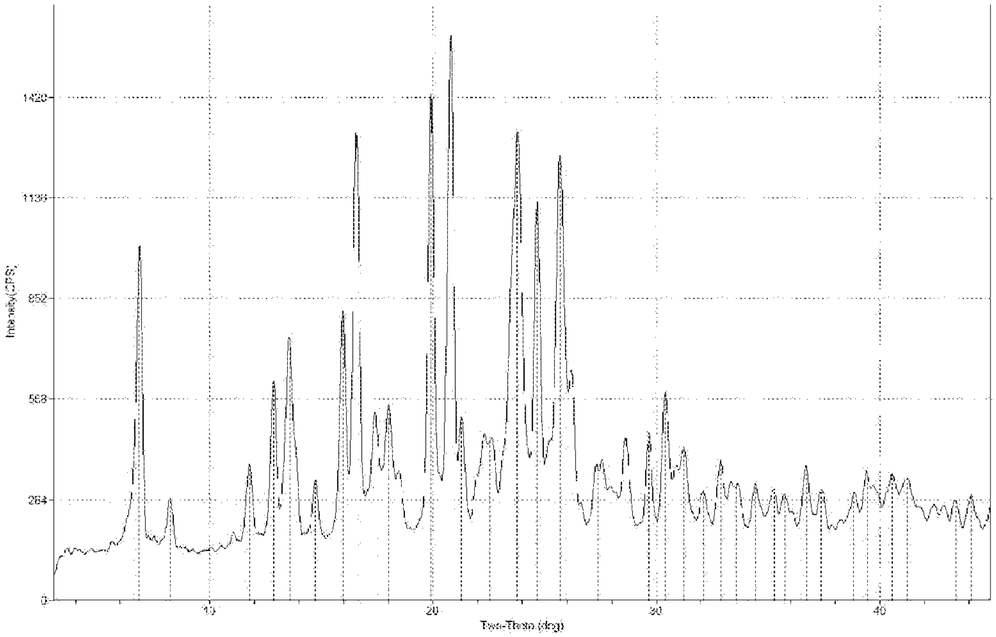
FIG. 1 shows an XRPD pattern characteristic of the salt of Example 14.

The present invention provides, inter alia, a compound of Formula I:

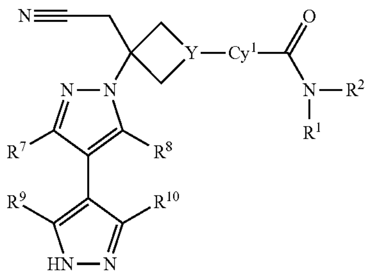

I or a pharmaceutically acceptable salts thereof; wherein:

$Cy^1$ is phenyl, pyridyl, pyrimidinyl, pyrazinyl, or pyridazinyl, each of which is optionally substituted by 1, 2, 3, or 4 groups independently selected from $R^3$, $R^4$, $R^5$, and $R^6$;

Y is N or CH;

$R^1$ is $C_{1-6}$ alkyl, $C_{1-6}$ haloalkyl, $C_{3-7}$ cycloalkyl, $C_{3-7}$ cycloalkyl-$C_{1-3}$ alkyl, 4-7 membered heterocycloalkyl, 4-7 membered heterocycloalkyl-$C_{1-3}$ alkyl, phenyl, phenyl-$C_{1-3}$ alkyl, 5-6 membered heteroaryl or 5-6 membered heteroaryl-$C_{1-3}$ alkyl, each of which is optionally substituted with 1, 2, or 3 substituents independently selected from fluoro, chloro, $C_{1-3}$ alkyl, —OH, —O($C_{1-3}$ alkyl), —CN, —$CF_3$, —$CHF_2$, —$CH_2F$, —$NH_2$, —NH($C_{1-3}$ alkyl), —N($C_{1-3}$ alkyl)$_2$, —C(═O)N($C_{1-3}$ alkyl)$_2$, —C(═O)NH($C_{1-3}$ alkyl), —C(═O)$NH_2$, —C(═O)O($C_{1-3}$ alkyl), —S(═O)$_2$($C_{1-3}$ alkyl), —S(═O)$_2$($C_{3-6}$ cycloalkyl), —C(═O)($C_{3-6}$ cycloalkyl), and —C(═O)($C_{1-3}$ alkyl);

$R^2$ is H or $C_{1-3}$ alkyl; wherein said $C_{1-3}$ alkyl is optionally substituted by 1, 2, or 3 substituents independently selected from fluoro, chloro, —OH, —O($C_{1-3}$ alkyl), —CN, —$CF_3$, —$CHF_2$, —$CH_2F$, $NH_2$, —NH($C_{1-3}$ alkyl), and —N($C_{1-3}$ alkyl)$_2$; or $R^1$ and $R^2$, together with the nitrogen atom to which they are attached, form a 4-, 5- or 6-membered heterocycloalkyl ring, which is optionally substituted with 1, 2, or 3 substitutents independently selected from F, Cl, —OH, —O($C_{1-3}$ alkyl), —CN, $C_{1-3}$ alkyl, $C_{1-3}$ haloalkyl, —$NH_2$, —NH($C_{1-3}$ alkyl), —N($C_{1-3}$ alkyl)$_2$, —$CH_2CN$, and —$CH_2OH$;

$R^3$ is H, F, Cl, —CN, $C_{1-3}$ alkyl, $C_{1-3}$ fluoroalkyl, —O($C_{1-3}$ alkyl), or —O($C_{1-3}$ fluoroalkyl);

$R^4$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^5$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^6$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^7$ is H, F, Cl, $C_{1-3}$ alkyl, $C_{1-3}$ haloalkyl, —$NR^{17}R^{17a}$, —NHC(═O)$R^{17b}$, —C(═O)$NR^{17a}R^{17b}$, —NHS(═O)$_2$ $R^{17b}$, or —S(═O)$_2NR^{17a}R^{17b}$, wherein said $C_{1-3}$ alkyl is optionally substituted with 1, 2, or 3 substituents selected from F, Cl, —CN, —$CF_3$, —$CHF_2$, —$CH_2F$, —$NH_2$, —NH($CH_3$), —N($CH_3$)$_2$, OH, —$OCH_3$, and —$OCF_3$, —$OCHF_2$, and —$OCH_2F$;

$R^8$ is H, F, Cl, $C_{1-3}$ alkyl, or $C_{1-3}$ haloalkyl;

$R^9$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{10}$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{17}$ is $C_{1-6}$ alkyl, phenyl or 5-6 membered heteroaryl, each of which is optionally substituted with 1, 2, 3 or 4 independently selected $R^{27}$ substituents;

$R^{17a}$ is H or $C_{1-3}$ alkyl;

$R^{17b}$ is $C_{1-3}$ alkyl optionally substituted with 1, 2, or 3 substituents selected from F, chloro, —CN, —$CF_3$, —$CHF_2$, —$CH_2F$, —$NH_2$, —$NH(CH_3)$, —$N(CH_3)_2$, OH, —$OCH_3$, and —$OCF_3$, —$OCHF_2$, and —$OCH_2F$; and each $R^{27}$ is independently selected from halo, —OH, $NO_2$, —CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $CF_3$—$C_{1-3}$ hydroxyalkyl, $C_{1-3}$ alkoxy-$C_{1-3}$ alkyl, $C_{3-7}$ cycloalkyl, $C_{1-3}$ alkoxy, $C_{1-3}$ haloalkoxy, $H_2N$—, ($C_{1-3}$ alkyl)NH—, $(C_{1-3}$ alkyl$)_2$N—, HS—, $C_{1-3}$ alkyl-S—, $C_{1-3}$ alkyl-S(=O)—, $C_{1-3}$ alkyl-S(=O$)_2$—, carbamyl, $C_{1-3}$ alkylcarbamyl, di($C_{1-3}$ alkyl)carbamyl, carboxy, $C_{1-3}$ alkyl-C(=O)—, $C_{1-4}$ alkoxy-C(=O)—, $C_{1-3}$ alkyl-C(=O)O—, $C_{1-3}$ alkyl-C(=O)NH—, $C_{1-3}$ alkyl-S(=O$)_2$NH—, $H_2N$—$SO_2$—, $C_{1-3}$ alkyl-NH—S(=O$)_2$—, $(C_{1-3}$ alkyl$)_2$N—S(=O$)_2$—, $H_2N$—S(=O$)_2$NH—, $C_{1-3}$ alkyl-NHS(=O$)_2$NH—, $(C_{1-3}$ alkyl$)_2$N—S(=O$)_2$NH—, $H_2N$—C(=O)NH—, $C_{1-3}$ alkyl-NHC(=O)NH—, and $(C_{1-3}$ alkyl$)_2$N—C(=O)NH—.

In some embodiments, the compound is a compound of Formula Ia:

Ia

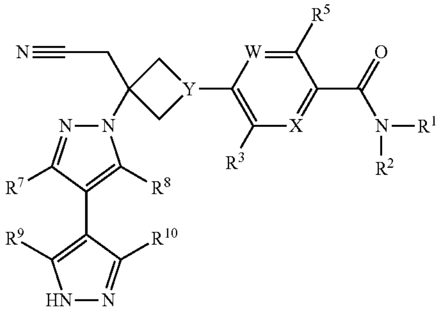

or a pharmaceutically acceptable salt thereof.

In some embodiments, the compound is a compound of Formula Ia:

Ia

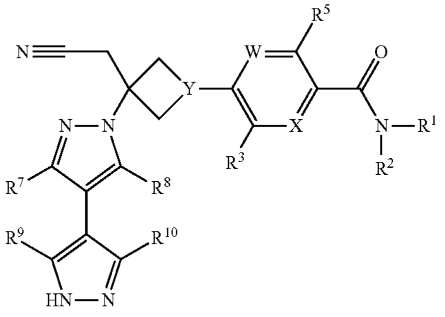

or a pharmaceutically acceptable salt thereof; wherein:

X is N or $CR^4$;

W is N or $CR^6$;

Y is N or CH;

$R^1$ is $C_{1-6}$ alkyl, $C_{1-6}$ haloalkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl, each of which is optionally substituted with 1, 2, or 3 substituents independently selected from fluoro, chloro, $C_{1-3}$ alkyl, —OH, —O($C_{1-3}$ alkyl), —CN, —$CF_3$, —$CHF_2$, —$CH_2F$, —$NH_2$, —NH($C_{1-3}$ alkyl), —N($C_{1-3}$ alkyl$)_2$, —C(=O)N($C_{1-3}$ alkyl$)_2$, —C(=O)NH($C_{1-3}$ alkyl), —C(=O)$NH_2$, —C(=O)O($C_{1-3}$ alkyl), —S(=O$)_2$($C_{1-3}$ alkyl), —S(=O$)_2$($C_{3-6}$ cycloalkyl), —C(=O)($C_{3-6}$ cycloalkyl), and —C(=O)($C_{1-3}$ alkyl);

$R^2$ is H or $C_{1-3}$ alkyl; wherein said $C_{1-3}$ alkyl is optionally substituted by 1, 2, or 3 substituents independently selected from fluoro, chloro, —OH, —O($C_{1-3}$ alkyl), —CN, —$CF_3$, —$CHF_2$, —$CH_2F$, $NH_2$, —NH($C_{1-3}$ alkyl), and —N($C_{1-3}$ alkyl$)_2$; or $R^1$ and $R^2$, together with the nitrogen atom to which they are attached, form a 4-, 5- or 6-membered heterocycloalkyl ring, which is optionally substituted with 1, 2, or 3 substitutents independently selected from fluoro, —OH, —O($C_{1-3}$ alkyl), —CN, $C_{1-3}$ alkyl, $C_{1-3}$ haloalkyl, —$NH_2$, —NH($C_{1-3}$ alkyl), —N($C_{1-3}$ alkyl$)_2$, and —$CH_2CN$;

$R^3$ is H, F, Cl, —CN, $C_{1-3}$ alkyl, —$OCF_3$, —$CF_3$, or —O($C_{1-3}$ alkyl);

$R^4$ is H, F, Cl, —CN, $C_{1-3}$ alkyl, or —O($C_{1-3}$ alkyl);

$R^5$ is H, F, Cl, —CN, $C_{1-3}$ alkyl, or —O($C_{1-3}$ alkyl);

$R^6$ is H, F, Cl, —CN, or $C_{1-3}$ alkyl;

$R^7$ is H, F, Cl, $C_{1-3}$ alkyl, $C_{1-3}$ haloalkyl, —$NR^{17}R^{17a}$, —NHC(=O)$R^{17b}$, —C(=O)$NR^{17a}R^{17b}$, —NHS(=O$)_2$$R^{17b}$, or —S(=O$)_2$$NR^{17a}R^{17b}$, wherein said $C_{1-3}$ alkyl is optionally substituted with 1, 2, or 3 substituents selected from F, Cl, —CN, —$CF_3$, —$CHF_2$, —$CH_2F$, —$NH_2$, and OH;

$R^8$ is H, F, Cl, $C_{1-3}$ alkyl, or $C_{1-3}$ haloalkyl;

$R^9$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl$)_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{10}$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl$)_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{17}$ is $C_{1-6}$ alkyl, phenyl or 5-6 membered heteroaryl, each of which is optionally substituted with 1, 2, 3 or 4 substituents independently selected from $R^{27}$;

$R^{17a}$ is H or $C_{1-3}$ alkyl;

$R^{17b}$ is $C_{1-3}$ alkyl optionally substituted with 1, 2, or 3 substituents selected from F, chloro, —CN, —$CF_3$, —$CHF_2$, —$CH_2F$, —$NH_2$, and OH and each $R^{27}$ is independently selected from halo, —OH, $NO_2$, —CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $CF_3$—$C_{1-3}$ hydroxyalkyl, $C_{1-3}$ alkoxy-$C_{1-3}$ alkyl, $C_{3-7}$ cycloalkyl, $C_{1-3}$ alkoxy, $C_{1-3}$ haloalkoxy, $H_2N$—, ($C_{1-3}$ alkyl)NH—, $(C_{1-3}$ alkyl$)_2$N—, HS—, $C_{1-3}$ alkyl-S—, $C_{1-3}$ alkyl-S(=O)—, $C_{1-3}$ alkyl-S(=O$)_2$—, carbamyl, $C_{1-3}$ alkylcarbamoyl, di($C_{1-3}$ alkyl)carbamyl, carboxy, $C_{1-3}$ alkyl-C(=O)—, $C_{1-4}$ alkoxy-C(=O)—, $C_{1-3}$ alkyl-C(=O)O—, $C_{1-3}$ alkyl-C(=O)NH—, $C_{1-3}$ alkyl-S(=O$)_2$NH—, $H_2N$—$SO_2$—, $C_{1-3}$ alkyl-NH—S(=O$)_2$—, $(C_{1-3}$ alkyl$)_2$N—S(=O$)_2$—, $H_2N$—S(=O$)_2$NH—, $C_{1-3}$ alkyl-NHS(=O$)_2$NH—, $(C_{1-3}$ alkyl$)_2$N—S(=O$)_2$NH—, $H_2N$—C(=O)NH—, $C_{1-3}$ alkyl-NHC(=O)NH—, and $(C_{1-3}$ alkyl$)_2$N—C(=O)NH—.

In some embodiments:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^6$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, Y is N.

In some embodiments, Y is CH.

In some embodiments, X is N.

In some embodiments, X is $CR^4$.

In some embodiments, $R^4$ is H or F.

In some embodiments, $R^4$ is H.

In some embodiments, $R^4$ is F.

In some embodiments, W is N.

In some embodiments, W is $CR^6$.

In some embodiments, $R^6$ is H, F, or Cl.

In some embodiments, $R^6$ is H or F.

In some embodiments, $R^6$ is H.

In some embodiments, $R^6$ is F.

In some embodiments, $R^3$ is H or F.

In some embodiments, $R^5$ is H or F.

In some embodiments, $R^2$ is H or methyl.

In some embodiments, $R^2$ is H.

In some embodiments, $R^2$ is methyl.

In some embodiments, $R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl.

In some embodiments, $R^1$ is isopropyl, ethyl, 1-methylpropyl, 2,2,2-trifluoro-1-methylethyl, 1-cyclopropylethyl, cyclopropyl, 1-trifluoromethylcyclopropyl, 1-cyclopropyl-2,2,2-trifluoroethyl, 2,2,2-trifluoroethyl, or 2,2-difluoroethyl.

In some embodiments, $R^1$ is isopropyl, ethyl, 1-methylpropyl, or 2,2,2-trifluoro-1-methylethyl.

In some embodiments, $R^1$ is isopropyl

In some embodiments, $R^1$ is ethyl.

In some embodiments, $R^1$ is 1-methylpropyl.

In some embodiments, $R^1$ is 2,2,2-trifluoro-1-methylethyl.

In some embodiments, $R^7$ is H, methyl, ethyl, or HO—$CH_2$—.

In some embodiments, $R^7$ is H.

In some embodiments, $R^7$ is methyl.

In some embodiments, $R^8$ is H or methyl.

In some embodiments, $R^8$ is H.

In some embodiments, $R^9$ is H, methyl or ethyl.

In some embodiments, $R^9$ is H.

In some embodiments, $R^9$ is methyl.

In some embodiments, $R^{10}$ is H, methyl, ethyl, or HO—$CH_2$—.

In some embodiments, $R^{10}$ is H.

In some embodiments, $R^{10}$ is methyl.

In some embodiments, $R^{10}$ is ethyl.

In some embodiments, $R^{10}$ is HO—$CH_2$—.

In some embodiments, the compound is a compound of Formula II:

II

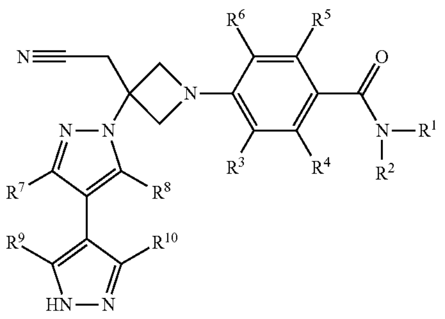

or a pharmaceutically acceptable salt thereof.

In some embodiments, the compound is a compound of Formula III:

III

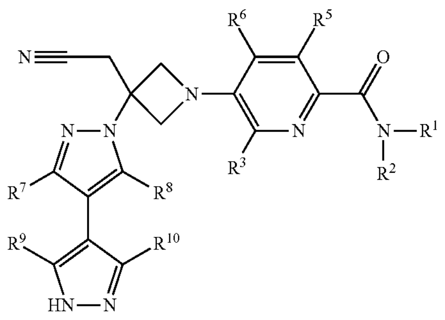

or a pharmaceutically acceptable salt thereof.

In some embodiments, the compound is a compound of Formula IV:

IV

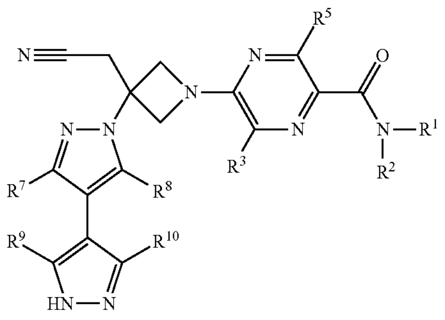

or a pharmaceutically acceptable salt thereof.

In some embodiments, the compound is a compound of Formula IIa:

IIa

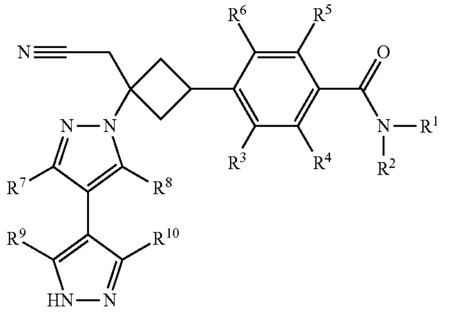

or a pharmaceutically acceptable salt thereof.

In some embodiments, the compound is a compound of Formula IIIa:

IIIa

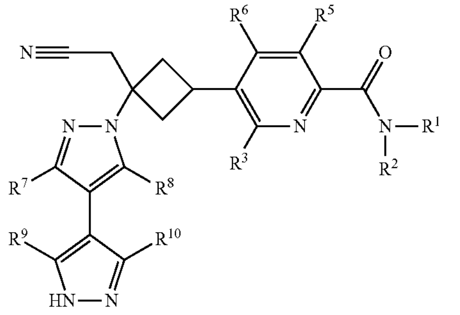

or a pharmaceutically acceptable salt thereof.

In some embodiments, the compound is a compound of Formula IVa:

IVa

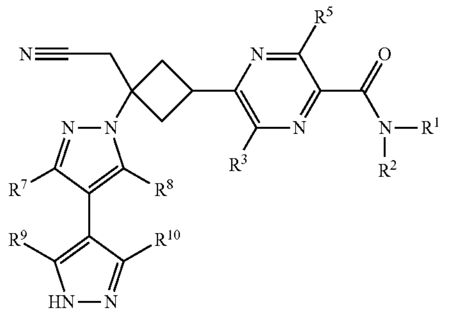

or a pharmaceutically acceptable salt thereof.

In some embodiments, the compound is a compound of Formula Ia, or a pharmaceutically acceptable salt thereof, wherein:

X is N or $CR^4$;

W is N or $CR^6$;

Y is N or CH;

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^6$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula II, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^6$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula III, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula IV, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^5$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula IIa, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^6$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula IIIa, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the compound is a compound of Formula IVa, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^5$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

In some embodiments, the present application provides 5-[3-(cyanomethyl)-3-(3'-methyl-1H,1'H-4,4'-bipyrazol-1-yl)azetidin-1-yl]-N-[(1S)-2,2,2-trifluoro-1-methylethyl]pyrazine-2-carboxamide, or a pharmaceutically acceptable salt thereof.

In some embodiments, the present application provides 5-[3-(cyanomethyl)-3-(3'-methyl-1H,1'H-4,4'-bipyrazol-1-yl)azetidin-1-yl]-N-isopropylpyrazine-2-carboxamide. or a pharmaceutically acceptable salt thereof.

In some embodiments, the present application provides 4-[3-(cyanomethyl)-3-(3'-methyl-1H,1'H-4,4'-bipyrazol-1-yl)azetidin-1-yl]-N-isopropylbenzamide, or a pharmaceutically acceptable salt thereof.

In some embodiments, the present application provides 4-[3-(cyanomethyl)-3-(3'-methyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the present application provides 4-[3-(1H,1'H-4,4'-bipyrazol-1-yl)-3-(cyanomethyl)azetidin-1-yl]-2,5-difluoro-N-[(1S)-2,2,2-trifluoro-1-methylethyl]benzamide, or a pharmaceutically acceptable salt thereof.

In some embodiments, the present application provides 5-[3-(cyanomethyl)-3-(3,3'-dimethyl-1H,1'H-4,4'-bipyrazol-1-yl)azetidin-1-yl]-N-isopropylpyrazine-2-carboxamide, or a pharmaceutically acceptable salt thereof.

In some embodiments, the present application provides 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the present application provides 5-[3-(cyanomethyl)-3-(3',5'-dimethyl-1H,1'H-4,4'-bipyrazol-1-yl)azetidin-1-yl]-N-isopropylpyrazine-2-carboxamide, or a pharmaceutically acceptable salt thereof.

In some embodiments, the present application 5-[3-(cyanomethyl)-3-(3',5'-dimethyl-1H,1'H-4,4'-bipyrazol-1-yl)azetidin-1-yl]-N-[(1S)-2,2,2-trifluoro-1-methylethyl]pyrazine-2-carboxamide, or a pharmaceutically acceptable salt thereof.

In some embodiments, the present application provides 5-[3-(cyanomethyl)-3-(3-methyl-1H,1'H-4,4'-bipyrazol-1-yl)azetidin-1-yl]-N-isopropylpyrazine-2-carboxamide, or a pharmaceutically acceptable salt thereof.

In some embodiments, the present application provides 5-[3-(cyanomethyl)-3-(3'-ethyl-1H,1'H-4,4'-bipyrazol-1-yl)azetidin-1-yl]-N-[(1S)-2,2,2-trifluoro-1-methylethyl]pyrazine-2-carboxamide, or a pharmaceutically acceptable salt thereof.

In some embodiments, the present application provides 4-{3-(cyanomethyl)-3-[3'-(hydroxymethyl)-1H,1'H-4,4'-bipyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the present application provides 4-{3-(cyanomethyl)-3-[3-(hydroxymethyl)-3'-methyl-1H,1'H-4,4'-bipyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the present application provides a salt selected from:

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt;

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt;

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt; and 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt.

In some embodiments, the salt is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt. In some embodiments, the salt is a 1:1 stoichiometric ratio of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide to phosphoric acid. In some embodiments, the salt is crystalline. In some embodiments, the salt is substantially isolated.

In some embodiments, the salt is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt. In some embodiments, the salt is a 1:1 stoichiometric ratio of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide to hydrochloric acid. In some embodiments, the salt is crystalline. In some embodiments, the salt is substantially isolated.

In some embodiments, the salt is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt. In some embodiments, the salt is a 1:1 stoichiometric ratio of 4-[3-(cyanomethyl)-3-(3',5'-dimethyl-1H,1'H-4,4'-bipyrazol-1-yl)azetidin-1-yl]-2,5-difluoro-N-

[(1S)-2,2,2-trifluoro-1-methylethyl]benzamide to hydrobromic acid. In some embodiments, the salt is crystalline. In some embodiments, the salt is substantially isolated.

In some embodiments, the salt is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt. In some embodiments, the salt is a 1:1 stoichiometric ratio of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide to sulfuric acid. In some embodiments, the salt is crystalline. In some embodiments, the salt is substantially isolated.

Figure 4A:
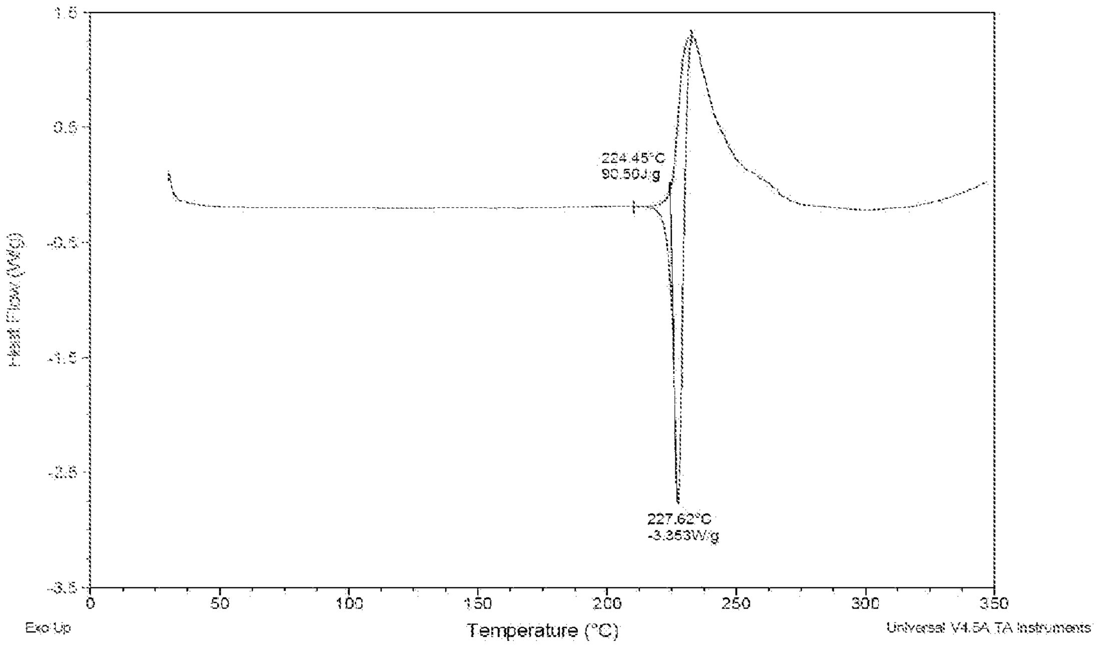
FIG. 4A shows a DSC thermogram characteristic of the salt of Example 17.
Figure 4B:
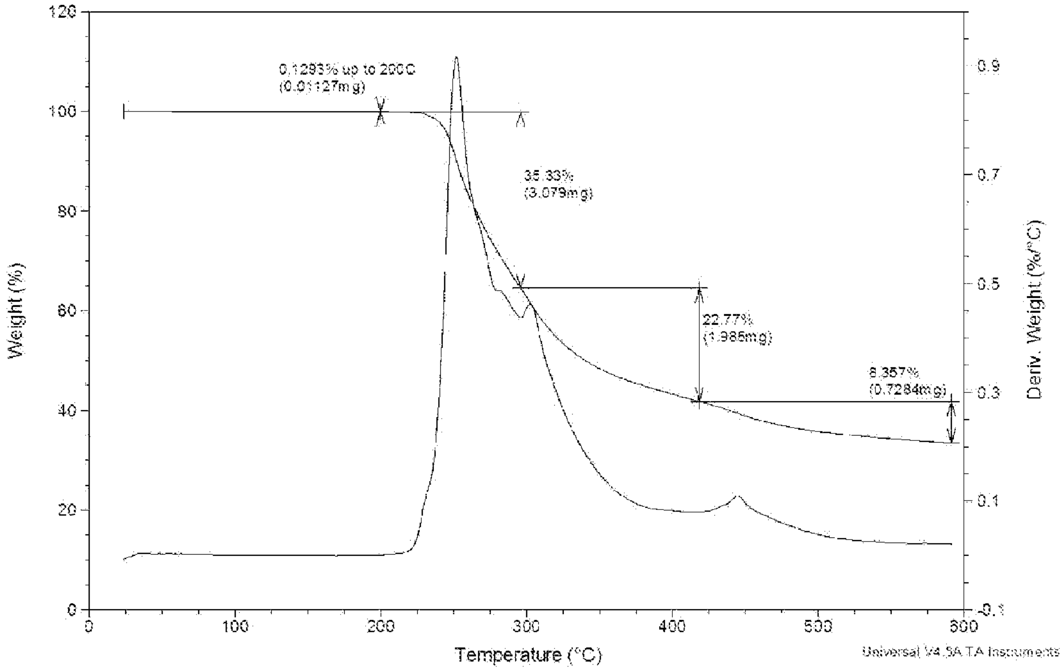
FIG. 4B shows TGA data characteristic of the salt of Example 17.
Figure 4C:
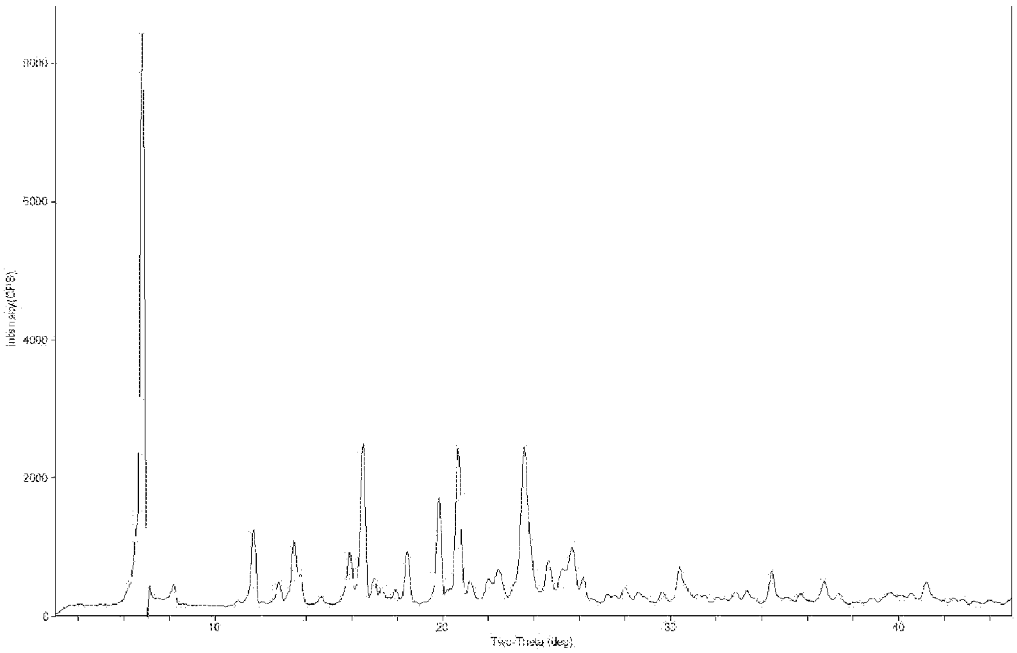
FIG. 4C shows an XRPD pattern characteristic of the salt of Example 17.

In some embodiments, the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt is characterized by a DSC thermogram having an endothermic peak at about 228° C. In some embodiments, the phosphoric acid salt has a DSC thermogram substantially as shown in FIG. 4A. In some embodiments, the phosphoric acid salt has at least one XRPD peak, in terms of 2-theta, selected from about 6.8°, about 16.5°, about 19.8°, about 20.7°, and about 23.6°. In some embodiments, the phosphoric acid salt has at least two XRPD peaks, in terms of 2-theta, selected from about 6.8°, about 16.5°, about 19.8°, about 20.7°, and about 23.6°. In some embodiments, the phosphoric acid salt has at least three XRPD peaks, in terms of 2-theta, selected from about 6.8°, about 16.5°, about 19.8°, about 20.7°, and about 23.6°. In some embodiments, the phosphoric acid salt has at least four XRPD peaks, in terms of 2-theta, selected from about 6.8°, about 16.5°, about 19.8°, about 20.7°, and about 23.6°. In some embodiments, the phosphoric acid salt has an XRPD profile substantially as shown in FIG. 4C.

Figure 5A:
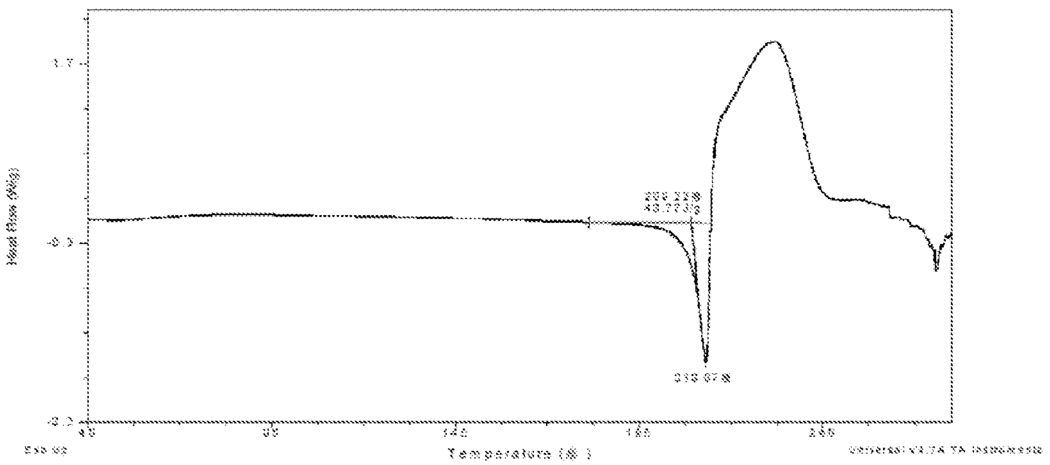
FIG. 5A shows a DSC thermogram characteristic of the salt of Example 18.
Figure 5B:
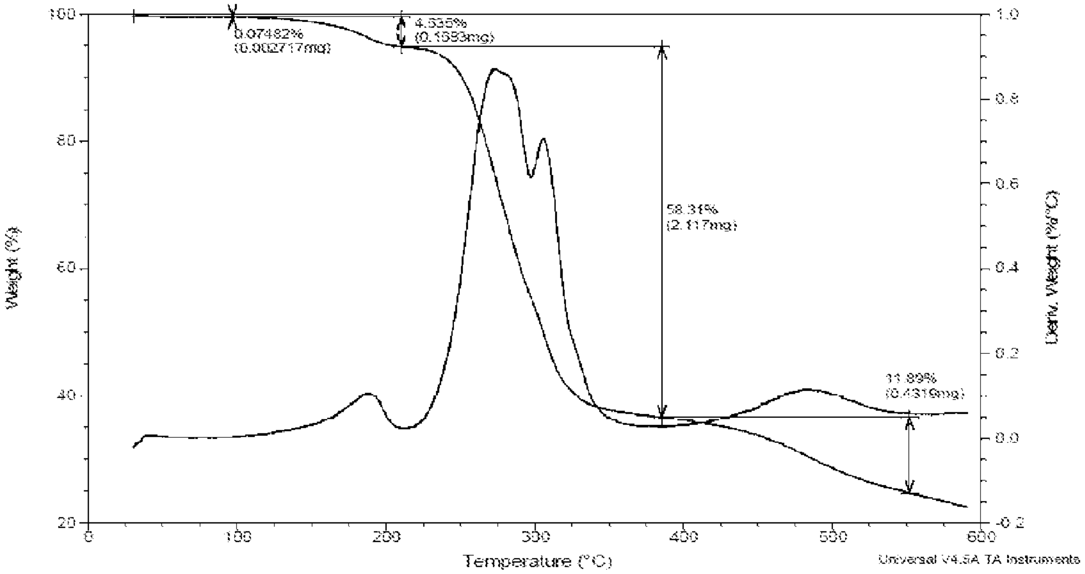
FIG. 5B shows TGA data characteristic of the salt of Example 18.
Figure 5C:
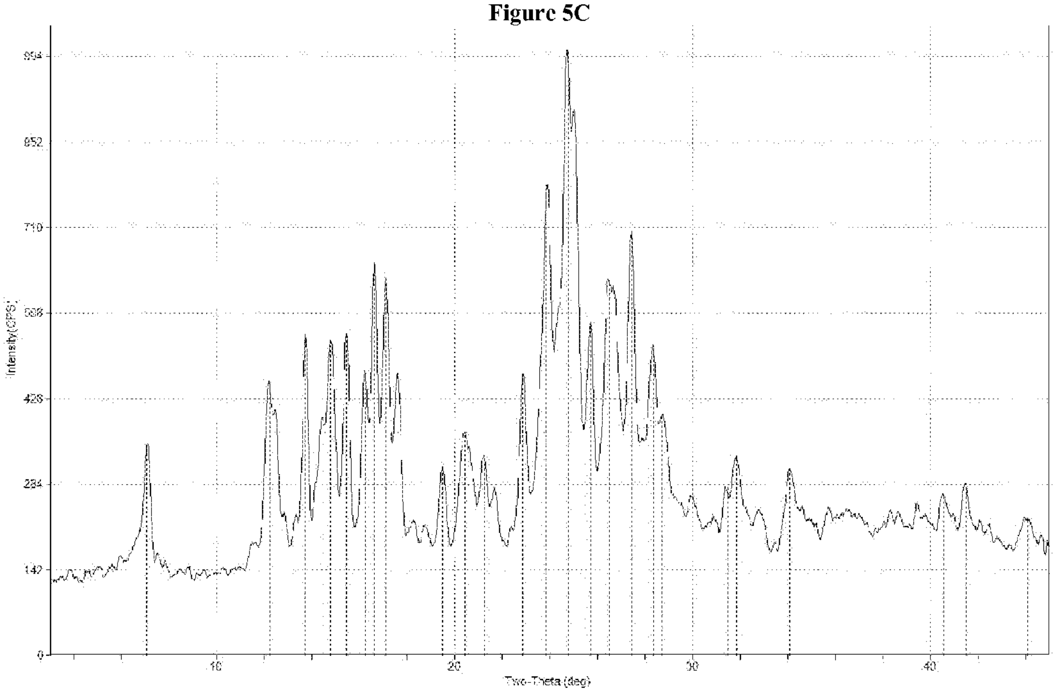
FIG. 5C shows an XRPD pattern characteristic of the salt of Example 18.

In some embodiments, the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt is characterized by a DSC thermogram having an endothermic peak at about 213° C. In some embodiments, the hydrochloric acid salt has a DSC thermogram substantially as shown in FIG. 5A. In some embodiments, the hydrochloric acid salt has at least one XRPD peak, in terms of 2-theta, selected from about 7.0°, about 12.1°, about 13.7°, about 14.8°, about 15.5°, about 16.6°, about 17.1°, about 19.7°, about 20.4°, about 20.8°, about 23.9°, about 24.7°, about 25.1°, about 25.7°, about 27.4°, and about 28.3°. In some embodiments, the hydrochloric acid salt has at least two XRPD peaks, in terms of 2-theta, selected from about 7.0°, about 12.1°, about 13.7°, about 14.8°, about 15.5°, about 16.6°, about 17.1°, about 19.7°, about 20.4°, about 20.8°, about 23.9°, about 24.7°, about 25.1°, about 25.7°, about 27.4°, and about 28.3°. In some embodiments, the hydrochloric acid salt has at least three XRPD peaks, in terms of 2-theta, selected from about 7.0°, about 12.1°, about 13.7°, about 14.8°, about 15.5°, about 16.6°, about 17.1°, about 19.7°, about 20.4°, about 20.8°, about 23.9°, about 24.7°, about 25.1°, about 25.7°, about 27.4°, and about 28.3°. In some embodiments, the hydrochloric acid salt has at least four XRPD peaks, in terms of 2-theta, selected from about 7.0°, about 12.1°, about 13.7°, about 14.8°, about 15.5°, about 16.6°, about 17.1°, about 19.7°, about 20.4°, about 20.8°, about 23.9°, about 24.7°, about 25.1°, about 25.7°, about 27.4°, and about 28.3°. In some embodiments, the hydrochloric acid salt has an XRPD profile substantially as shown in FIG. 5C.

Figure 7A:
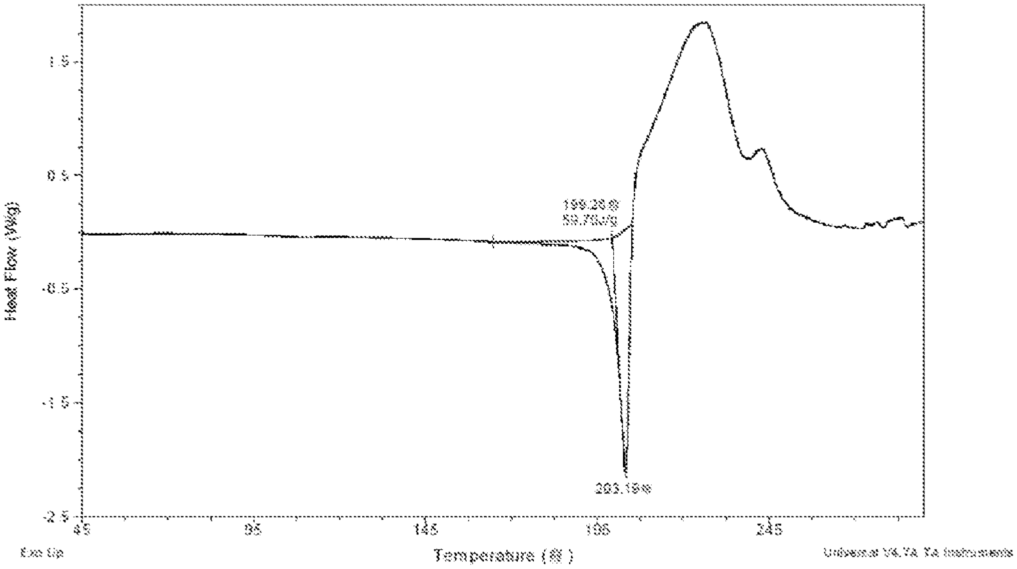
FIG. 7A shows a DSC thermogram characteristic of the salt of Example 20.
Figure 7B:
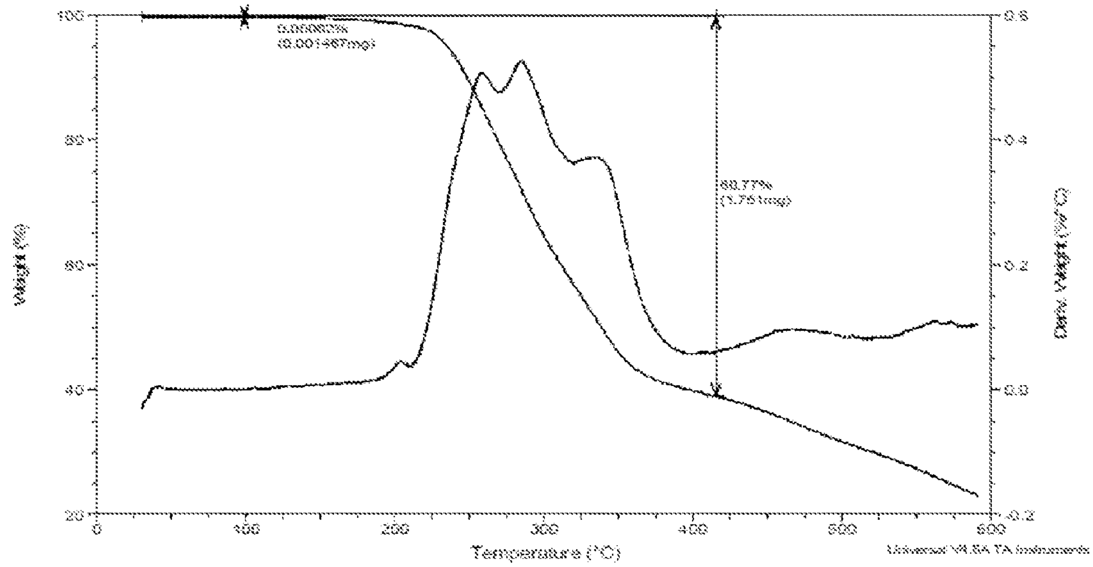
FIG. 7B shows TGA data characteristic of the salt of Example 20.
Figure 7C:
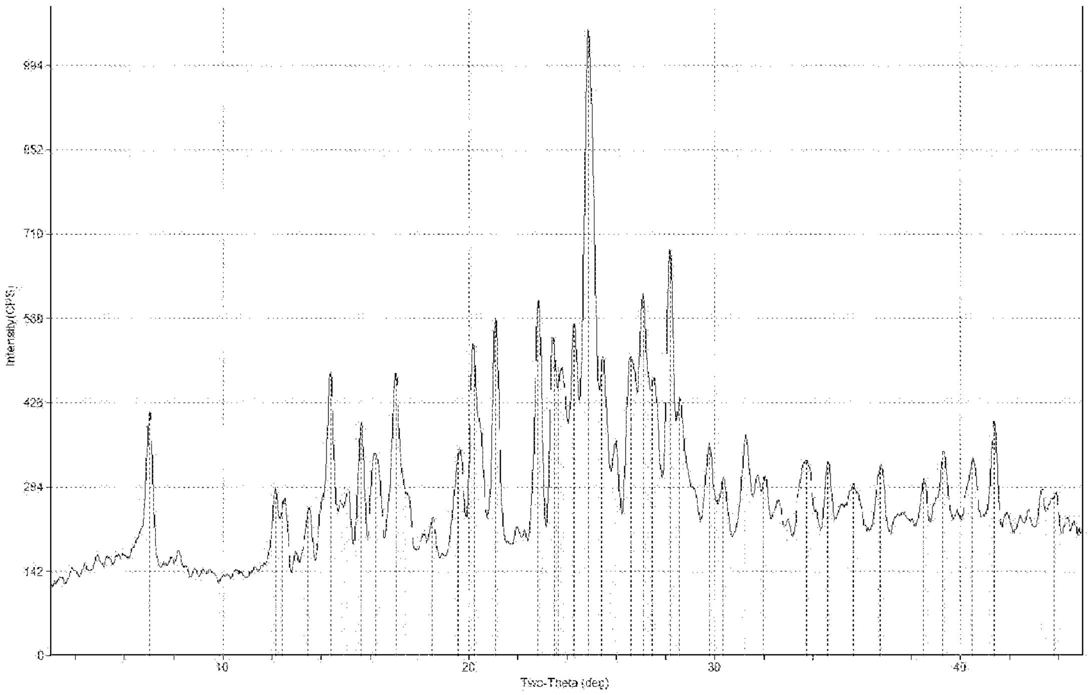
FIG. 7C shows an XRPD pattern characteristic of the salt of Example 20.

In some embodiments, the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt is characterized by a DSC thermogram having an endothermic peak at about 203° C. In some embodiments, the hydrobromic acid salt has a DSC thermogram substantially as shown in FIG. 7A. In some embodiments, the hydrobromic acid salt has at least one XRPD peak, in terms of 2-theta, selected from about 7.0°, about 14.4°, about 17.1°, about 20.2°, about 21.1°, about 22.8°, about 23.5°, about 24.9°, about 26.6°, about 27.1°, and about 28.2°. In some embodiments, the hydrobromic acid salt has least two XRPD peaks, in terms of 2-theta, selected from about 7.0°, about 14.4°, about 17.1°, about 20.2°, about 21.1°, about 22.8°, about 23.5°, about 24.9°, about 26.6°, about 27.1°, and about 28.2°. In some embodiments, the hydrobromic acid salt has least three XRPD peaks, in terms of 2-theta, selected from about 7.0°, about 14.4°, about 17.1°, about 20.2°, about 21.1°, about 22.8°, about 23.5°, about 24.9°, about 26.6°, about 27.1°, and about 28.2°. In some embodiments, the hydrobromic acid salt has least four XRPD peaks, in terms of 2-theta, selected from about 7.0°, about 14.4°, about 17.1°, about 20.2°, about 21.1°, about 22.8°, about 23.5°, about 24.9°, about 26.6°, about 27.1°, and about 28.2°. In some embodiments, the hydrobromic acid salt has an XRPD profile substantially as shown in FIG. 7C.

Figure 8A:
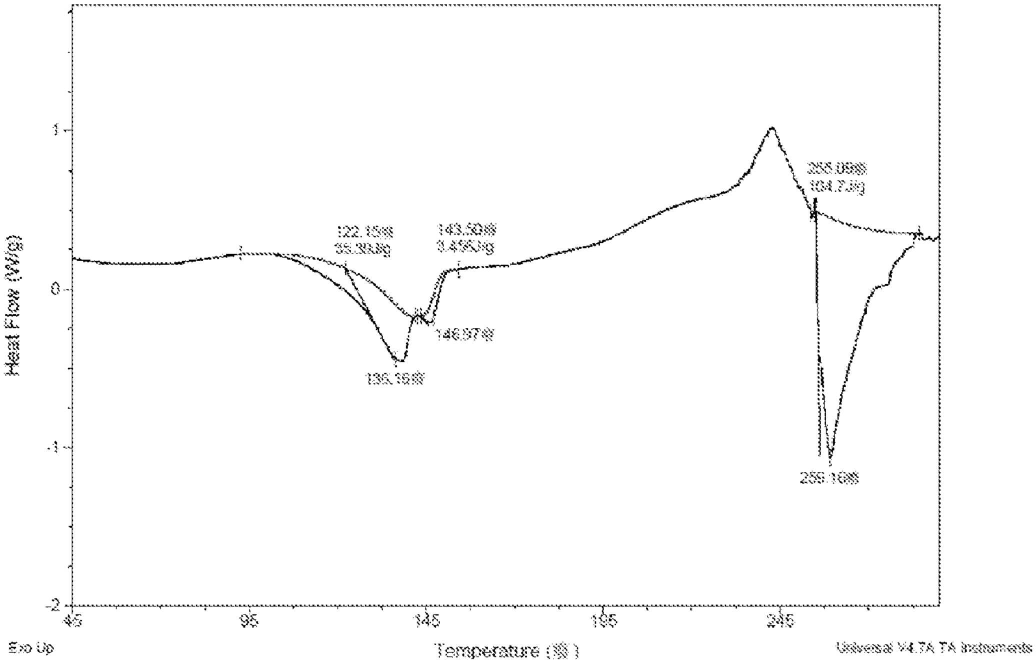
FIG. 8A shows a DSC thermogram characteristic of the salt of Example 21.
Figure 8B:
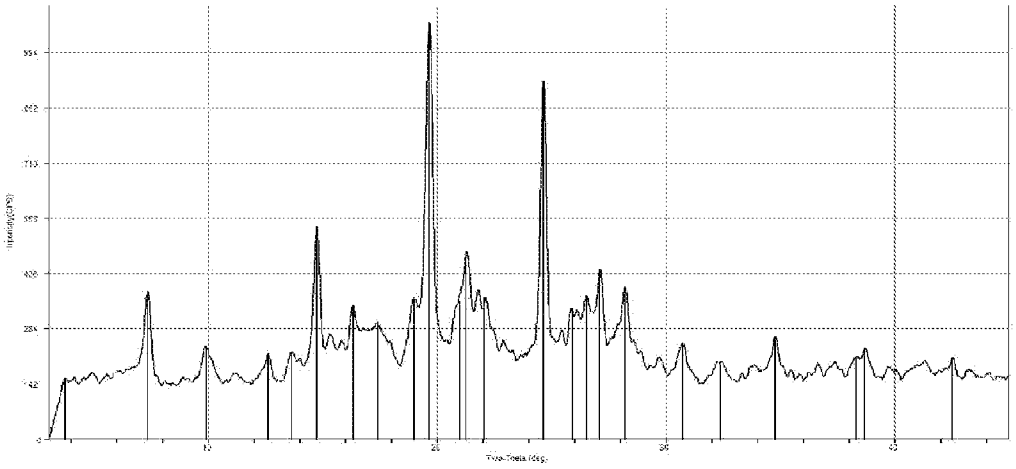
FIG. 8B shows an XRPD pattern characteristic of the salt of Example 21.

In some embodiments, the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt is characterized by a DSC thermogram having an endothermic peak at about 259° C. In some embodiments, the sulfuric acid salt is characterized by a DSC thermogram having three endothermic peaks at about 136° C., about 147° C., and about 259° C. In some embodiments, the sulfuric acid salt has a DSC thermogram substantially as shown in FIG. 8A. In some embodiments, the sulfuric acid salt has at least one XRPD peak, in terms of 2-theta, selected from about 7.3°, about 14.7°, about 9.9°, about 19.0°, about 19.6°, about 21.3°, and about 24.6°. In some embodiments, the sulfuric acid salt has at least two XRPD peaks, in terms of 2-theta, selected from about 7.3°, about 14.7°, about 9.9°, about 19.0°, about 19.6°, about 21.3°, and about 24.6°. In some embodiments, the sulfuric acid salt has at least three XRPD peaks, in terms of 2-theta, selected from about 7.3°, about 14.7°, about 9.9°, about 19.0°, about 19.6°, about 21.3°, and about 24.6°. In some embodiments, the sulfuric acid salt has at least four XRPD peaks, in terms of 2-theta, selected from about selected from about 7.3°, about 14.7°, about 9.9°, about 19.0°, about 19.6°, about 21.3°, and about 24.6°. In some embodiments, the sulfuric acid salt has an XRPD profile substantially as shown in FIG. 8B.

Different crystalline forms may have different crystalline lattices (e.g., unit cells) and, usually as a result, have different physical properties. The different salt forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term “peak” refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the salts described herein are substantially isolated. By "substantially isolated" is meant that the compound is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating compounds and their salts are routine in the art.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a piperidine ring"). Unless otherwise specified, these rings can be attached to the rest of the molecule at any ring member as permitted by valency. For example, the term "a 2H-tetrahydropyran ring" may refer to a 2H-tetrahydropyran-2-yl, 2H-tetrahydropyran-3-yl, 2H-tetrahydropyran-4-yl ring, etc.

The term "n-membered" where n is an integer typically describes the number of ring-forming atoms in a moiety where the number of ring-forming atoms is n. For example, 2H-tetrahydropyran is an example of a 6-membered heterocycloalkyl ring, 1H-1,2,4-triazole is an example of a 5-membered heteroaryl ring, pyridine is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

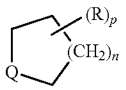

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "alkylene", employed alone or in combination with other terms, refers to a divalent alkyl linking group, which can be branched or straight-chain, where the two substituents may be attached any position of the alkylene linking group. Examples of alkylene groups include, but are not limited to, ethan-1,2-diyl, propan-1,3-diyl, propan-1,2-diyl, and the like.

As used herein, "$C_{n-m}$ alkenyl" refers to an alkyl group having one or more double carbon-carbon bonds and having n to m carbons. In some embodiments, the alkenyl moiety contains 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 3 carbon atoms.

As used herein, the term "$C_{1-3}$ alkoxy", employed alone or in combination with other terms, refers to a group of formula —O-alkyl, wherein the alkyl group has 1 to 3 carbons. Example alkoxy groups include methoxy, ethoxy, and propoxy (e.g., n-propoxy and isopropoxy).

As used herein, the term "$CF_3$—$C_{1-3}$ hydroxyalkyl" refers to a $C_{1-3}$ alkyl group substituted by one $CF_3$ group and one OH group.

The $C_{1-3}$ groups in $(C_{1-3}\text{ alkyl})_2N$—, $(C_{1-3}\text{ alkyl})_2N$—S(═O)$_2$NH—, and $(C_{1-3}\text{ alkyl})_2N$—C(═O)NH— can be the same or different.

As used herein, the term "carboxy" refers to a group of formula —C(═O)OH.

As used herein, the term "carbamyl" refers to a group of formula —C(═O)—$NH_2$.

As used herein, the term "$C_{1-3}$ alkylcarbamyl" refers to a group of formula —C(═O)—NH(alkyl), wherein the alkyl group has 1 to 3 carbon atoms.

As used herein, the term "di($C_{1-3}$-alkyl)carbamyl" refers to a group of formula —C(═O)N$(alkyl)_2$, wherein the two alkyl groups each has, independently, 1 to 3 carbon atoms.

As used herein, the term "HO—$C_{n-m}$-alkyl" refers to a group of formula -alkylene-OH, wherein said alkylene group has n to m carbon atoms. In some embodiments, the alkylene group has 1 to 3 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 3 carbon atoms.

As used herein, "halo" or "halogen", employed alone or in combination with other terms, includes fluoro, chloro, bromo, and iodo. In some embodiments, the halo group is fluoro or chloro.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1-6 or 1-3 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, the term "$C_{1-3}$ fluoroalkyl" refers to a $C_{1-3}$ alkyl group that may be partially or completely substituted by fluoro atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "cyano-$C_{n-m}$ alkyl" refers to a $C_{n-m}$ alkyl substituted by a cyano group. In some embodiments, the alkyl group has 1 to 3 carbon atoms.

As used herein, the appearance of the term "monocyclic" before the name of a moiety indicates that the moiety has a single ring.

As used herein, the term "phenylalkyl" refers to a group of formula -alkylene-phenyl In some embodiments, phenylalkyl is phenyl-$C_{1-3}$ alkyl.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused, spirocyclic, or bridged rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is a 3-7 membered cycloalkyl, which is monocyclic or bicyclic. In some embodiments, cycloalkyl is a 3-6 or 3-7 monocyclic cycloalkyl. Exemplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula -alkylene-cycloalkyl. In some embodiments, cycloalkylalkyl is $C_{3-7}$ cycloalkyl-$C_{1-3}$ alkyl, wherein the cycloalkyl portion is monocyclic.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is a 5-6 membered heteroaryl, which is monocyclic or bicyclic, comprising 1 to 5 carbon atoms and 1, 2, 3, or 4 heteroatom ring members independently selected from nitrogen, sulfur, and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula -alkylene-heteroaryl. In some embodiments, heteroarylalkyl is 5-6 membered heteroaryl-$C_{1-3}$ alkyl, wherein the heteroaryl portion is monocyclic, comprising 1 to 5 carbon atoms and 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused, spirocyclic, or bridged rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 4-7 membered heterocycloalkyl, which is monocyclic, comprising 2-6 carbon atoms and 1, 2, 3, or 4 heteroatom ring members independently selected from nitrogen, sulfur, and oxygen. Examples of heterocycloalkyl groups include azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula -alkylene-heterocycloalkyl. In some embodiments, heterocycloalkylalkyl is 4-7 membered heterocycloalkyl-$C_{1-3}$ alkyl, wherein the heterocycloalkyl portion is monocyclic, comprising 2-6 carbon atoms and 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. For example, it will be recognized that the following pyrazole ring may form two tautomers:

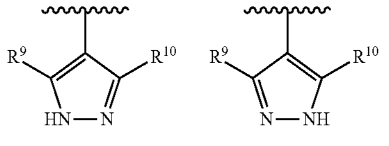

It is intended that the claims cover both tautomers.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ groups in the azetidine ring of Formula I are replaced by a CHD or $CD_2$ group. In some embodiments, 1, 2, or 3 $CH_2$ or CH groups in the piperidine ring of Formula I are replaced by a CHD, $CD_2$ or CD group, respectively. In some embodiments, 1, 2, 3, 4, or 5 $CH_2$ or CH groups in the piperidine ring of Formula I are replaced by a CHD, $CD_2$ or CD group, respectively.

The term, "compound," as used herein is meant to include all stereoisomers, geometric iosomers, tautomers, and isotopes of the structures depicted. Further, compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

Compounds of Formula I can be synthesized by procedures analogous to those in the schemes below. A series of bipyrazole derivatives 9 can be prepared according to the methods outlined in Scheme 1. An aromatic acid 1 can be conveniently converted to the corresponding amide 2 by using the amide coupling reagent such as BOP, PyOP, HATU, HBTU, EDC, or CDI. Replacement of the leaving group Hal (Hal can be halogen, OTs or OTf) in 2 by 3-hydroxyazetidine to produce compound 3 can be achieved under thermal conditions in a suitable solvent such as, but not limited to, DMSO, dioxane, DMF, or NMP in the presence of a base such as potassium carbonate, cesium carbonate, or sodium carbonate; or under copper-catalyzed Ullmann type N-arylation reaction conditions by using copper(I) iodide and potassium carbonate; or under palladium-catalyzed C—N bond forming reaction conditions using xanthpos, BINAP, or P(o-Tol)$_3$ as the ligand and potassium carbonate or cesium carbonate as the base. α,β-Unsaturated nitrile 5 can be obtained by Wittig's reaction of diethyl cyanomethylphosphonate with the ketone 4 which can be prepared by Swern oxidation of 3. Michael addition of 6 with α,β-unsaturated nitrile 5 can afford the boronic ester 7. Suzuki coupling of the boronic ester 7 with a suitable pyrazole halide 8 can afford the corresponding bipyrazole derivative 9.

Scheme 1

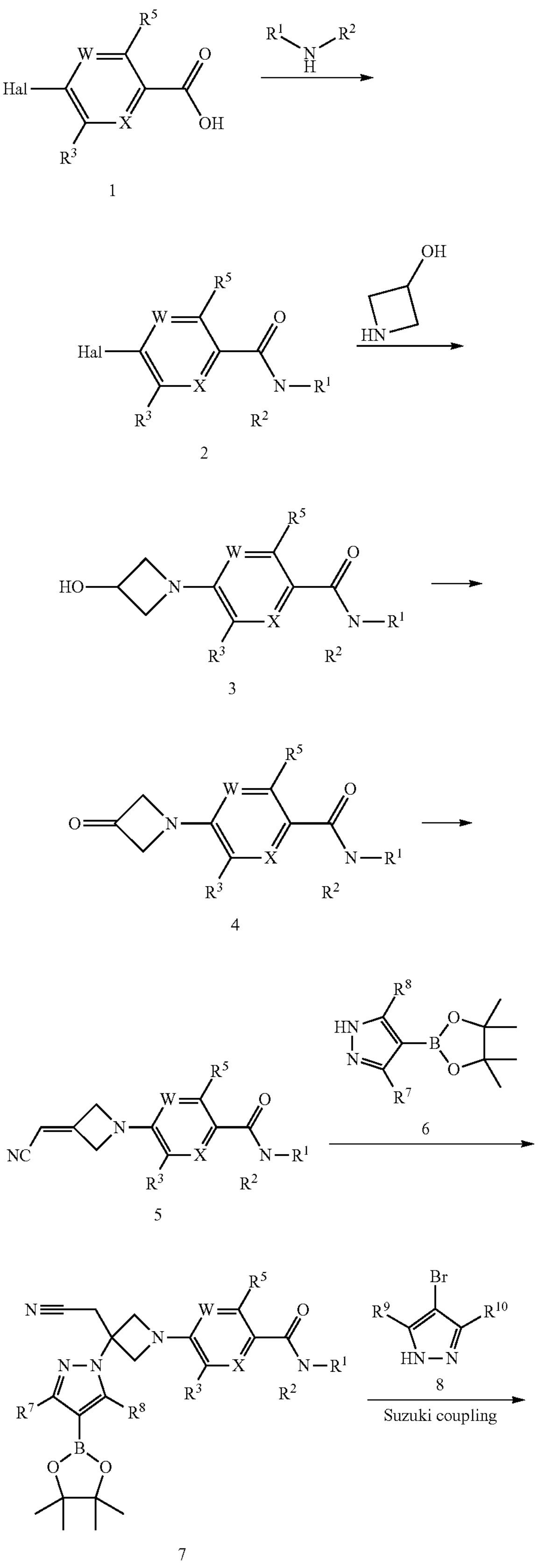

-continued

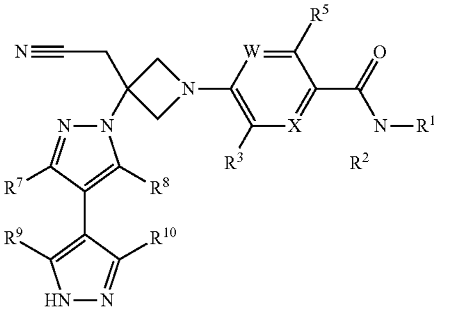

9

-continued

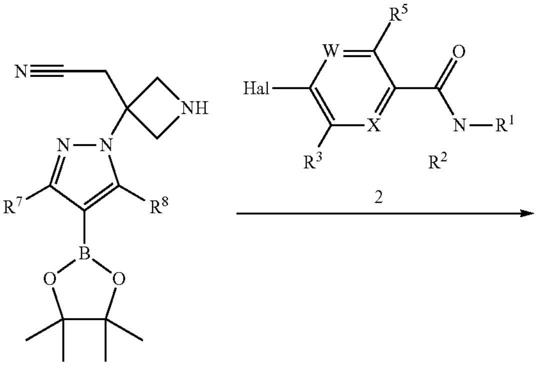

12

2

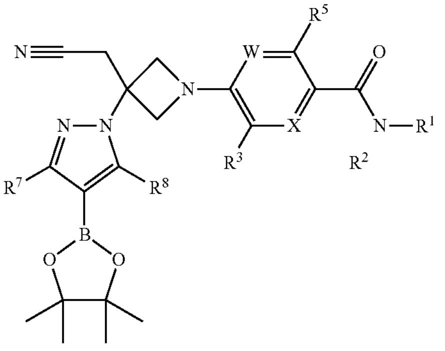

7

A series of boronic ester derivatives 7 can be prepared according to the procedures outlined in Scheme 2. Michael addition of 6 with α,β-unsaturated nitrile 10 can afford the boronic ester 11. Removal of the Boc-group can be achieved under acid conditions to afford the corresponding amine 12. Replacement of the leaving group Hal in 2 by 12 can produce the boronic ester 7 under thermal conditions in a suitable solvent such as, but not limited to, acetonitrile, DMSO, dioxane, DMF, or NMP in the presence of a base such as potassium carbonate, cesium carbonate, sodium carbonate, hunig's base or DBU.

Scheme 2

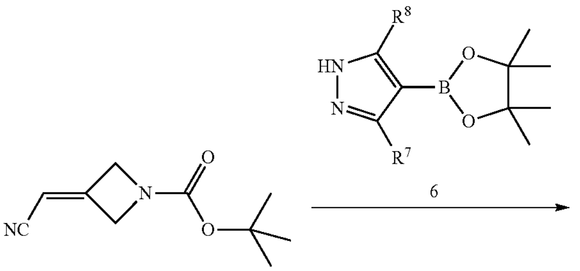

10

6

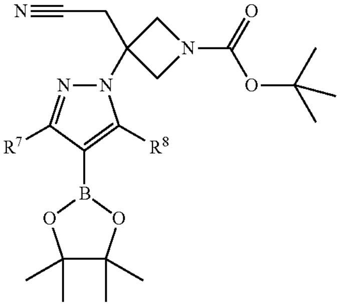

11

A series of bi-pyrazole derivatives 21 can be prepared according to the methods outlined in Scheme 3. Halo-aromatic esters 13 can be converted to the corresponding alkenes 14 by Suzuki coupling of the halo-aromatic esters 13 with vinyl boronic esters. Alkenes 14 can be reacted with appropriately substituted ketenes (such as dichcloroketene) under 2+2 cycloadditions to give the dichlorocyclobutanones 15. Under reducing conditions (such as zinc in acetic acid under thermal conditions) the dichlorocyclobutanones 15 can be converted to cyclobutanones 16. α,β-Unsaturated nitriles 17 can be formed by reaction of the cyclobutanones 16 with Horner-Wadsworth-Emmons reagent. Boronic esters 6 can be reacted with α,β-unsaturated nitriles 17 in Michael addition conditions in the presence of coupling agents to give the compounds 18. Suzuki coupling of the boronic esters 18 with suitable pyrazole halides 8 can afford the corresponding bi-pyrazoles 19. Hydrolysis of esters 19 under basic conditions can give the acids 20. The amides 21 can be synthesized by coupling of acids 20 with appropriately substituted amines using amide coupling reagents such as BOP, PyBop, HATU, HBTU, EDC, or CDI.

Scheme 3

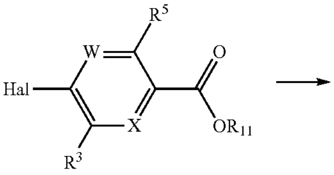

13

-continued

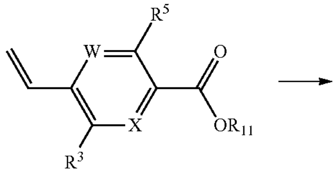

14

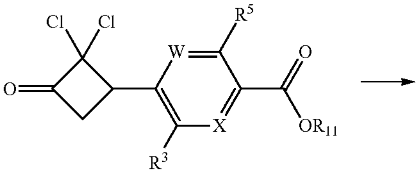

15

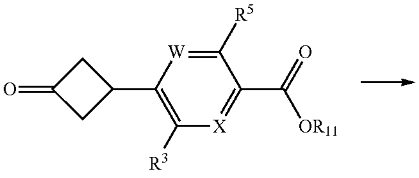

16

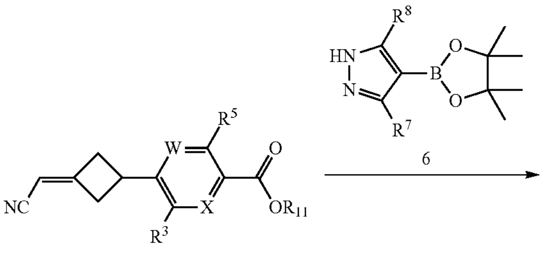

17

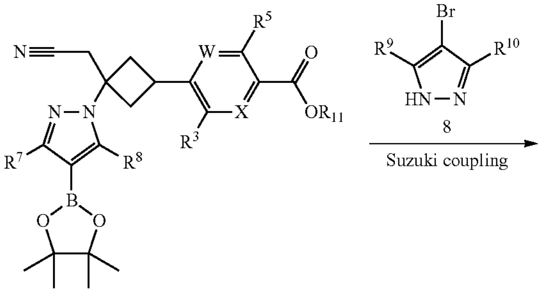

18

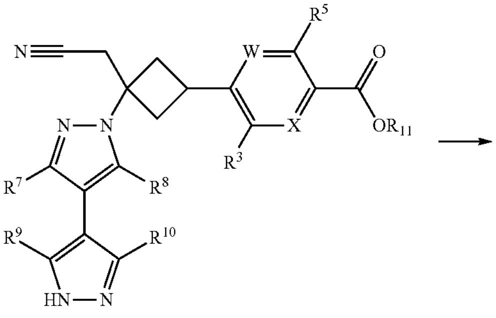

19

-continued

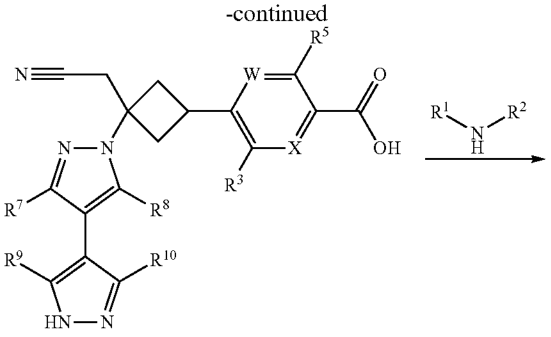

20

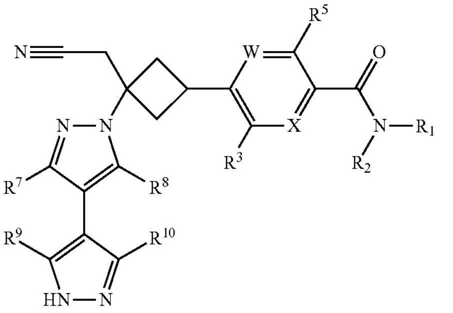

21

Processes

The present application provides a process of forming the salts described herein comprising reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with an acid selected from phosphoric acid, hydrochloric acid, hydrobromic acid, and sulfuric acid to form the salt thereof. In some embodiments, the process utilizes from about 0.55 to 1.5 equivalents of the acid per equivalent of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide.

In some embodiments, the process comprises reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with phosphoric acid in a solvent component at a temperature above room temperature to form the phosphoric acid salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide. In some embodiments, the temperature is from about 40° C. to about 70° C. In some embodiments, the temperature is about 45° C. to about 55° C. In some embodiments, the solvent component comprises ethanol. In some embodiments, the solvent component comprises acetonitrile. In some embodiments, the solvent component comprises isopropanol. In some embodiments, the solvent component comprises methanol. In some embodiments, the solvent component comprises methanol and isopropanol. In some embodiments, the solvent component comprises methanol, isopropanol, and n-heptane. In some embodiments, the process further comprises cooling the mixture to room temperature and filtering to isolate the salt. In some embodiments, the process further comprises removing a portion of the solvent to form a concentrated mixture before said filtering. In some embodiments, a portion of the solvent is removed by distillation.

The present application further provides a process of forming 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt, comprising reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with phosphoric acid in a solvent component comprising methanol and isopropanol at a temperature from about 40° C. to about 70° C. form a mixture comprising phosphoric acid salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt. In some embodiments, the process further comprises adding n-heptane to the mixture at a temperature from about 40° C. to about 70° C. to form a second mixture. In some embodiments, the reacting is conducted at a temperature from about 45° C. to about 55° C. In some embodiments, the reacting is conducted at a temperature of about 50° C.

In some embodiment, the present application further provides a process of preparing 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt, comprising:

(a) dissolving the 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt in methanol at a temperature from about 40° C. to about 70° C. to form a first mixture;

(b) adding n-heptane to the first mixture at a temperature from about 40° C. to about 70° C. to form a second mixture; and (c) cooling the second mixture to provide 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

In some embodiments, the process of the preceding embodiment further comprises distilling at least a portion of the methanol from the first mixture prior to step (b). In some embodiments, the process the preceding embodiment further comprises distilling at least a portion of the methanol and/or n-heptane from the second mixture prior to step (c). In some embodiments, steps (a) and (b) are conducted at a temperature from about 45° C. to about 55° C. In some embodiments, steps (a) and (b) are conducted at a temperature of about 50° C.

In some embodiments, the process comprises reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with hydrochloric acid in a solvent component at a temperature above room temperature to form the hydrochloric acid salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide. In some embodiments, the reacting is conducted at a temperature at about room temperature. In some embodiments, the solvent component comprises 2-butanol. In some embodiments, the solvent component comprises isopropanol. In some embodiments, the solvent component comprises isopropanol and isopropylacetate. In some embodiments, the process further comprises filtering to isolate the salt. In some embodiments, the process further comprises washing the isolated salt with methyl tert-butyl ether.

In some embodiments, the process comprises reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with hydrobromic acid in a solvent component at a temperature above room temperature to form the hydrobromic acid salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide. In some embodiments, the reacting is conducted at a temperature at about room temperature. In some embodiments, the solvent component comprises isopropanol. In some embodiments, the solvent component comprises isopropanol and water. In some embodiments, the process further comprises filtering to isolate the salt. In some embodiments, the process further comprises washing the isolated salt with methyl tert-butyl ether.

In some embodiments, the process comprises reacting 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide with sulfuric acid in a solvent component to form the sulfuric acid salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide. In some embodiments, the reacting is conducted at a temperature at about room temperature. In some embodiments, the solvent component comprises isopropanol. In some embodiments, the process further comprises filtering to isolate the salt. In some embodiments, the reacting is conducted at a temperature at about 60° C. In some embodiments, the solvent component comprises isopropanol and water. In some embodiments, the process further comprises cooling the mixture to room temperature and filtering to isolate the salt. In some embodiments, the process further comprises washing the isolated salt with methyl tert-butyl ether.

Methods

Compounds of the invention are JAK inhibitors, and the majority of the compounds of the invention, are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio >1). In some embodiments, the compounds are about 10-fold more selective for JAK1 over JAK2. In some embodiments, the compounds are about 3-fold, about 5-fold, about 10-fold, about 15-fold, or about 20-fold more selective for JAK1 over JAK2 as calculated by measuring $IC_{50}$ at 1 mM ATP (e.g., see Example A).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

In some embodiments, JAK inhibitors described herein can be further used to treat myelodysplastic syndrome (MDS) in a patient in need thereof. In some embodiments, said patient is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br J Haematol* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues*. 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues*. (ed. 4th edition): Lyon, France: IARC Press; 2008:88-103).

In some embodiments, the myelodysplastic syndrome is refractory cytopenia with unilineage dysplasia (RCUD). In some embodiments, the myelodysplastic syndrome is refractory anemia with ring sideroblasts (RARS).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

TABLE 1

2008 WHO Classification for De Novo Myelodysplastic Syndrome

| Subtype | Blood | Bone Marrow |
| --- | --- | --- |
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × 10$^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × 10$^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × 10$^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating JAK1. In some embodiments, the present invention also provides use of a compound of Formula I as described herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

The methods described herein can further comprise administering one or more additional therapeutic agents. The one or more additional therapeutic agents can be administered to a patient simultaneously or sequentially.

In some embodiments, the method further comprises administering an additional therapeutic agent selected from IMiDs, an anti-IL-6 agent, an anti-TNF-$\alpha$ agent, a hypomethylating agent, and a biologic response modifier (BRM).

Generally, a BRM is a substances made from living organisms to treat disease, which may occur naturally in the body or may be made in the laboratory. Examples of BRMs include IL-2, interferon, various types of colony-stimulating factors (CSF, GM-CSF, G-CSF), monoclonal antibodies such as abciximab, etanercept, infliximab, rituximab, trasturzumab, and high dose ascorbate.

In some embodiments, the anti-TNF-α agent is infliximab, and etanercept.

In some embodiments, the hypomethylating agent is a DNA methyltransferase inhibitor. In some embodiments, the DNA methyltransferase inhibitor is selected from 5 azacytidine and decitabine.

Generally, IMiDs are as immunomodulatory agents. In some embodiments, the IMiD is selected from thalidomide, lenalidomide, pomalidomide, CC-11006, and CC-10015.

In some embodiments, the method further comprises administering an additional therapeutic agent selected from anti-thymocyte globulin, recombinant human granulocyte colony-stimulating factor (G CSF), granulocyte-monocyte CSF (GM-CSF), a erythropoiesis-stimulating agent (ESA), and cyclosporine.

In some embodiments, the method further comprises administering an additional JAK inhibitor to the patient. In some embodiments, the additional JAK inhibitor is tofacitinib or ruxolitinib.

One or more additional pharmaceutical agents such as, for example, chemotherapeutics, anti-inflammatory agents, steroids, immunosuppressants, as well as PI3Kδ, mTor, Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, a suitable chemotherapeutical agent can be selected from antimetabolite agents, topoisomerase 1 inhibitors, platinum analogs, taxanes, anthracyclines, and EGFR inhibitors, and combinations thereof.

In some embodiments, antimetabolite agents include capecitabine, gemcitabine, and fluorouracil (5-FU).

In some embodiments, taxanes include paclitaxel, Abraxane® (paclitaxel protein-bound particles for injectable suspension), and Taxotere® (docetaxel).

In some embodiments, platinum analogs include oxaliplatin, cisplatin, and carboplatin.

In some embodiments, topoisomerase 1 inhibitors include irinotecan and topotecan.

In some embodiment, anthracyclines include doxorubicin or liposomal formulations of doxorubicin.

In some embodiments, the chemotherapeutic is FOLFIRINOX (5-FU, lecovorin, irinotecan and oxaliplatin). In some embodiments, the chemotherapeutic agent is gemcitabine and Abraxane® (paclitaxel protein-bound particles for injectable suspension).

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC 1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an anti-metabolite/demethylating agent (e.g., 5-flurouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 1 to about 1,000 mg, from about 1 mg to about 100 mg, from 1 mg to about 50 mg, and from about 1 mg to 10 mg of active ingredient. Preferably, the dosage is from about 1 mg to about 50 mg or about 1 mg to about 10 mg of active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions comprise from about 1 to about 1,000 mg, from about 1 mg to about 100 mg, from 1 mg to about 50 mg, and from about 1 mg to 10 mg of active ingredient. Preferably, the compositions comprise from about 1 mg to about 50 mg or about 1 mg to about 10 mg of active ingredient. One having ordinary skill in the art will appreciate that this embodies compounds or compositions containing about 1 mg to about 10 mg, about 1 mg to about 20 mg, about 1 mg to about 25 mg, about 1 mg to about 50 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol.

Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or polypropylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the choroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

Experimental procedures for compounds of the invention are provided below. Open access prep. LC-MS purification of some of the compounds prepared was performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the examples. Typical preparative reverse-phase high performance liquid chromatography (RP-HPLC) column conditions are as follows:

pH=2 purifications: Waters Sunfire™ $C_{18}$ 5 um, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with 30×100 mm column was 60 mL/minute.

pH=10 purifications: Waters XBridge $C_{18}$ 5 um, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with 30×100 mm column was 60 mL/minute.

Some of the compounds prepared were also analyzed via Differential Scanning calorimetry (DSC). Typical DSC instrument conditions are as follows:

TA Instruments Differential Scanning calorimetry, Model Q200 with autosampler. General conditions: 30-350° C. at 10° C./min; Tzero aluminum sample pan and lid; nitrogen gas flow at 50 mL/min.

Some of the compounds prepared were also analyzed via Thermogravimetric Analysis (TGA). Typical TGA instrument conditions are as follows:

TA Instrument Thermogravimetric Analyzer, Model Q500. General method conditions: ramp from 20° C. to 600° C. at 20° C./min; nitrogen purge, gas flow at 40 mL/min followed by balance of the purge flow; sample purge flow at 60 mL/min; platinum sample pan.

Some of the compounds prepared were also analyzed via X-Ray Power Diffraction (XRPD). Typical XRPD instrument conditions are as follows:

Rigaku MiniFlex X-ray Powder Diffractometer (XRPD). General experimental procedures: X-ray radiation from Copper at 1.054056 Å with $K_{\beta}$ filter; X-ray power is 30 KV, 15 mA; sample powder is dispersed on a zero-background sample holder. General measurement conditions: Start Angle—3 degrees; Stop Angle—45 degrees; Sampling—0.02 degrees; Scan speed—2 degree/min.

Example 1

5-[3-(Cyanomethyl)-3-(3'-methyl-1H,1'H-4,4'-bi-pyrazol-1-yl)azetidin-1-yl]-N-[(1S)-2,2,2-trifluoro-1-methylethyl]pyrazine-2-carboxamide trifluoroacetate

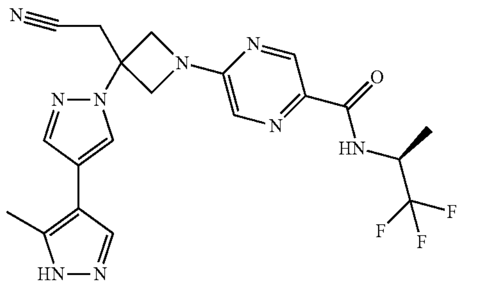 [SMILES: Cc1[nH]ncc1-c1cnn(C2(CC#N)CN(c3cnc(C(=O)N[C@@H](C)C(F)(F)F)cn3)C2)c1]

Step 1: tert-Butyl 3-(cyanomethylene)azetidine-1-carboxylate

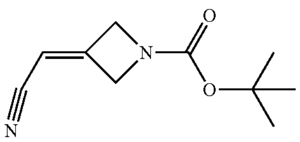

To a solution of 1.0 M potassium tert-butoxide in tetrahydrofuran (30.7 mL, 30.7 mmol) at 0° C. was added dropwise a solution of diethyl cyanomethylphosphonate (5.20 mL, 32.2 mmol) in tetrahydrofuran (39 mL). The reaction was warmed to room temperature and then cooled at 0° C. again. To the reaction mixture was added a solution of tert-butyl 3-oxoazetidine-1-carboxylate (5.0 g, 0.029 mol, from Aldrich) in tetrahydrofuran (8 mL). The reaction was allowed to warm to room temperature and stirred overnight. After quenched with water, the mixture was extracted with ethyl acetate (EtOAc). The combined organic layers were washed with brine, dried over $MgSO_4$, and evaporated under reduced pressure. The crude mixture was purified by flash chromatography on a silica gel column eluting with ethyl acetate in hexanes (0-70%) to give the desired product (5.40 g, 95%). LCMS cacld. for $C_{10}H_{14}N_2O_2Na$ $(M+Na)^+$: m/z=217.1. Found: 217.1

Step 2: tert-Butyl 3-(cyanomethyl)-3-[4-(4,4,5,5-tetramethyl-1,3,2-dioxaborolan-2-yl)-1H-pyrazol-1-yl]azetidine-1-carboxylate

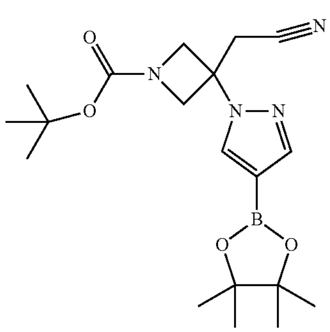 [SMILES: CC(C)(C)OC(=O)N1CC(CC#N)(n2cc(B3OC(C)(C)C(C)(C)O3)cn2)C1]

A mixture of 4-(4,4,5,5-tetramethyl-1,3,2-dioxaborolan-2-yl)-1H-pyrazole (0.990 g, 5.10 mmol), tert-butyl 3-(cyanomethylene)azetidine-1-carboxylate (1.00 g, 5.15 mmol) and 1,8-diazabicyclo[5.4.0]undec-7-ene (0.38 mL, 2.6 mmol) in acetonitrile (20 mL) was heated at 60° C. for 2 h. After cooling, the solvent was removed under reduced pressure. The residue was purified by flash chromatography on a silica gel column eluting with ethyl acetate in hexanes (0-60%) to afford the desired product (1.68 g, 84.8%). LCMS cacld. for $C_{15}H_{22}BN_4O_4$ $(M-55)^+$: m/z=333.2. Found: 333.1.

Step 3: {3-[4-(4,4,5,5-Tetramethyl-1,3,2-dioxaborolan-2-yl)-1H-pyrazol-1-yl]azetidin-3-yl}acetonitrile hydrochloride

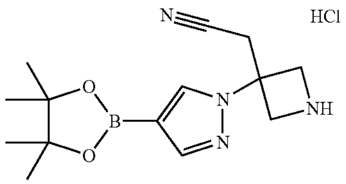 [SMILES: CC1(C)OB(c2cnn(C3(CC#N)CNC3)c2)OC1(C)C ; Cl]

4.0 N HCl in 1,4-dioxane (2.0 mL) was added to solution of tert-butyl 3-(cyanomethyl)-3-[4-(4,4,5,5-tetramethyl-1,3,2-dioxaborolan-2-yl)-1H-pyrazol-1-yl]azetidine-1-carboxylate (1.68 g, 4.33 mmol) in methylene chloride (10 mL). The reaction mixture was stirred at room temperature overnight, and then concentrated under reduced pressure to afford the desired product as HCl salt which was directly used in the next step reaction without further purification. LCMS cacld. for $C_{14}H_{22}BN_4O_2$ $(M+1)^+$: m/z=289.2. Found: 289.1.

Step 4: 5-Chloro-N-[(1S)-2,2,2-trifluoro-1-methylethyl]pyrazine-2-carboxamide

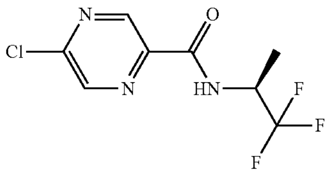 [SMILES: C[C@H](NC(=O)c1cnc(Cl)cn1)C(F)(F)F]

N,N-Diisopropylethylamine (1.3 mL, 7.5 mmol) was added to a mixture of 5-chloropyrazine-2-carboxylic acid (0.40 g, 2.5 mmol), N,N,N',N'-tetramethyl-O-(7-azabenzotriazol-1-yl)uronium hexafluorophosphate (1.0 g, 2.8 mmol) and (2S)-1,1,1-trifluoropropan-2-amine (0.28 g, 2.5 mmol) in methylene chloride (10 mL). The reaction mixture was stirred at room temperature overnight. The reaction mixture was worked up with sat. aqueous $NaHCO_3$, and extracted with ethyl acetate. The combined organic layers were washed with brine, dried over $MgSO_4$, filtered and concentrated under reduced pressure. The residue was purified by flash chromatography on a silica gel column with ethyl acetate in hexanes (0-15%) to afford the desired product (0.47 g, 73%). LCMS cacld. for $C_8H_8ClF_3N_3O$ $(M+1)^+$: m/z=254.0. Found: 253.9.

Step 5: 5-{3-(Cyanomethyl)-3-[4-(4,4,5,5-tetramethyl-1,3,2-dioxaborolan-2-yl)-1H-pyrazol-1-yl]azetidin-1-yl}-N-[(1S)-2,2,2-trifluoro-1-methylethyl]pyrazine-2-carboxamide

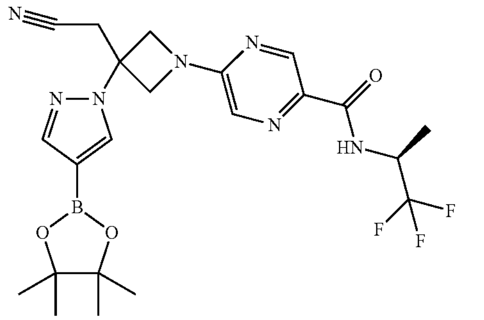 [SMILES: C[C@H](NC(=O)c1cnc(N2CC(CC#N)(n3cc(B4OC(C)(C)C(C)(C)O4)cn3)C2)cn1)C(F)(F)F]

A mixture of 5-chloro-N-[(1S)-2,2,2-trifluoro-1-methylethyl]pyrazine-2-carboxamide (254 mg, 1.00 mmol), {3-[4-(4,4,5,5-tetramethyl-1,3,2-dioxaborolan-2-yl)-1H-pyrazol-1-yl]azetidin-3-yl}acetonitrile HCl salt (325 mg, 1.00 mmol) and N,N-diisopropylethylamine (401 μL, 2.30 mmol) in 1,4-dioxane (5.0 mL) was heated at 100° C. for 2 h. After cooling, the mixture was concentrated under reduced pressure. The residue was purified by flash chromatography on a silica gel column eluting with ethyl acetate in hexane (gradient: 20-80%) to afford the desired product (0.49 g, 97%). LCMS cacld. for $C_{22}H_{28}BF_3N_7O_3$ $(M+1)^+$: m/z=506.2. Found: 506.1.

Step 6: tert-Butyl 4-bromo-3-methyl-1H-pyrazole-1-carboxylate

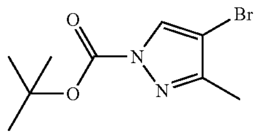

A mixture of 4-bromo-3-methyl-1H-pyrazole (0.2 g, 1 mmol), di-tert-butyldicarbonate (0.30 g, 1.4 mmol), 4-dimethylaminopyridine (0.02 g, 0.1 mmol) and triethylamine (0.26 mL, 1.9 mmol) in acetonitrile (2 mL) was stirred at rt overnight. The reaction mixture was concentrated, and purified by flash chromatography on a silica gel column eluting with ethyl acetate in hexanes (0-15%) to afford the desired product (0.32 g). LCMS cacld. for $C_5H_6BrN_2O_2$ $(M-55)^+$: m/z=205.0. Found: 204.9.

Step 7: 5-[3-(Cyanomethyl)-3-(3'-methyl-1H,1'H-4,4'-bipyrazol-1-yl)azetidin-1-yl]-N-[(1S)-2,2,2-trifluoro-1-methylethyl]pyrazine-2-carboxamide trifluoroacetate A mixture of 5-{3-(cyanomethyl)-3-[4-(4,4,5,5-tetramethyl-1,3,2-dioxaborolan-2-yl)-1H-pyrazol-1-yl]azetidin-1-yl}-N-[(1S)-2,2,2-trifluoro-1-methylethyl]pyrazine-2-carboxamide (27.0 mg, 0.0533 mmol), tert-butyl 4-bromo-3-methyl-1H-pyrazole-1-carboxylate (15 mg, 0.059 mmol), tetrakis(triphenylphosphine)palladium(0) (3.1 mg, 0.0027 mmol) and sodium carbonate (17.0 mg, 0.160 mmol) in 1,4-dioxane (1.6 mL) and water (0.8 mL) under nitrogen was stirred at 100° C. overnight. The reaction mixture was filtered, and purified by RP-HPLC (pH=2 conditions) to afford the desired product as TFA salt. $^1H$ NMR (300 MHz, $CD_3OD$) δ 8.73 (d, J=1.4 Hz, 1H), 8.18 (d, J=0.6 Hz, 1H), 7.98 (d, J=1.4 Hz, 1H), 7.91-7.79 (m, 2H), 4.84 (m, 1H), 4.81 (d, J=10.2 Hz, 2H), 4.60 (d, J=10.2 Hz, 2H), 3.59 (s, 2H), 2.44 (s, 3H), 1.43 (d, J=7.1 Hz, 3H) ppm. LCMS cacld. for $C_{20}H_{21}F_3N_9O$ $(M+1)^+$: m/z=460.2. Found: 460.0.

Example 2

5-[3-(Cyanomethyl)-3-(3'-methyl-1H,1'H-4,4'-bipyrazol-1-yl)azetidin-1-yl]-N-isopropylpyrazine-2-carboxamide trifluoroacetate

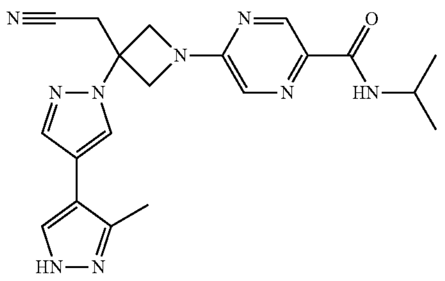 [SMILES: Cc1n[nH]cc1-c1cnn(C2(CC#N)CN(c3cnc(C(=O)NC(C)C)cn3)C2)c1]

Step 1: 5-Chloro-N-isopropylpyrazine-2-carboxamide

N,N-Diisopropylethylamine (2.6 mL, 15 mmol) was added to a mixture of 5-chloropyrazine-2-carboxylic acid (0.80 g, 5.0 mmol), benzotriazol-1-yloxytris(dimethylamino)phosphonium hexafluorophosphate (2.46 g, 5.56 mmol) and 2-propanamine (0.47 mL, 5.6 mmol) in methylene chloride (20 mL). The reaction mixture was stirred at room temperature overnight. The reaction mixture was worked up with sat. aqueous $NaHCO_3$, and extracted with ethyl acetate. The combined organic layers were washed with brine, dried over $MgSO_4$, filtered and concentrated under reduced pressure. The residue was purified by flash chromatography on a silica gel column eluting with ethyl acetate in hexanes (0-15%) to afford the desired product. LCMS cacld. for $C_8H_{11}ClN_3O$ $(M+1)^+$: m/z=200.1. Found: 200.1.

Step 2: 5-{3-(Cyanomethyl)-3-[4-(4,4,5,5-tetramethyl-1,3,2-dioxaborolan-2-yl)-1H-pyrazol-1-yl]azetidin-1-yl}-N-isopropylpyrazine-2-carboxamide A mixture of 5-chloro-N-isopropylpyrazine-2-carboxamide (200 mg, 1.00 mmol), {3-[4-(4,4,5,5-tetramethyl-1,3,2-dioxaborolan-2-yl)-1H-pyrazol-1-yl]azetidin-3-yl}acetonitrile HCl salt (325 mg, 1.00 mmol, from Example 1, step 3) and N,N-diisopropylethylamine (401 μL, 2.30 mmol) in 1,4-dioxane (5.0 mL) was heated at 100° C. for 2 h. After cooling, the mixture was concentrated under reduced pressure. The residue was purified by flash chromatography on a silica gel column eluting with ethyl acetate in hexane (gradient: 20-80%) to afford the desired product (0.26 g, 58%). LCMS cacld. for $C_{22}H_{31}BN_7O_3$ $(M+1)^+$: m/z=452.3. Found: 452.2.

Step 3: 5-[3-(Cyanomethyl)-3-(3'-methyl-1H,1H'-4,4'-bipyrazol-1-yl)azetidin-1-yl]-N-isopropylpyrazine-2-carboxamide trifluoroacetate A mixture of tert-butyl 4-bromo-3-methyl-1H-pyrazole-1-carboxylate (15.7 mg, 0.0600 mmol), 5-{3-(cyanomethyl)-3-[4-(4,4,5,5-tetramethyl-1,3,2-dioxaborolan-2-yl)-1H-pyrazol-1-yl]azetidin-1-yl}-N-isopropylpyrazine-2-carboxamide (25.8 mg, 0.0571 mmol), [1,1'-bis(diphenylphosphino)ferrocene]dichloropalladium(II) complex with dichloromethane (1:1) (2.3 mg, 0.0028 mmol) and potassium phosphate (0.036 g, 0.17 mmol) in dioxane (0.5 mL) and water (0.2 mL) in a reaction vial was degassed and sealed. The mixture was heated at 110° C. for 3 h. After cooling, the mixture was diluted with methanol, filtered and purified by RP-HPLC (pH=2 conditions) to afford the desired product as TFA salt. LCMS cacld. for $C_{20}H_{24}N_9O$ $(M+1)^+$: m/z=406.2. Found: 406.1.

Example 3

4-[3-(Cyanomethyl)-3-(3'-methyl-1H,1'H-4,4'-bipyrazol-1-yl)azetidin-1-yl]-N-isopropylbenzamide trifluoroacetate

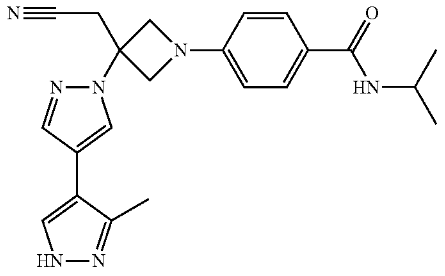 [SMILES: Cc1n[nH]cc1-c1cnn(C2(CC#N)CN(c3ccc(C(=O)NC(C)C)cc3)C2)c1]

Step 1: Ethyl 4-(3-hydroxyazetidine-1-yl)benzoate

A mixture of ethyl 4-fluorobenzoate (0.841 g, 5.00 mmol, from Aldrich), azetidin-3-ol hydrochloride (0.438 g, 4.00 mmol, from Aldrich) and potassium carbonate (1.38 g, 9.98 mmol) in dimethyl sulfoxide (4 mL) was heated at 180° C. for 2 h. After cooling, the mixture was diluted with ethyl acetate (50 mL), and washed with water and brine. The organic layer was dried over $MgSO_4$, filtered, and concentrated under reduced pressure. The residue was purified by flash chromatography on a silica gel column with ethyl acetate in hexane (0-50%) to afford the desired product (0.643, 72.6%). LCMS cacld. for $C_{12}H_{16}NO_3$ $(M+1)^+$: m/z=222.1. Found: 222.1.

Step 2: 4-(3-Hydroxyazetidin-1-yl)benzoic acid

A mixture of 1-[4-(3-hydroxyazetidin-1-yl)phenyl]-2-methoxyethanone (1.33 g, 6.00 mmol) and lithium hydroxide monohydrate (504 mg, 12.0 mmol) in water (4 mL), methanol (3 mL) and THF (6 mL) was stirred at 40° C. overnight. The mixture was neutralized with 3 N HCl aqueous solution (~4 mL) to pH about 7, extracted with ethyl acetate. The combined organic layers were dried over $Na_2SO_4$, filtered and concentrated under reduced pressure to afford the crude product (1.10 g, 94.9%) which was directly used in the next step without further purification. LCMS cacld. for $C_{10}H_{12}NO_3$ $(M+1)^+$: m/z=194.1. Found: 194.1.

Step 3: 4-(3-Hydroxyazetidin-1-yl)-N-isopropylbenzamide

Benzotriazol-1-yloxytris(dimethylamino)phosphonium hexafluorophosphate (4.64 g, 10.5 mmol, from Aldrich) was added to a mixture of 4-(3-hydroxyazetidin-1-yl)benzoic acid (1.93 g, 10.0 mmol), 2-propanamine (4.26 mL, 50.0 mmol) and N,N-diisopropylethylamine (3.88 g, 30.0 mmol) in dichloromethylene (10 mL). The mixture was stirred at room temperature for 2 h, and diluted with dichloromethane. The mixture was washed with aqueous $NaHCO_3$ and brine, dried over $Na_2SO_4$, filtered and concentrated under reduced pressure. The residue was purified by flash chromatography on a silica gel column eluting with ethyl acetate in hexane (gradient: 0-50%) to afford the desired product (2.21 g, 94.3%). LCMS cacld. for $C_{13}H_{19}N_2O_2$ $(M+1)^+$: m/z=235.1. Found: 235.1.

Step 4: N-Isopropyl-4-(3-oxoazetidin-1-yl)benzamide

To a cooled (−78° C.) solution of oxalyl chloride (1.05 mL, 12.4 mmol) in dichloromethylene (20 mL) was added dropwise dimethyl sulfoxide (1.71 mL, 24.1 mmol). The mixture was stirred at −78° C. for 10 min. Then a suspension of 4-(3-hydroxyazetidin-1-yl)-N-isopropylbenzamide (1.72 g, 7.34 mmol) in dichloromethylene (20 mL) was added. The mixture was stirred at −78° C. for 1 h, and then triethylamine (7.04 mL, 50.5 mmol) was added. The mixture was stirred at −78° C. for an additional 1.5 h. The mixture was washed with aq. $NaHCO_3$ and brine, dried over $Na_2SO_4$, filtered and concentrated under reduced pressure. The precipitates were washed with ether and collected by filtration to afford the desired product (1.32 g, 77%) which was directly used in the next step without further purification. LCMS cacld. for $C_{13}H_{17}N_2O_2$ $(M+1)^+$: m/z=233.1. Found: 233.1.

Step 5: 4-[3-(Cyanomethylene)azetidin-1-yl]-N-isopropylbenzamide

To a cooled (at −6-0° C.) solution of 1.0 M potassium tert-butoxide in tetrahydrofuran (7.10 mL, 7.10 mmol) was added dropwise a solution of diethyl cyanomethylphosphonate (1.20 mL, 7.43 mmol, from Aldrich) in tetrahydrofuran (10 mL) over a period of 10 min and at −6 to 0° C. The reaction was warmed and stirred at room temperature for 1 h. The reaction mixture was cooled at −6° C. again. To the reaction mixture was then added a solution of N-isopropyl-4-(3-oxoazetidin-1-yl)benzamide (1.30 g, 5.60 mmol) in tetrahydrofuran (10 mL) over a period of 10 min. During this time the temperature of the reaction mixture was between −5 to 0° C. The reaction was allowed to warm to room temperature and was stirred for 3 h. The reaction mixture was filtered through a pad of silica gel and washed with ethyl acetate. The filtrate was concentrated, and the residue was treated with ether. The precipitates formed were collected by filtration to give 0.60 g the desired product. The mother liquid was concentrated under reduced pressure. The residue was purified by flash chromatography on a silica gel column eluting with ethyl acetate in hexane (gradient: 30-80%) to afford the desired product (0.21 g). The total product is 0.81 g (57%). $^1H$ NMR (400 MHz, DMSO-$d_6$) δ 7.91 (d, J=7.8 Hz, 1H), 7.74 (d, J=8.7 Hz, 2H), 6.53 (d, J=8.7 Hz, 2H), 5.88 (p, J=2.3 Hz, 1H), 4.77-4.67 (m, 2H), 4.62 (dt, J=5.1, 2.6 Hz, 2H), 4.06 (m, 1H), 1.12 (d, J=6.6 Hz, 6H) ppm. LCMS cacld. for $C_{15}H_{18}N_3O$ $(M+1)^+$: m/z=256.1. Found: 256.1.

Step 6: 4-{3-(Cyanomethyl)-3-[4-(4,4,5,5-tetramethyl-1,3,2-dioxaborolan-2-yl)-1H-pyrazol-1-yl]azetidin-1-yl}-N-isopropylbenzamide A mixture of 4-(4,4,5,5-tetramethyl-1,3,2-dioxaborolan-2-yl)-1H-pyrazole (2.98 g, 15.3 mmol), 4-[3-(cyanomethylene)azetidin-1-yl]-N-isopropylbenzamide (4.00 g, 15.7 mmol) and 1,8-diazabicyclo[5.4.0]undec-7-ene (1.17 g, 7.68 mmol) in isopropyl alcohol (10 mL) was heated at 70° C. for 1 h. The mixture was cooled down to 35° C. To the suspension was added 30 ml of methyl tert-butyl ether (MTBE), and stirred at room temperature for 1 h. The precipitates formed was collected by filtration, washed with MTBE, and dried under reduced pressure to afford the desired product (6.2 g 89.8%). $^1$H NMR (400 MHz, DMSO-$d_6$) δ 8.35 (s, 1H), 7.90 (d, J=7.8 Hz, 1H), 7.75 (s, 1H), 7.73 (d, J=8.7 Hz, 2H), 6.52 (d, J=8.7 Hz, 2H), 4.40 (d, J=8.6 Hz, 2H), 4.20 (d, J=8.6 Hz, 2H), 4.05 (m, 1H), 3.65 (s, 2H), 1.24 (s, 12H), 1.12 (d, J=6.6 Hz, 6H) ppm. LCMS cacld. for $C_{24}H_{33}BN_5O_3$ $(M+1)^+$: m/z=450.3. Found: 450.3.

Step 7: 4-[3-(Cyanomethyl)-3-(3'-methyl-1H,1'H-4,4'-bipyrazol-1-yl)azetidin-1-yl]-N-isopropylbenzamide trifluoroacetate A mixture of tert-butyl 4-bromo-3-methyl-1H-pyrazole-1-carboxylate (15.7 mg, 0.0600 mmol), 4-{3-(cyanomethyl)-3-[4-(4,4,5,5-tetramethyl-1,3,2-dioxaborolan-2-yl)-1H-pyrazol-1-yl]azetidin-1-yl}-N-isopropylbenzamide (25.7 mg, 0.0571 mmol), potassium phosphate (36.4 mg, 0.171 mmol) and [1,1'-bis(diphenylphosphino)ferrocene]dichloropalladium(II) complex with dichloromethane (1:1) (2.33 mg, 0.00286 mmol) in dioxane (0.5 mL) and water (0.2 mL) in a reaction vial was degassed and sealed. The mixture was heated at 110° C. for 3 h. After cooling, the mixture was diluted with methanol, filtered and purified by RP-HPLC (pH=2 conditions) to afford the desired product as TFA salt. LCMS cacld. for $C_{22}H_{26}N_7O$ $(M+1)^+$: m/z=404.2. Found: 404.1.

Example 4

4-[3-(Cyanomethyl)-3-(3'-methyl-1H,1'H-4,4'-bipyrazol-1-yl)azetidin-1-yl]-2,5-difluoro-N-[(1S)-2,2,2-trifluoro-1-methylethyl]benzamide trifluoroacetate

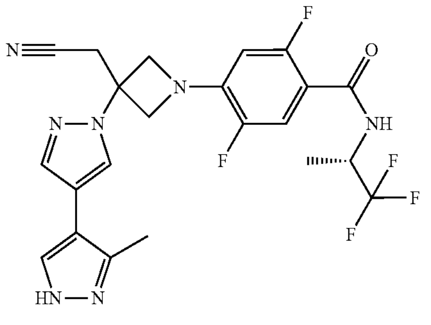 [SMILES: Cc1n[nH]cc1-c1cnn(C2(CC#N)CN(c3cc(F)c(C(=O)N[C@@H](C)C(F)(F)F)cc3F)C2)c1]

Step 1: 2,4,5-Trifluoro-N-[(1S)-2,2,2-trifluoro-1-methylethyl]benzamide

To a solution of 2,4,5-trifluorobenzoic acid (5.00 g, 28.4 mmol) in acetonitrile (50 mL) was added N,N-dimethylformamide (40 μL) followed by addition of oxalyl chloride (3.60 mL, 42.6 mmol). After 90 min, the volatiles were removed under reduced pressure. The residue was co-evaporated with acetonitrile (50 mL). The residue was then dissolved in methylene chloride (50 mL). This solution was added drop-wise into a cooled (ice bath) mixture of (2S)-1,1,1-trifluoropropan-2-amine hydrochloride (5.52 g, 36.9 mmol) (from Synquest, 98% ee) in toluene (100 mL) and 0.5 M sodium hydroxide aqueous solution (142 mL, 71.0 mmol). After addition, the ice bath was removed, and the reaction was allowed to warm to rt. The reaction was stirred overnight. The organic layer was separated. The aqueous layer was extracted with methylene chloride (50 mL). The combined organic layers were washed with 20% brine (75 mL) and water (2×75 mL), dried over $MgSO_4$, filtered and concentrated under reduced pressure to afford the desired product (6.49 g, 84%) which was directly used in the next step without further purification. $^1$H NMR (300 MHz, DMSO-$d_6$) δ 9.01 (d, J=7.6 Hz, 1H), 7.92-7.50 (m, 2H), 4.76 (m, 1H), 1.31 (d, J=7.0 Hz, 3H) ppm. LCMS cacld. for $C_{10}H_8F_6NO$ $(M+1)^+$: m/z=272.0. Found: 272.0.

Step 2: 2,5-Difluoro-4-(3-hydroxyazetidin-1-yl)-N-[(1S)-2,2,2-trifluoro-1-methylethyl]benzamide A mixture of 2,4,5-trifluoro-N-[(1S)-2,2,2-trifluoro-1-methylethyl]benzamide (6.39 g, 23.6 mmol), azetidin-3-ol hydrochloride (3.19 g, 28.3 mmol) and 1,8-diazabicyclo[5.4.0]undec-7-ene (8.81 mL, 58.9 mmol) in acetonitrile (25 mL) was stirred at 80° C. for 2 h. The reaction mixture was diluted with EtOAc (75 mL) and washed with 1N HCl (50 mL), 1N $NaHCO_3$ (60 mL), 20% brine (50 mL) and water (75 mL). The aqueous layers were extracted with EtOAc (100 mL). The organic layers were combined, dried over $MgSO_4$, filtered and concentrated under reduced pressure to yield the desired product (7.59 g, 91.8%). $^1$H NMR (300 MHz, DMSO-$d_6$) δ 8.38 (dd, J=8.9, 1.9 Hz, 1H), 7.27 (dd, J=12.8, 6.5 Hz, 1H), 6.38 (dd, J=12.3, 7.5 Hz, 1H), 5.71 (d, J=6.4 Hz, 1H), 4.74 (dp, J=15.3, 7.6 Hz, 1H), 4.62-4.46 (m, 1H), 4.30-4.15 (m, 2H), 3.71 (m, 2H), 1.29 (d, J=7.1 Hz, 3H) ppm. LCMS cacld. for $C_{13}H_{14}F_5N_2O_2$ $(M+1)^+$: m/z=325.1. Found: 325.1.

Step 3: 2,5-Difluoro-4-(3-oxoazetidin-1-yl)-N-[(1S)-2,2,2-trifluoro-1-methylethyl]benzamide To a solution of 2,5-difluoro-4-(3-hydroxyazetidin-1-yl)-N-[(1S)-2,2,2-trifluoro-1-methylethyl]benzamide (7.57 g, 23.3 mmol) in methylene chloride (93 mL) was added iodobenzene diacetate (9.40 g, 29.2 mmol) and 2,2,6,6-tetramethyl-1-piperidinyloxy free radical (1.82 g, 11.7 mmol) (TEMPO) at room temperature. The reaction mixture was stirred at room temperature overnight. The mixture was diluted with EtOAc (100 mL), washed with 0.5N $NaHCO_3$ (2×80 mL), 20% brine (100 mL) and water (100 mL). The aqueous layers were extracted with ethyl acetate (75 mL). The organic extracts were combined, dried over $MgSO_4$, filtered and concentrated under reduced pressure. The residue was purified by flash chromatography on a silica gel column eluting with 0% to 5% ethyl acetate in methylene chloride to afford the crude product which was recrystallized from MTBE (50 mL) and heptane (100 mL) to give the desired product (5.44 g, 72%) as colorless solid. $^1$H NMR (300 MHz, DMSO-$d_6$) δ 8.52 (d, J=8.0 Hz, 1H), 7.36 (dd, J=12.5, 6.5 Hz, 1H), 6.63 (dd, J=12.1, 7.6 Hz, 1H), 4.90 (d, J=2.1 Hz, 4H), 4.86-4.68 (m, 1H), 1.31 (d, J=7.1 Hz, 3H) ppm. LCMS cacld. for $C_{13}H_{12}F_5N_2O_2$ $(M+1)^+$: m/z=323.1. Found: 323.0.

Step 4: 4-[3-(Cyanomethylene)azetidin-1-yl]-2,5-difluoro-N-[(1S)-2,2,2-trifluoro-1-methylethyl]benzamide Diethyl cyanomethylphosphonate (1.95 mL, 11.8 mmol) was added drop-wise to a cooled (ice bath) solution of 1.0 M potassium tert-butoxide in THF (11.8 mL, 11.8 mmol) which was diluted with tetrahydrofuran (12 mL). The bath was removed and the reaction was warmed to room temperature, and stirred for 90 min. The reaction solution was cooled with an ice bath again. The above prepared solution was then added over 12 min to a cooled (ice-bath) solution of 2,5-difluoro-4-(3-oxoazetidin-1-yl)-N-[(1S)-2,2,2-trifluoro-1-methylethyl]benzamide (4.00 g, 12.4 mmol) in tetrahydrofuran (50 mL). The reaction mixture was stirred for 30 min. The ice bath was removed, and the reaction was stirred at room temperature overnight, then quenched by the addition of 20% brine (75 mL) and ethyl acetate (75 mL). The organic layer was separated. The aqueous layer was extracted with ethyl acetate (50 mL). The combined organic layers were dried over $MgSO_4$, filtered and concentrated under reduced pressure. The residue was purified by flash chromatography on a silica gel column with ethyl acetate in hexanes (0% to 30%) to yield the desired product (2.6 g). $^1H$ NMR (400 MHz, DMSO-$d_6$) δ 8.59-8.37 (m, 1H), 7.33 (dd, J=12.5, 6.4 Hz, 1H), 6.59 (dd, J=12.0, 7.4 Hz, 1H), 5.88 (m, 1H), 4.94-4.75 (m, 4H), 4.76 (m, 1H), 1.31 (d, J=7.1 Hz, 3H) ppm. LCMS cacld. for $C_{15}H_{13}F_5N_3O$ $(M+1)^+$: m/z=346.1. Found: 346.1.

Step 5: 4-{3-(Cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide A mixture of 4-(4,4,5,5-tetramethyl-1,3,2-dioxaborolan-2-yl)-1H-pyrazole (1.00 g, 5.15 mmol), 4-[3-(cyanomethylene)azetidin-1-yl]-2,5-difluoro-N-[(1S)-2,2,2-trifluoro-1-methylethyl]benzamide (1.78 g, 5.15 mmol) and 1,8-diazabicyclo[5.4.0]undec-7-ene (0.31 mL, 2.1 mmol) in acetonitrile (20.2 mL) was heated at 50° C. overnight. After cooling, the solvent was removed under reduced pressure. The residue was used in the next step without further purification. LCMS cacld. for $C_{24}H_{28}BF_5N_5O_3$ $(M+1)^+$: m/z=540.2. Found: 540.1.

Step 6: 4-[3-(Cyanomethyl)-3-(3'-methyl-1H,1'H-4,4'-bipyrazol-1-yl)azetidin-1-yl]-2,5-difluoro-N-[(1S)-2,2,2-trifluoro-1-methylethyl]benzamidetrifluoroacetate A mixture of 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide (28.8 mg, 0.0533 mmol), tert-butyl 4-bromo-5-methyl-1H-pyrazole-1-carboxylate (15 mg, 0.059 mmol), tetrakis(triphenylphosphine)palladium(0) (3.1 mg, 0.0027 mmol) and sodium carbonate (17.0 mg, 0.160 mmol) in 1,4-dioxane (1.6 mL) and water (0.8 mL) under nitrogen was stirred at 100° C. overnight. The reaction mixture was extracted with ethyl acetate. The combined organic layers were washed with brine, dried over $MgSO_4$, filtered and concentrated under reduced pressure. The residue was purified by RP-HPLC (pH=2 conditions) to afford the desired product as TFA salt. LCMS cacld. for $C_{22}H_{21}F_5N_7O$ $(M+1)^+$: m/z=494.2. Found: 494.0.

Example 5

4-[3-(1H,1'H-4,4'-Bipyrazol-1-yl)-3-(cyanomethyl)azetidin-1-yl]-2,5-difluoro-N-[(1S)-2,2,2-trifluoro-1-methylethyl]benzamide trifluoroacetate

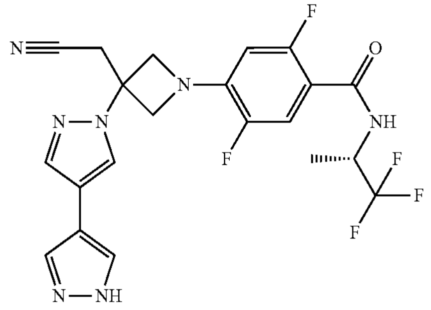 [SMILES: C[C@H](NC(=O)c1cc(F)c(N2CC(CC#N)(n3cc(-c4cn[nH]c4)cn3)C2)cc1F)C(F)(F)F]

This compound was prepared using procedures analogous to those described for the synthesis of Example 4, Step 6 starting from 4-bromo-1H-pyrazole and 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide. LCMS cacld. for $C_{21}H_{19}F_5N_7O$ $(M+1)^+$: m/z=480.2. Found: 480.0.

Example 6

5-[3-(Cyanomethyl)-3-(3,3'-dimethyl-1H,1'H-4,4'-bipyrazol-1-yl)azetidin-1-yl]-N-isopropylpyrazine-2-carboxamide trifluoroacetate

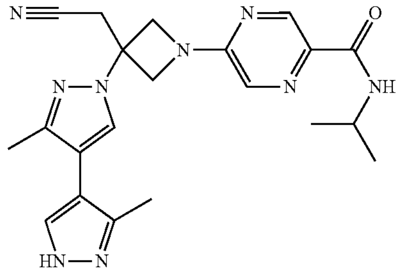 [SMILES: Cc1n[nH]cc1-c1cn(C2(CC#N)CN(c3cnc(C(=O)NC(C)C)cn3)C2)nc1C]

Step 1: tert-Butyl 3-(cyanomethyl)-3-[3-methyl-4-(4,4,5,5-tetramethyl-1,3,2-dioxaborolan-2-yl)-1H-pyrazol-1-yl]azetidine-1-carboxylate A mixture of 3-methyl-4-(4,4,5,5-tetramethyl-1,3,2-dioxaborolan-2-yl)-1H-pyrazole (1.06 g, 5.10 mmol), tert-butyl 3-(cyanomethylene)azetidine-1-carboxylate (1.00 g, 5.15 mmol) and 1,8-diazabicyclo[5.4.0]undec-7-ene (0.38 mL, 2.6 mmol) in acetonitrile (20 mL) was heated at 60° C. for 2 h. After cooling, the solvent was removed under reduced pressure. The residue was purified by flash chromatography on a silica gel column eluting with ethyl acetate in hexanes (0-60%) to afford the desired product. LCMS cacld. for $C_{16}H_{24}BN_4O_4$ $(M-55)^+$: m/z=347.2. Found: 347.1.

Step 2: {3-[3-Methyl-4-(4,4,5,5-tetramethyl-1,3,2-dioxaborolan-2-yl)-1H-pyrazol-1-yl]azetidin-3-yl}acetonitrile hydrochloride 4.0 N HCl in dioxane (3 mL) was added to a solution of tert-butyl 3-(cyanomethyl)-3-[3-methyl-4-(4,4,5,5-tetramethyl-1,3,2-dioxaborolan-2-yl)-1H-pyrazol-1-yl]azetidine-1-carboxylate in methylene chloride (10 mL). The reaction mixture was stirred at room temperature overnight. The mixture was concentrated under reduced pressure to afford the crude product as HCl salt. LCMS cacld. for $C_{15}H_{24}BN_4O_2$ $(M+1)^+$: m/z=303.2. Found: 303.1.

Step 3: 5-{3-(Cyanomethyl)-3-[3-methyl-4-(4,4,5,5-tetramethyl-1,3,2-dioxaborolan-2-yl)-1H-pyrazol-1-yl]azetidin-1-yl}-N-isopropylpyrazine-2-carboxamide A mixture of {3-[3-methyl-4-(4,4,5,5-tetramethyl-1,3,2-dioxaborolan-2-yl)-1H-pyrazol-1-yl]azetidin-3-yl}acetonitrile HCl salt (0.43 g, 1.3 mmol), 5-chloro-N-isopropylpyrazine-2-carboxamide (0.24 g, 1.2 mmol) and N,N-diisopropylethylamine (0.63 mL, 3.6 mmol) in tert-butyl alcohol (12 mL, 120 mmol) was heated at 100° C. for 4 h. After cooling, the solvent was removed under reduced pressure. The residue was purified by flash chromatography on a silica gel column eluting with ethyl acetate in hexanes (0-60%) to afford the desired product. LCMS cacld. for $C_{23}H_{33}BN_7O_3$ $(M+1)^+$: m/z=466.3. Found: 466.2.

Step 4: 5-[3-(Cyanomethyl)-3-(3,3'-dimethyl-1H,1'H-4,4'-bipyrazol-1-yl)azetidin-1-yl]-N-isopropylpyrazine-2-carboxamide trifluoroacetate This compound was prepared using procedures analogous to those described for the synthesis of Example 4, Step 6 starting from 4-bromo-3-methyl-1H-pyrazole and 5-{3-(cyanomethyl)-3-[3-methyl-4-(4,4,5,5-tetramethyl-1,3,2-dioxaborolan-2-yl)-1H-pyrazol-1-yl]azetidin-1-yl}-N-isopropylpyrazine-2-carboxamide. LCMS cacld. for $C_{21}H_{26}N_9O$ $(M+1)^+$: m/z=420.2. Found: 420.1.

Example 7

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide

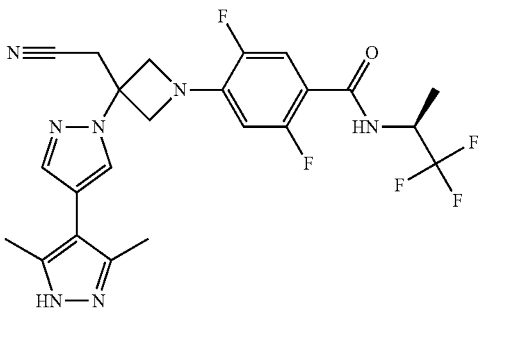 [SMILES: Cc1n[nH]c(C)c1-c1cnn(C2(CC#N)CN(c3cc(F)c(C(=O)N[C@@H](C)C(F)(F)F)cc3F)C2)c1]

A mixture of 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide (329 mg, 0.610 mmol, from Example 4, step 5), 4-bromo-3,5-dimethyl-1H-pyrazole (206 mg, 1.18 mmol), tetrakis(triphenylphosphine)palladium(0) (110 mg, 0.098 mmol) and sodium carbonate (320 mg, 3.0 mmol) in 1,4-dioxane (10 mL)/water (5 mL) was purged with nitrogen and stirred at 110° C. for 1 h. The reaction mixture was diluted with EtOAc, washed with water and brine, concentrated. The residue was purified first with silica gel (eluting with 0-100% EtOAc/hexanes followed by 10% methanol/dichloromethane), and then by prep-LCMS (XBridge C18 column, eluting with a gradient of acetonitrile/water containing 0.1% ammonium hydroxide, at flow rate of 60 mL/min) to give the desired product (30 mg, 9.7%). $^1H$ NMR (500 MHz, DMSO-$d_6$) δ 12.17 (1H, s), 8.45 (1H, d, J=8.0 Hz), 8.10 (1H, s), 7.70 (1H, s), 7.34 (1H, m), 6.61 (1H, s), 4.77 (1H, m), 4.62 (2H, d, J=9.0 Hz), 4.39 (1H, d, J=9.0 Hz), 3.64 (2H, s), 2.22 (6H, s), 1.31 (6H, d, J=7.0 Hz) ppm. LCMS calculated for $C_{23}H_{23}F_5N_7O$ $(M+H)^+$: m/z=508.2. Found: 508.0.

Example 8

5-[3-(Cyanomethyl)-3-(3',5'-dimethyl-1H,1'H-4,4'-bipyrazol-1-yl)azetidin-1-yl]-N-isopropylpyrazine-2-carboxamide

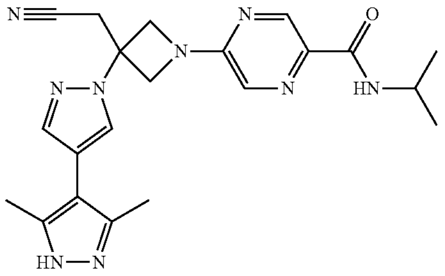 [SMILES: Cc1n[nH]c(C)c1-c1cnn(C2(CC#N)CN(c3cnc(C(=O)NC(C)C)cn3)C2)c1]

A mixture of 5-{3-(cyanomethyl)-3-[4-(4,4,5,5-tetramethyl-1,3,2-dioxaborolan-2-yl)-1H-pyrazol-1-yl]azetidin-1-yl}-N-isopropylpyrazine-2-carboxamide (256 mg, 0.567 mmol, from Example 2, step 2), 4-bromo-3,5-dimethyl-1H-pyrazole (119 mg, 0.681 mmol), dicyclohexyl(2',4',6'-triisopropylbiphenyl-2-yl)phosphine-(2'-aminobiphenyl-2-yl)(chloro)palladium (1:1) (67 mg, 0.085 mmol) and cesium carbonate (550 mg, 1.7 mmol) in 1,4-dioxane (2 mL)/water (1 mL) was purged with nitrogen three times. The reaction was heated to 53° C. for 2 h. The mixture was diluted with EtOAc, washed with brine, concentrated. The resulting reside was purified first on silica gel (eluting with 0-100% EtOAc/hexanes followed by 10% methanol/dichloromethane), and then by prep-LCMS (XBridge C18 column, eluting with a gradient of acetonitrile/water containing 0.1% ammonium hydroxide, at flow rate of 60 mL/min) to give the desired product (0.1 g, 40%). $^1H$ NMR (500 MHz, DMSO-$d_6$) δ 8.64 (1H, d, J=1.5 Hz), 8.12 (1H, s), 8.06 (1H, d, J=8.0 Hz), 7.96 (1H, d, J=1.0 Hz), 7.71 (1H, s), 4.72 (2H, d, J=9.5 Hz), 4.49 (1H, d, J=9.5 Hz), 4.08 (1H, m), 3.68 (2H, s), 2.22 (6H, s), 1.16 (6H, d, J=6.5 Hz) ppm. LCMS calculated for $C_{21}H_{26}N_9O$ $(M+H)^+$: m/z=420.2. Found: 420.0.

Example 9

5-[3-(Cyanomethyl)-3-(3',5'-dimethyl-1H,1'H-4,4'-bipyrazol-1-yl)azetidin-1-yl]-N-[(1S)-2,2,2-trifluoro-1-methylethyl]pyrazine-2-carboxamide trifluoroacetate

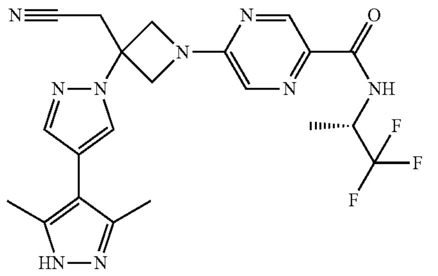 [SMILES: Cc1n[nH]c(C)c1-c1cnn(C2(CC#N)CN(c3cnc(C(=O)N[C@@H](C)C(F)(F)F)cn3)C2)c1]

Step 1. [3-(3',5'-Dimethyl-1H,1'H-4,4'-bipyrazol-1-yl)azetidin-3-yl]acetonitrile hydrochloride A mixture of tert-butyl 3-(cyanomethyl)-3-[4-(4,4,5,5-tetramethyl-1,3,2-dioxaborolan-2-yl)-1H-pyrazol-1-yl]azetidine-1-carboxylate (381 mg, 0.981 mmol, from Example 1, step 2), 4-bromo-3,5-dimethyl-1H-pyrazole (206 mg, 1.18 mmol), tetrakis(triphenylphosphine)palladium(0) (110 mg, 0.098 mmol) and sodium carbonate (310 mg, 2.9 mmol) in 1,4-dioxane (10 mL) and water (5 mL) was purged with $N_2$ and stirred at 110° C. for 2 h. The reaction mixture was filtered, diluted with EtOAc, then washed with water. The organic layer was concentrated and purified on silica gel (eluting with 0-100% EtOAc/hexanes followed by 0-10% MeOH/dichloromethane) to give tert-butyl 3-(cyanomethyl)-3-(3',5'-dimethyl-1H,1'H-4,4'-bipyrazol-1-yl)azetidine-1-carboxylate (90 mg, 26%). LCMS calculated for $C_{18}H_{25}N_6O_2$ $(M+H)^+$: m/z=357.2. Found: 357.2. This intermediate was treated with 4.0 M hydrogen chloride in dioxane (1.2 mL, 4.9 mmol) in methylene chloride (1 mL) at rt for 2 h. The mixture was stripped to dryness to give the desired product. LCMS calculated for $C_{13}H_{17}N_6$ $(M+H)^+$: m/z=257.1. Found: 257.1.

Step 2. 5-[3-(Cyanomethyl)-3-(3',5'-dimethyl-1H,1'H-4,4'-bipyrazol-1-yl)azetidin-1-yl]-N-[(1S)-2,2,2-trifluoro-1-methylethyl]pyrazine-2-carboxamide trifluoroacetate A mixture of [3-(3',5'-dimethyl-1H,1'H-4,4'-bipyrazol-1-yl)azetidin-3-yl]acetonitrile hydrochloride (13 mg, 0.039 mmol), 5-chloro-N-[(1S)-2,2,2-trifluoro-1-methylethyl]pyrazine-2-carboxamide (11 mg, 0.043 mmol, from Example 1, step 4) and N,N-diisopropylethylamine (28 μL, 0.16 mmol) in tert-butyl alcohol (1 mL) was heated at 100° C. for 2 h. After cooling, the mixture was diluted with MeOH and purified on prep-LCMS (pH=2 conditions) to give the desired producer as TFA salt (4.1 mg, 22%). LCMS calculated for $C_{21}H_{23}F_3N_9O$ $(M+H)^+$: m/z=474.2. Found: 474.0.

Example 10

5-[3-(Cyanomethyl)-3-(3-methyl-1H,1'H-4,4'-bipyrazol-1-yl)azetidin-1-yl]-N-isopropylpyrazine-2-carboxamide trifluoroacetate

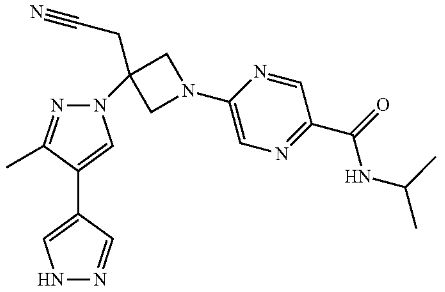 [SMILES: Cc1nn(C2(CC#N)CN(c3cnc(C(=O)NC(C)C)cn3)C2)cc1-c1cn[nH]c1]

Step 1: tert-Butyl 4-bromo-1H-pyrazole-1-carboxylate

This compound was prepared by using procedures analogous to those described for the synthesis of Example 1, Step 6 starting from 4-bromo-1H-pyrazole. LCMS calculated for $C_4H_4BrN_2O_2$ $(M-55)^+$: m/z=191.0. Found: 190.9.

Step 2: 5-[3-(Cyanomethyl)-3-(3-methyl-1H,1'H-4,4'-bipyrazol-1-yl)azetidin-1-yl]-N-isopropylpyrazine-2-carboxamide trifluoroacetate This compound was prepared as TFA salt by using procedures analogous to those described for the synthesis of Example 4, Step 6 starting from tert-butyl 4-bromo-1H-pyrazole-1-carboxylate and 5-{3-(cyanomethyl)-3-[3-methyl-4-(4,4,5,5-tetramethyl-1,3,2-dioxaborolan-2-yl)-1H-pyrazol-1-yl]azetidin-1-yl}-N-isopropylpyrazine-2-carboxamide. LCMS calculated for $C_{20}H_{24}N_9O$ $(M+1)^+$: m/z=406.2. Found: 406.1.

Example 11

5-[3-(Cyanomethyl)-3-(3'-ethyl-1H,1'H-4,4'-bipyrazol-1-yl)azetidin-1-yl]-N-[(1S)-2,2,2-trifluoro-1-methylethyl]pyrazine-2-carboxamide trifluoroacetate

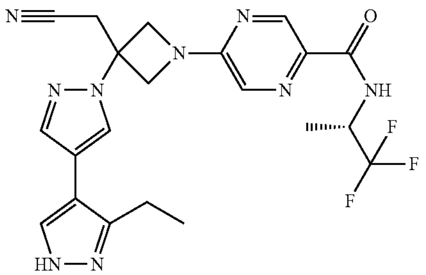 [SMILES: CCc1n[nH]cc1-c1cnn(C2(CC#N)CN(c3cnc(C(=O)N[C@@H](C)C(F)(F)F)cn3)C2)c1]

This compound was prepared as TFA salt by using procedures analogous to those described for the synthesis of Example 4, Step 6 starting from 5-{3-(cyanomethyl)-3-[4-(4,4,5,5-tetramethyl-1,3,2-dioxaborolan-2-yl)-1H-pyrazol-1-yl]azetidin-1-yl}-N-[(1S)-2,2,2-trifluoro-1-methylethyl]pyrazine-2-carboxamide (Example 1, Step 5) and 4-bromo-3-ethyl-1H-pyrazole. LCMS calculated for $C_{21}H_{23}F_3N_9O$ $(M+1)^+$: m/z=474.2. Found: 474.0.

Example 12

4-{3-(Cyanomethyl)-3-[3'-(hydroxymethyl)-1H,1'H-4,4'-bipyrazol-1-yl]azetidin-1-yl}-2,5-difluoro-N-[(1S)-2,2,2-trifluoro-1-methylethyl]benzamide trifluoroacetate

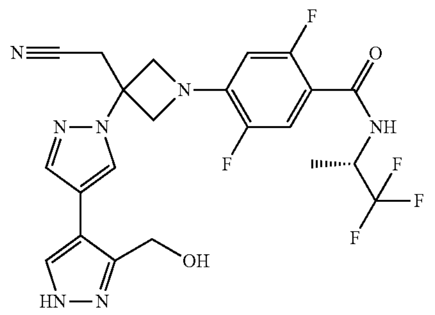 [SMILES: C[C@H](NC(=O)c1cc(F)c(N2CC(CC#N)(n3cc(-c4c[nH]nc4CO)cn3)C2)cc1F)C(F)(F)F]

Step 1: (4-Bromo-1H-pyrazol-5-yl)methanol

Sodium tetrahydroborate (0.13 g, 3.4 mmol) was added to a solution of 4-bromo-1H-pyrazole-5-carbaldehyde (0.30 g, 1.7 mmol, from Maybridge) in tetrahydrofuran (5 mL). The reaction mixture was stirred at 50° C. for 1 h. The reaction mixture was quenched with saturated aqueous $NaHCO_3$, and extracted with ethyl acetate (3×20 mL). The combined organic layers were washed with brine, dried over $MgSO_4$, filtered and concentrated under reduced pressure to afford the crude product which was directly used in the next step reaction without further purification. LCMS calculated for $C_4H_6BrN_2O$ $(M+1)^+$: m/z=177.0. Found: 176.9.

Step 2: 4-{3-(Cyanomethyl)-3-[3'-(hydroxymethyl)-1H,1'H-4,4'-bipyrazol-1-yl]azetidin-1-yl}-2,5-difluoro-N-[(1S)-2,2,2-trifluoro-1-methylethyl]benzamide trifluoroacetate This compound was prepared as TFA salt by using procedures analogous to those described for the synthesis of Example 4, Step 6 starting from 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide and (4-bromo-1H-pyrazol-3-yl) methanol. LCMS calculated for $C_{22}H_{21}F_5N_7O_2$ $(M+1)^+$: m/z=510.2. Found: 510.0.

Example 13

4-{3-(Cyanomethyl)-3-[3-(hydroxymethyl)-3'-methyl-1H,1'H-4,4'-bipyrazol-1-yl]azetidin-1-yl}-2,5-difluoro-N-[(1S)-2,2,2-trifluoro-1-methylethyl]benzamide

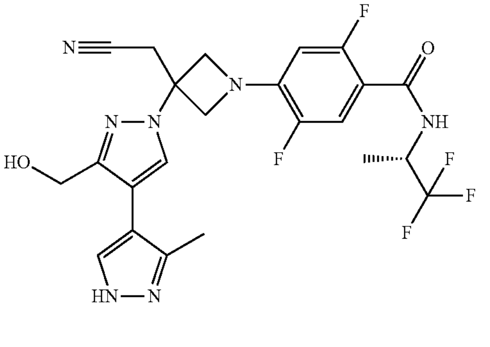 [SMILES: Cc1n[nH]cc1-c1cn(C2(CC#N)CN(c3cc(F)c(C(=O)N[C@@H](C)C(F)(F)F)cc3F)C2)nc1CO]

Step 1. Ethyl 4-bromo-1-{3-(cyanomethyl)-1-[2,5-difluoro-4-({[(1S)-2,2,2-trifluoro-1-methylethyl]amino}carbonyl)phenyl]azetidin-3-yl}-1H-pyrazole-3-carboxylate To a microwave vial was added isopropyl alcohol (10 mL), ethyl 4-bromo-1H-pyrazole-3-carboxylate (from ChemBridge) (788 mg, 3.60 mmol), 1,8-diazabicyclo[5.4.0]undec-7-ene (48.9 μL, 0.327 mmol) and 4-[3-(cyanomethylene)azetidin-1-yl]-2,5-difluoro-N-[(1S)-2,2,2-trifluoro-1-methylethyl]benzamide (from Example 4 step 4, 1.13 g, 3.27 mmol). The reaction mixture was stirred at 80° C. for 2 h. After cooling to room temperature, the solvent was removed in vacuo. The residue was purified with flash chromatography (eluting with 0-35% ethyl acetate in hexanes) to give the desired product as white foam. $^1H$ NMR (500 MHz, DMSO) δ 8.61 (s, 1H), 8.47 (d, J=8.7 Hz, 1H), 7.34 (dd, J=12.5 and 6.3 Hz, 1H), 6.62 (dd, J=11.9 and 7.3 Hz, 1H), 4.76 (dt, J=15.5 and 7.8 Hz, 1H), 4.61 (d, J=9.2 Hz, 2H), 4.39 (d, J=8.0 Hz, 2H), 4.32 (q, J=7.1 Hz, 2H), 3.68 (s, 2H), 1.31 (m, 6H) ppm. LCMS calculated for $C_{21}H_{20}BrF_5N_5O_3$ $(M+H)^+$: m/z=564.1. Found: 563.8.

Step 2. Ethyl 1-{3-(cyanomethyl)-1-[2,5-difluoro-4-({[(1S)-2,2,2-trifluoro-1-methylethyl]amino}carbonyl)phenyl]azetidin-3-yl}-3'-methyl-1H,1'H-4,4'-bipyrazole-3-carboxylate To a microwave vial were charged with tert-butyl alcohol (1.2 mL), and water (1.2 mL), cesium fluoride (683 mg, 4.50 mmol), ethyl 4-bromo-1-{3-(cyanomethyl)-1-[2,5-difluoro-4-({[(1S)-2,2,2-trifluoro-1-methylethyl]amino}carbonyl)phenyl]azetidin-3-yl}-1H-pyrazole-3-carboxylate (725 mg, 1.28 mmol) and 3-methyl-4-(4,4,5,5-tetramethyl-1,3,2-dioxaborolan-2-yl)-1H-pyrazole (401 mg, 1.93 mmol), followed by Pd-127 (49 mg, 0.064 mmol) (from Johnson Mathew). The reaction mixture was heated at 85° C. for 48 h. The reaction was cooled to room temperature, diluted with water and ethyl acetate. The aqueous layer was extracted with ethyl acetate. The organic layer was dried over $Na_2SO_4$, concentrated. The resulting residue was purified with flash chromatography (eluting with 30-100% ethyl acetate in hexanes) to give the desired product as an oil. LCMS calculated for $C_{25}H_{25}F_5N_7O_3$ $(M+H)^+$: m/z=566.2. Found: 566.0.

Step 3. 4-{3-(Cyanomethyl)-3-[3-(hydroxymethyl)-3'-methyl-1H,1'H-4,4'-bipyrazol-1-yl]azetidin-1-yl}-2,5-difluoro-N-[(1S)-2,2,2-trifluoro-1-methylethyl]benzamide To a solution of ethyl 1-{3-(cyanomethyl)-1-[2,5-difluoro-4-({[(1S)-2,2,2-trifluoro-1-methylethyl]amino}carbonyl)phenyl]azetidin-3-yl}-3'-methyl-1H,1'H-4,4'-bipyrazole-3-carboxylate (35 mg, 0.062 mmol) in THF (0.5 mL) was added 2.0 M lithium tetrahydroborate in THF (0.12 mL, 0.25 mmol). The reaction mixture was stirred at room temperature overnight. The reaction was quenched with water slowly. The aqueous layer was extracted with ethyl acetate. The organic layer was concentrated. The resulting residue was purified with prep-LCMS (XBridge C18 column, eluting with a gradient of acetonitrile/water containing 0.1% ammonium hydroxide, at flow rate of 60 mL/min) to give the desired product. $^1H$ NMR (400 MHz, $CDCl_3$) δ 7.79-7.68 (m, 2H), 7.61 (s, 1H), 6.65 (m, 1H), 6.20 (m, 1H), 4.99-4.89 (m, 1H), 4.68 (s, 2H), 4.60 (d, J=8.5 Hz, 2H), 4.45 (dd, J=8.9 and 2.0 Hz, 2H), 3.38 (s, 2H), 2.34 (s, 3H), 1.41 (d, J=7.0 Hz, 3H). LCMS calculated for $C_{23}H_{23}F_5N_7O_2$ $(M+H)^+$: m/z=524.2. Found: 524.0.

Example 14

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Procedure 1)

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (24.8 mg, 0.0489 mmol) was added ethanol (0.3 mL) and the mixture was stirred to form a clear solution. Phosphoric acid in isopropanol (0.064 mL, 1 M, 0.064 mmol, 1.3 eq.) was added and the mixture was stirred for 2 minutes to form a slurry. This slurry was then stirred continuously overnight. This mixture was filtered, and the filter cake washed with methyl tert-butyl ether (MTBE). The filter cake was air-dried to afford the title salt (26.3 mg, 88.9%). The X-ray powder diffraction (XRPD) pattern was determined for the phosphoric acid salt and is shown in FIG. 1. A list of 2-theta peaks is provided in Table 2 below.

TABLE 2

| 2-Theta | Height | H % |
|---|---|---|
| 6.848 | 841 | 64.7 |
| 8.225 | 135 | 10.4 |
| 11.778 | 214 | 16.5 |
| 12.854 | 378 | 29.1 |
| 13.577 | 543 | 41.7 |
| 14.741 | 157 | 12.1 |
| 15.967 | 589 | 45.3 |
| 16.557 | 1061 | 81.6 |
| 17.425 | 216 | 16.6 |
| 18.021 | 299 | 23 |
| 19.907 | 1139 | 87.6 |
| 20.791 | 1300 | 100 |
| 21.267 | 248 | 19.1 |
| 22.556 | 168 | 12.9 |
| 23.77 | 949 | 73 |
| 24.667 | 716 | 55.1 |
| 25.698 | 913 | 70.2 |
| 26.159 | 434 | 33.4 |
| 27.392 | 140 | 10.8 |
| 28.647 | 199 | 15.3 |
| 29.667 | 251 | 19.3 |
| 30.411 | 333 | 25.6 |
| 31.213 | 141 | 10.9 |
| 32.115 | 84 | 6.5 |
| 32.893 | 170 | 13.1 |
| 33.572 | 109 | 8.4 |
| 34.449 | 108 | 8.3 |
| 35.264 | 82 | 6.3 |
| 35.741 | 78 | 6 |
| 36.709 | 170 | 13.1 |
| 37.381 | 103 | 7.9 |
| 38.828 | 63 | 4.9 |
| 39.443 | 117 | 9 |
| 40.559 | 88 | 6.8 |
| 41.227 | 88 | 6.8 |
| 43.396 | 61 | 4.7 |
| 44.1 | 90 | 6.9 |

Example 15

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Procedure 2)

Figure 2:
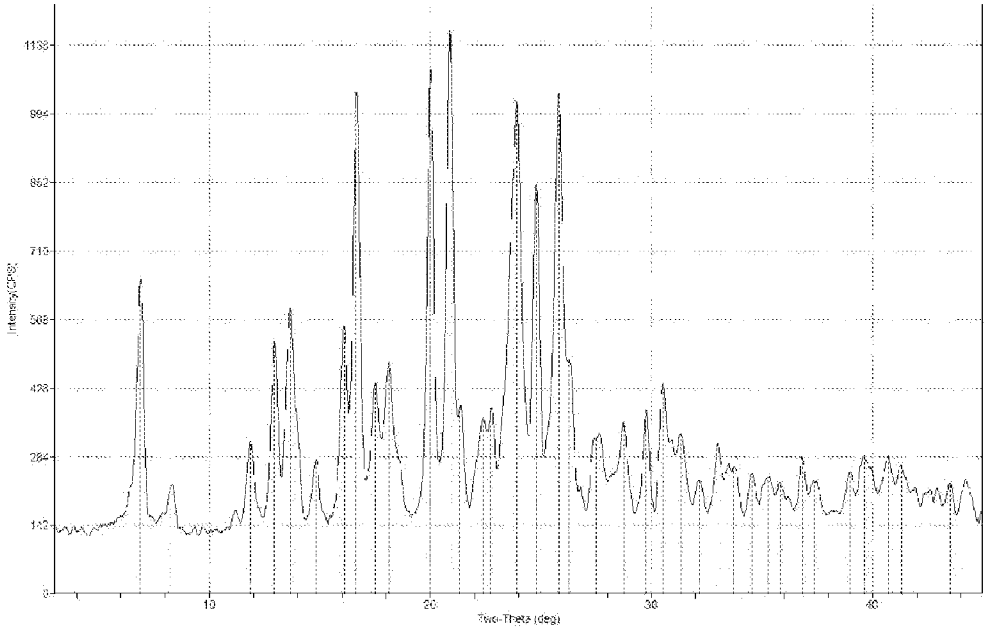
FIG. 2 shows an XRPD pattern characteristic of the salt of Example 15.

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (24.6 mg, 0.0485 mmol) was added acetonitrile (0.3 mL) and the mixture was stirred to form a clear solution. Phosphoric acid in isopropanol (0.063 mL, 1 M, 0.063 mmol, 1.3 eq.) was added and the mixture was stirred for 2 h to form a slurry, which was then stirred continuously overnight. This mixture was filtered, and the filter cake washed with MTBE. The filter cake was air-dried to afford the title salt (26.27 mg, 89.5%). The XRPD pattern was determined for the phosphoric acid salt and is shown in FIG. 2. A list of 2-theta peaks is provided in Table 3 below.

TABLE 3

| 2-Theta | Height | H % |
|---|---|---|
| 6.884 | 499 | 54.1 |
| 8.305 | 90 | 9.7 |
| 11.868 | 165 | 17.9 |
| 12.945 | 302 | 32.8 |
| 13.685 | 411 | 44.6 |
| 14.831 | 125 | 13.6 |
| 16.116 | 368 | 40 |
| 16.656 | 818 | 88.8 |
| 17.528 | 184 | 19.9 |
| 18.135 | 278 | 30.1 |
| 20.003 | 845 | 91.7 |
| 20.898 | 921 | 100 |
| 21.335 | 178 | 19.3 |
| 22.409 | 139 | 15.1 |
| 22.701 | 135 | 14.6 |
| 23.894 | 711 | 77.2 |
| 24.796 | 535 | 58.1 |
| 25.821 | 778 | 84.4 |
| 26.266 | 245 | 26.6 |
| 27.483 | 122 | 13.2 |
| 28.742 | 160 | 17.4 |
| 29.761 | 208 | 22.6 |
| 30.539 | 237 | 25.7 |
| 31.331 | 111 | 12 |
| 32.176 | 55 | 5.9 |
| 33.026 | 134 | 14.5 |
| 33.714 | 88 | 9.5 |
| 34.542 | 69 | 7.5 |
| 35.263 | 60 | 6.5 |
| 35.829 | 48 | 5.3 |
| 36.838 | 108 | 11.8 |
| 37.369 | 64 | 7 |
| 38.956 | 53 | 5.8 |
| 39.631 | 89 | 9.7 |
| 40.7 | 75 | 8.2 |
| 41.298 | 71 | 7.7 |
| 43.504 | 54 | 5.9 |
| 44.228 | 76 | 8.3 |

Example 16

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Procedure 3)

Figure 3:
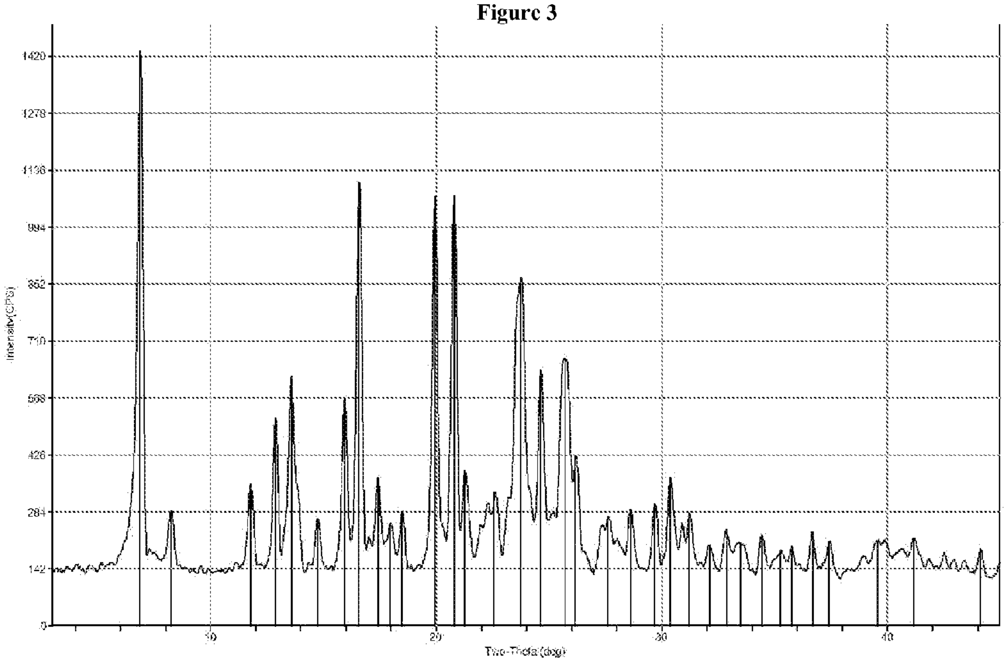
FIG. 3 shows an XRPD pattern characteristic of the salt of Example 16.

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (98.93 mg, 0.195 mmol) was added isopropanol (1.23 mL) and the mixture was stirred to form a clear solution. Phosphoric acid in isopropanol (0.273 mL, 1 M, 0.273 mmol, 1.4 eq.) was added and the mixture stirred for 1 h at 70° C. to form a slurry. This slurry was then cooled to room temperature and stirred overnight. This mixture was filtered, and the filter cake washed with MTBE. The filter cake was air-dried to afford the title salt (109.1 mg, 92.4%). The XRPD pattern was determined for the phosphoric acid salt and is shown in FIG. 3. A list of 2-theta peaks is provided in Table 4 below.

TABLE 4

| 2-Theta | Height | H % |
|---|---|---|
| 6.856 | 1268 | 100 |
| 8.237 | 133 | 10.5 |
| 11.765 | 209 | 16.5 |
| 12.859 | 343 | 27 |
| 13.596 | 472 | 37.2 |
| 14.74 | 127 | 10 |
| 15.931 | 403 | 31.8 |
| 16.569 | 912 | 72 |
| 17.425 | 177 | 13.9 |
| 17.964 | 80 | 6.3 |
| 18.495 | 117 | 9.2 |
| 19.926 | 876 | 69 |
| 20.783 | 865 | 68.2 |
| 21.274 | 197 | 15.6 |
| 22.561 | 152 | 12 |
| 23.727 | 634 | 50 |
| 24.637 | 370 | 29.2 |
| 25.706 | 443 | 35 |
| 26.157 | 290 | 22.9 |
| 27.597 | 117 | 9.3 |
| 28.627 | 120 | 9.5 |
| 29.682 | 151 | 11.9 |
| 30.389 | 186 | 14.6 |
| 31.186 | 103 | 8.1 |
| 32.128 | 55 | 4.3 |
| 32.872 | 98 | 7.7 |
| 33.483 | 72 | 5.7 |
| 34.435 | 87 | 6.8 |
| 35.257 | 42 | 3.3 |
| 35.742 | 56 | 4.4 |
| 36.667 | 95 | 7.5 |
| 37.413 | 84 | 6.7 |
| 39.574 | 56 | 4.4 |
| 41.182 | 60 | 4.8 |
| 44.124 | 64 | 5 |

Example 17

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Procedure 4)

Step 1. 4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (crude)

To a clear solution of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (405.0 g, 798.1 mmol) in methanol (520.0 mL) and isopropanol (2550.0 mL) at 50° C. was added an aqueous solution of 85% phosphoric acid (119.65 g, 1037.8 mmol) in isopropanol (120.0 mL) over 18 minutes to form a slurry. The resulting slurry was stirred at 50° C. for 1 h. n-Heptane (4050.0 mL) was then added to the slurry over 40 min, while maintaining the internal temperature of the slurry between 46 to 53° C. After the addition of n-heptane, the slurry was gradually cooled to room temperature and stirred at room temperature for 19 h. The solids were then collected by filtration, washed with a mixture of isopropanol and n-heptane (3:10 by volume, 2×700 mL) followed by n-heptane (3×550 mL), and dried under vacuum at room temperature to afford crude 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (434.6 g, 89.9% yield).

Step 2. 4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (purified)

Into a 22 L round bottom flask equipped with an overhead stirring mechanism and a Teflon-coated thermocouple was added 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt of Step 1 (958.3 g, 1583 mmol) and methanol (MeOH, 9583.0 mL) at room temperature. The resulting slurry was heated to 50° C. to give a clear, light-orange colored solution. The solution was polish filtered, transferred back to the 22 L flask and heated to reflux to distill methanol (4793 g, 6090 mL) over 70 min. Isopropanol (7700 mL) was then added to the flask over 30 min while maintaining the solution temperature between 50 to 65° C. After complete addition of isopropanol, n-heptane (14400 mL) was added portion-wise while maintaining a gentle distillation of the solvent mixture (MeOH, IPA and n-heptane) over 2.5 h. A total of 10818 g (15000 mL) of the solvent mixture was distilled. The resulting slurry was gradually cooled to room temperature, and stirred at room temperature for 17 h. The solids were collected by filtration, washed with a mixture of isopropanol and n-heptane (1:5 by volume, 3000 mL) followed by n-heptane (3×4000 mL), and dried under vacuum at room temperature to afford the title compound as off-white crystalline powder (925.7 g, 96.6% yield).

The phosphoric acid salt was shown to be a 1:1 salt by $^1$H NMR and crystallinity was confirmed by XRPD. $^1$H NMR (400 MHz, DMSO-$d_6$): δ 9.35 (br. s, 4H), 8.50 (d, J=8.9 Hz, 1H), 8.11 (s, 1H), 7.70 (s, 1H), 7.34 (dd, J=12.5, 6.4 Hz, 1H), 6.61 (dd, J=12.0, 7.4 Hz, 1H), 4.86-4.69 (m, 1H), 4.61 (d, J=8.9 Hz, 2H), 4.38 (d, J=8.9 Hz, 2H), 3.64 (s, 2H), 2.21 (s, 6H), 1.30 (d, J=7.1 Hz, 3H); $^{13}$C NMR (100 MHz, DMSO-$d_6$) δ 162.8, 156.7 (d, $J_{CF}$=246.5 Hz), 146.9 (d, $J_{CF}$=236.1 Hz), 141.6 (dd, $J_{CF}$=13.0, 11.7 Hz), 140.3, 138.3, 125.8 (q, $J_{CF}$=281.8 Hz), 125.6, 117.2, 116.4 (dd, $J_{CF}$=22.3, 4.6 Hz), 115.1, 111.3 (dd, $J_{CF}$=15.7, 5.8 Hz), 107.7, 102.0 (dd, $J_{cF}$=29.5, 4.5 Hz), 62.3, 57.7, 57.7, 45.8 (q, $J_{CF}$=30.5 Hz), 27.0, 13.3 (d, $J_{CF}$=1.7 Hz), 11.7. $C_{23}H_{22}F_5N_7O$ (calc. MW 507.46); LCMS: (EI) m/e 508.1 ($M^+$+H). DSC showed a sharp melting peak at about 227.62° C. (onset at 224.45° C.) as shown in FIG. 4A. The title compound showed a weight loss of 0.129% up to 200° C. as shown in FIG. 4B. The XRPD pattern was determined for the phosphoric acid salt and is shown in FIG. 4C. A list of 2-theta peaks is provided in Table 5 below.

TABLE 5

| 2-Theta | Height | H % |
|---|---|---|
| 6.805 | 8160 | 100 |
| 7.278 | 56 | 0.7 |
| 8.164 | 230 | 2.8 |
| 11.065 | 68 | 0.8 |
| 11.685 | 1060 | 13 |
| 12.798 | 260 | 3.2 |
| 13.512 | 920 | 11.3 |
| 14.667 | 110 | 1.3 |
| 15.923 | 686 | 8.4 |
| 16.49 | 2186 | 26.8 |
| 17.022 | 236 | 2.9 |
| 17.292 | 111 | 1.4 |
| 17.991 | 137 | 1.7 |
| 18.448 | 703 | 8.6 |
| 19.827 | 1407 | 17.2 |
| 20.677 | 2119 | 26 |
| 21.236 | 199 | 2.4 |

TABLE 5-continued

| 2-Theta | Height | H % |
|---|---|---|
| 22.079 | 275 | 3.4 |
| 22.421 | 406 | 5 |
| 23.592 | 2119 | 26 |
| 24.635 | 424 | 5.2 |
| 25.317 | 296 | 3.6 |
| 25.64 | 674 | 8.3 |
| 26.161 | 363 | 4.5 |
| 27.284 | 94 | 1.2 |
| 27.989 | 198 | 2.4 |
| 28.628 | 118 | 1.4 |
| 29.63 | 135 | 1.7 |
| 30.419 | 455 | 5.6 |
| 32.099 | 60 | 0.7 |
| 32.832 | 148 | 1.8 |
| 33.346 | 166 | 2 |
| 34.436 | 447 | 5.5 |
| 35.711 | 117 | 1.4 |
| 36.719 | 295 | 3.6 |
| 37.349 | 135 | 1.7 |
| 38.802 | 53 | 0.6 |
| 39.585 | 108 | 1.3 |
| 40.565 | 64 | 0.8 |
| 41.224 | 260 | 3.2 |
| 42.44 | 68 | 0.8 |

Example 18

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt (Procedure 1)

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (97.64 mg, 0.192 mmol) was added 2-butanol (1.2 mL) and the mixture was stirred for 2 min to afford a clear solution. Hydrochloric acid in isopropanol/isopropylacetate (0.29 mL, 1 M in IPA/IPAc from 3.7 M HCl in IPAc, 0.29 mmol, 1.5 eq.) was added to give a clear solution. This solution was stirred for 6 min to form a slurry. This slurry was then stirred at room temperature for 5 h. The slurry was then filtered and the filter cake was washed with MTBE. The filter cake was dried under vacuum for 12 h at 45-50° C. to afford the title salt (97.8 mg, 93.4%). DSC showed a sharp melting peak at about 213.07° C. (onset at 209.22° C.) as shown in FIG. 5A. The title compound showed a weight loss of 4.635% up to about 210° C. as shown in FIG. 5B. The XRPD pattern was determined for the hydrochloric acid salt and is shown in FIG. 5C. A list of 2-theta peaks is provided in Table 6 below.

TABLE 6

| 2-Theta | Height | H % |
|---|---|---|
| 7.067 | 208 | 38 |
| 12.234 | 289 | 53 |
| 13.716 | 308 | 56.4 |
| 14.48 | 133 | 24.4 |
| 14.784 | 295 | 54 |
| 15.459 | 289 | 52.9 |
| 16.259 | 181 | 33.1 |
| 16.609 | 359 | 65.7 |
| 17.121 | 347 | 63.5 |
| 19.486 | 129 | 23.5 |
| 20.439 | 147 | 27 |
| 21.259 | 95 | 17.4 |
| 22.865 | 223 | 40.8 |
| 23.857 | 335 | 61.3 |

TABLE 6-continued

| 2-Theta | Height | H % |
|---|---|---|
| 24.771 | 546 | 100 |
| 25.704 | 204 | 37.4 |
| 26.496 | 284 | 51.9 |
| 27.429 | 334 | 61.1 |
| 28.354 | 194 | 35.6 |
| 28.71 | 106 | 19.3 |
| 31.472 | 70 | 12.8 |
| 31.84 | 117 | 21.4 |
| 34.09 | 117 | 21.5 |
| 40.551 | 58 | 10.6 |
| 41.48 | 75 | 13.8 |
| 44.075 | 53 | 9.7 |

Example 19

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt (Procedure 2)

Figure 6:
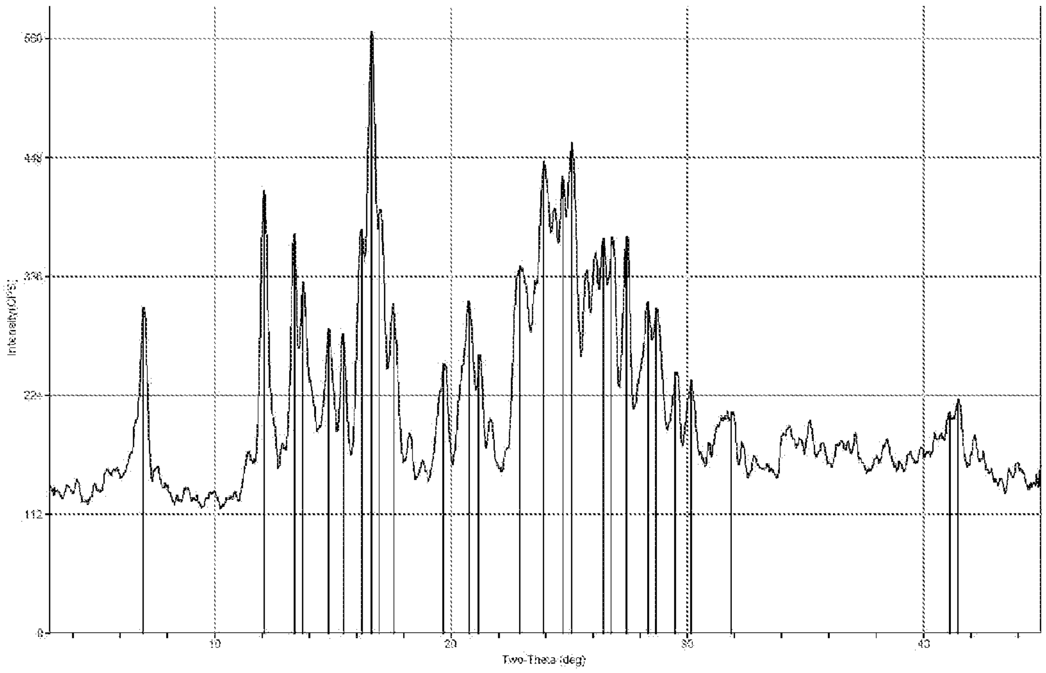
FIG. 6 shows an XRPD pattern characteristic of the salt of Example 19.

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (52.12 mg, 0.103 mmol) was added isopropanol (0.5 mL) and the mixture was stirred for 3 min to form a clear solution. Hydrochloric acid in isopropanol/isopropylacetate (0.144 mL, 1 M in IPA/IPAc from 3.7 M HCl in IPAc, 0.144 mmol, 1.4 eq.) was then added, resulting in a clear solution. This clear solution was stirred for 6-8 minutes to form a slurry. This slurry was then stirred at room temperature for 5 h. The slurry was then filtered and the filter cake was washed with MTBE. The filter cake was air-dried to afford the title salt (51.2 mg, 91.6%). The XRPD pattern was determined for the hydrochloric acid salt and is shown in FIG. 6. A list of 2-theta peaks is provided in Table 7 below.

TABLE 7

| 2-Theta | Height | H % |
|---|---|---|
| 6.967 | 164 | 47.1 |
| 12.082 | 267 | 76.8 |
| 13.388 | 202 | 58 |
| 13.71 | 150 | 43.1 |
| 14.831 | 101 | 29.1 |
| 15.438 | 97 | 27.9 |
| 16.243 | 174 | 50.1 |
| 16.634 | 348 | 100 |
| 16.97 | 189 | 54.2 |
| 17.576 | 76 | 21.8 |
| 19.672 | 96 | 27.5 |
| 20.758 | 141 | 40.6 |
| 21.163 | 94 | 27.1 |
| 22.879 | 110 | 31.7 |
| 23.928 | 115 | 33 |
| 24.735 | 128 | 36.8 |
| 25.097 | 149 | 42.9 |
| 26.444 | 120 | 34.4 |
| 26.767 | 112 | 32.2 |
| 27.416 | 147 | 42.3 |
| 28.344 | 105 | 30.2 |
| 28.686 | 105 | 30.2 |
| 29.508 | 58 | 16.7 |
| 30.156 | 67 | 19.2 |
| 31.853 | 50 | 14.3 |
| 41.126 | 44 | 12.7 |

Example 20

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (54.74 mg, 0.108 mmol) was added isopropanol (0.6 mL) and the mixture was stirred for 3 min to give a clear solution. Hydrobromic acid in isopropanol/water (0.151 mL, 1 M IPA/water from 48% HBr in water, 0.144 mmol, 1.4 eq.) was added, resulting in a clear solution, which was then stirred for about 8 minutes to form a slurry. This slurry was stirred at room temperature for 5 h. The slurry was then filtered and the filter cake was washed with MTBE. The filter cake was air-dried to afford the title salt (53.12 mg, 83.7%). DSC showed a sharp melting peak at about 203.19° C. (onset at 199.26° C.) as shown in FIG. 7A. The title compound showed only slight weight loss up to about 100° C. as shown in FIG. 7B. The XRPD pattern was determined for the hydrobromic acid salt and is shown in FIG. 7C. A list of 2-theta peaks is provided in Table 8 below.

TABLE 8

| 2-Theta | Height | H % |
|---|---|---|
| 7.007 | 254 | 36.6 |
| 12.179 | 139 | 20.1 |
| 12.445 | 116 | 16.8 |
| 13.468 | 86 | 12.4 |
| 14.377 | 297 | 42.9 |
| 15.042 | 65 | 9.4 |
| 15.622 | 192 | 27.6 |
| 16.211 | 140 | 20.1 |
| 17.051 | 281 | 40.5 |
| 17.407 | 87 | 12.5 |
| 18.5 | 62 | 8.9 |
| 19.583 | 121 | 17.5 |
| 20.222 | 308 | 44.4 |
| 21.104 | 347 | 50 |
| 22.821 | 376 | 54.2 |
| 23.484 | 338 | 48.8 |
| 23.663 | 137 | 19.8 |
| 24.279 | 137 | 19.8 |
| 24.889 | 693 | 100 |
| 25.425 | 171 | 24.7 |
| 25.99 | 76 | 11 |
| 26.62 | 203 | 29.3 |
| 27.095 | 330 | 47.6 |
| 27.483 | 116 | 16.7 |
| 28.208 | 382 | 55.1 |
| 28.572 | 159 | 22.9 |
| 29.801 | 134 | 19.3 |
| 30.33 | 89 | 12.8 |
| 31.278 | 160 | 23 |
| 31.971 | 66 | 9.5 |
| 33.731 | 118 | 17.1 |
| 34.608 | 103 | 14.8 |
| 35.638 | 68 | 9.8 |
| 36.746 | 111 | 16 |
| 38.497 | 72 | 10.3 |
| 39.297 | 112 | 16.2 |
| 40.476 | 98 | 14.2 |
| 41.364 | 169 | 24.4 |
| 43.37 | 68 | 9.8 |
| 43.804 | 60 | 8.7 |

Example 21

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt (Procedure 1)

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (47 mg, 0.103 mmol) was added isopropanol (0.5 mL) and the mixture was stirred for 3 min to give a clear solution. Sulfuric acid in isopropanol (0.5 M in IPA from 98% sulfuric acid, 0.051 mmol, 0.55 eq.) was added, resulting in a clear solution, which was then stirred for 6-8 minutes to form a slurry. This slurry was then stirred at room temperature for 5 h. The slurry was then filtered and the filter cake was washed with MTBE. The filter cake was air-dried to afford the title salt (18.84 mg, 33.6%). DSC showed two endotherms at 136.16° C. and 146.97° C. (onset at 122.15° C.) and a sharp endotherm at 259.16° C. (onset at 255.09° C.) as shown in FIG. 8A. The XRPD pattern was determined for the sulfuric acid salt and is shown in FIG. 8B. A list of 2-theta peaks is provided in Table 9 below.

TABLE 9

| 2-Theta | Height | H % |
|---|---|---|
| 3.742 | 151 | 18.4 |
| 7.322 | 228 | 27.7 |
| 9.892 | 93 | 11.3 |
| 12.57 | 74 | 9 |
| 13.642 | 56 | 6.8 |
| 14.713 | 341 | 41.4 |
| 16.307 | 81 | 9.8 |
| 17.412 | 60 | 7.3 |
| 18.978 | 125 | 15.2 |
| 19.628 | 823 | 100 |
| 20.982 | 73 | 8.9 |
| 21.256 | 212 | 25.8 |
| 22.041 | 66 | 8 |
| 24.625 | 691 | 84 |
| 25.902 | 66 | 8 |
| 26.529 | 123 | 15 |
| 27.083 | 174 | 21.1 |
| 28.18 | 175 | 21.2 |
| 30.706 | 91 | 11.1 |
| 32.369 | 53 | 6.4 |
| 34.766 | 96 | 11.6 |
| 38.298 | 50 | 6 |
| 38.663 | 74 | 9 |
| 42.485 | 48 | 5.8 |

Example 22

4-[3-(Cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt (Procedure 2)

Figure 9:
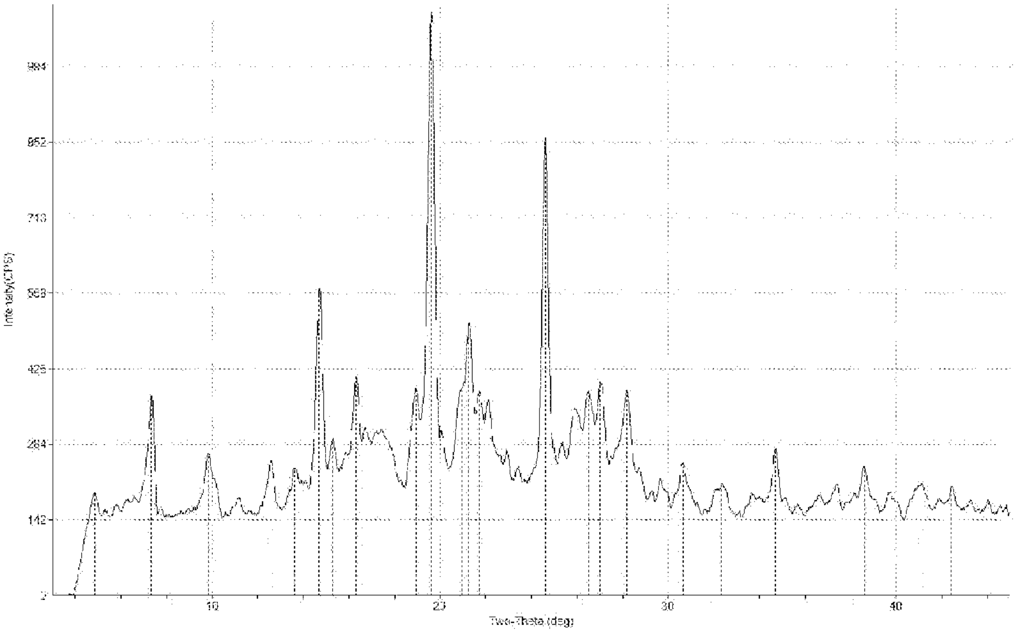
FIG. 9 shows an XRPD pattern characteristic of the salt of Example 22.

To 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (27.91 mg, 0.055 mmol) was added isopropanol (0.5 mL) to form a clear solution. Sulfuric acid in water (1.0 M, 0.06 mmol, 1.09 eq.) was added and the resulting mixture was stirred to form a slurry. This slurry was heated to 60° C. and stirred to yield a clear solution. The solution was cooled to room temperature and stirred continuously overnight. The resulting mixture was filtered and the filter cake was washed with MTBE. The filter cake was then dried to afford the title salt. The XRPD pattern was determined for the sulfuric acid salt and is shown in FIG. 9. A list of 2-theta peaks is provided in Table 10 below.

TABLE 10

| 2-Theta | Height | H % |
|---|---|---|
| 4.843 | 191 | 22.5 |
| 7.313 | 218 | 25.8 |
| 9.856 | 116 | 13.7 |
| 12.556 | 95 | 11.2 |
| 13.61 | 57 | 6.8 |
| 14.703 | 361 | 42.6 |
| 15.261 | 64 | 7.5 |
| 16.309 | 147 | 17.3 |
| 18.941 | 149 | 17.6 |
| 19.611 | 847 | 100 |
| 20.952 | 113 | 13.3 |
| 21.242 | 241 | 28.4 |
| 21.708 | 100 | 11.8 |
| 24.609 | 620 | 73.2 |
| 26.513 | 130 | 15.3 |
| 27.026 | 126 | 14.8 |
| 28.19 | 167 | 19.7 |
| 30.659 | 86 | 10.1 |
| 32.346 | 60 | 7 |
| 34.711 | 108 | 12.7 |
| 38.597 | 82 | 9.7 |
| 41.082 | 55 | 6.4 |
| 42.435 | 43 | 5.1 |

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Table 11 for data related to compounds of the examples.

TABLE 11

$IC_{50}$ data for JAK enzyme assay (at 1 mM ATP)

| Example No. | JAK1 $IC_{50}$ (nM)* | JAK2 $IC_{50}$ (nM)* | JAK2/ JAK1 |
|---|---|---|---|
| 1 | + | ++++ | >10 |
| 2 | + | ++ | >10 |
| 3 | + | +++ | >10 |
| 4 | + | ++ | >10 |
| 5 | ++ | +++ | >10 |
| 6 | + | +++ | >10 |
| 7 | + | ++ | >10 |

TABLE 11-continued $IC_{50}$ data for JAK enzyme assay (at 1 mM ATP)

| Example No. | JAK1 $IC_{50}$ (nM)* | JAK2 $IC_{50}$ (nM)* | JAK2/ JAK1 |
|---|---|---|---|
| 8 | + | ++ | >10 |
| 9 | + | ++ | >10 |
| 10 | ++ | +++ | |
| 11 | ++ | +++ | |
| 12 | ++ | +++ | |
| 13 | + | +++ | >10 |
| 17 | + | ++ | >10 |

*300 nM or less (+); >300 nM to 1000 nM (++); >1000 nM (+++); >700 nM (++++)

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 μg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 200 μL (100 μL on the internal pinna and 100 μL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Example H

S100A9 Transgenic Mouse Model

It was previously shown that S100A9 transgenic mice display bone marrow accumulation of MDSC accompanied by development of progressive multilineage cytopenias and cytological dysplasia similar to MDS. Further, early forced maturation of MDSC by either all-trans-retinoic acid treatment or active immunoreceptor tyrosine-based activation motif-bearing (ITAM-bearing) adapter protein (DAP12) interruption of CD33 signaling rescued the hematologic phenotype and mitigated the disease. This system can be useful to test the effects on JAK1 inhibition on MDS-like disease in a preclinical model. *J. Clin. Invest.,* 123(11):4595-4611 (2013), Accordingly, a JAK1 selective inhibitor is dosed by oral gavage. The compound's ability to reduce the cytopenias and cytological dysplasia observed in the S100A9 transgenic mice is monitored.

Various modifications of the invention, in addition to those described herein, will be apparent to those skilled in the art from the foregoing description. Such modifications are also intended to fall within the scope of the appended claims. Each reference cited in the present application, including all patent, patent applications, and publications, is incorporated herein by reference in its entirety.

What is claimed is:

1. A compound of Formula I:

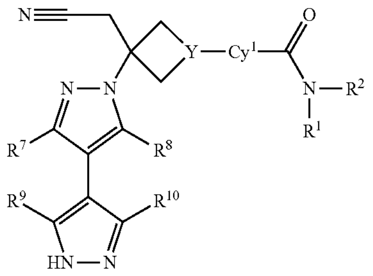

I or a pharmaceutically acceptable salt thereof; wherein:

$Cy^1$ is phenyl, pyridyl, pyrimidinyl, pyrazinyl, or pyridazinyl, each of which is optionally substituted by 1, 2, 3, or 4 groups independently selected from $R^3$, $R^4$, $R^5$, and $R^6$;

Y is N or CH;

$R^1$ is $C_{1-6}$ alkyl, $C_{1-6}$ haloalkyl, $C_{3-7}$ cycloalkyl, $C_{3-7}$ cycloalkyl-$C_{1-3}$ alkyl, 4-7 membered heterocycloalkyl, 4-7 membered heterocycloalkyl-$C_{1-3}$ alkyl, phenyl, phenyl-$C_{1-3}$ alkyl, 5-6 membered heteroaryl or 5-6 membered heteroaryl-$C_{1-3}$ alkyl, each of which is optionally substituted with 1, 2, or 3 substituents independently selected from fluoro, chloro, $C_{1-3}$ alkyl, —OH, —O($C_{1-3}$ alkyl), —CN, —$CF_3$, —$CHF_2$, —$CH_2F$, —$NH_2$, —NH($C_{1-3}$ alkyl), —N($C_{1-3}$ alkyl)$_2$, —C(═O)N($C_{1-3}$ alkyl)$_2$, —C(═O)NH($C_{1-3}$ alkyl), —C(═O)$NH_2$, —C(═O)O($C_{1-3}$ alkyl), —S(═O)$_2$($C_{1-3}$ alkyl), —S(═O)$_2$($C_{3-6}$ cycloalkyl), —C(═O)($C_{3-6}$ cycloalkyl), and —C(═O)($C_{1-3}$ alkyl);

$R^2$ is H or $C_{1-3}$ alkyl; wherein said $C_{1-3}$ alkyl is optionally substituted by 1, 2, or 3 substituents independently selected from fluoro, chloro, —OH, —O($C_{1-3}$ alkyl), —CN, —$CF_3$, —$CHF_2$, —$CH_2F$, $NH_2$, —NH($C_{1-3}$ alkyl), and —N($C_{1-3}$ alkyl)$_2$; or $R^1$ and $R^2$, together with the nitrogen atom to which they are attached, form a 4-, 5- or 6-membered heterocycloalkyl ring, which is optionally substituted with 1, 2, or 3 substitutents independently selected from F, Cl, —OH, —O($C_{1-3}$ alkyl), —CN, $C_{1-3}$ alkyl, $C_{1-3}$ haloalkyl, —$NH_2$, —NH($C_{1-3}$ alkyl), —N($C_{1-3}$ alkyl)$_2$, —$CH_2CN$, and —$CH_2OH$;

$R^3$ is H, F, Cl, —CN, $C_{1-3}$ alkyl, $C_{1-3}$ fluoroalkyl, —O($C_{1-3}$ alkyl), or —O($C_{1-3}$ fluoroalkyl);

$R^4$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^5$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^6$ is H, F, Cl, —CN, $C_{1-3}$ alkyl, $C_{1-3}$ fluoroalkyl, —O($C_{1-3}$ alkyl), or —OC($C_{1-3}$ fluoroalkyl);

$R^7$ is H, F, Cl, $C_{1-3}$ alkyl, $C_{1-3}$ haloalkyl, —$NR^{17}R^{17a}$, —NHC(═O)$R^{17b}$, —C(═O)$NR^{17a}R^{17b}$, —NHS(═O)$_2R^{17b}$, or —S(═O)$_2NR^{17a}R^{17b}$, wherein said $C_{1-3}$ alkyl is optionally substituted with 1, 2, or 3 substituents selected from F, Cl, —CN, —$CF_3$, —$CHF_2$, —$CH_2F$, —$NH_2$, —NH($CH_3$), —N($CH_3$)$_2$, OH, —$OCH_3$, —$OCF_3$, —$OCHF_2$, and —$OCH_2F$;

$R^8$ is H, F, Cl, $C_{1-3}$ alkyl, or $C_{1-3}$ haloalkyl;

$R^9$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{10}$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{17}$ is $C_{1-6}$ alkyl, phenyl or 5-6 membered heteroaryl, each of which is optionally substituted with 1, 2, 3 or 4 independently selected $R^{27}$ substituents;

$R^{17a}$ is H or alkyl;

$R^{17b}$ is $C_{1-3}$ alkyl optionally substituted with 1, 2, or 3 substituents selected from F, chloro, —CN, —$CF_3$, —$CHF_2$, —$CH_2F$, —$NH_2$, —NH($CH_3$), —N($CH_3$)$_2$, OH, —$OCH_3$, and —$OCF_3$, —$OCHF_2$, and —$OCH_2F$; and each $R^{27}$ is independently selected from halo, —OH, $NO_2$, —CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $CF_3$—$C_{1-3}$ hydroxyalkyl, $C_{1-3}$ alkoxy-$C_{1-3}$ alkyl, $C_{3-7}$ cycloalkyl, $C_{1-3}$ alkoxy, $C_{1-3}$ haloalkoxy, $H_2N$—, ($C_{1-3}$ alkyl)NH—, ($C_{1-3}$ alkyl)$_2$N—, HS—, $C_{1-3}$ alkyl-S—, $C_{1-3}$ alkyl-S(═O)—, $C_{1-3}$ alkyl-S(═O)$_2$—, carbamyl, $C_{1-3}$ alkyl-carbamyl, di($C_{1-3}$ alkyl)carbamyl, carboxy, $C_{1-3}$ alkyl-C(═O)—, $C_{1-4}$ alkoxy-C(═O)—, $C_{1-3}$ alkyl-C(═O)O—, $C_{1-3}$ alkyl-C(═O)NH—, $C_{1-3}$ alkyl-S(═O)$_2$NH—, $H_2N$—$SO_2$—, $C_{1-3}$ alkyl-NH—S(═O)$_2$—, ($C_{1-3}$ alkyl)$_2$N—S(═O)$_2$—, $H_2N$—S(═O)$_2$NH—, $C_{1-3}$ alkyl-NHS(═O)$_2$NH—, ($C_{1-3}$ alkyl)$_2$N—S(═O)$_2$NH—, $H_2N$—C(═O)NH—, $C_{1-3}$ alkyl-NHC(═O)NH—, and ($C_{1-3}$ alkyl)$_2$N—C(═O)NH—.

2. The compound of claim 1, having Formula Ia:

Ia

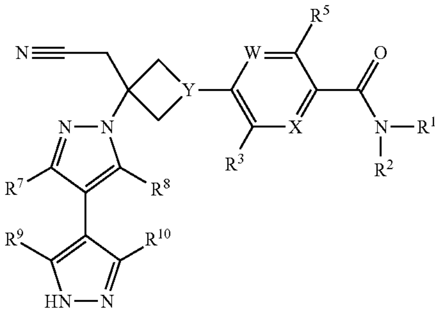

or a pharmaceutically acceptable salt thereof.

3. The compound of claim 1, having Formula Ia:

Ia

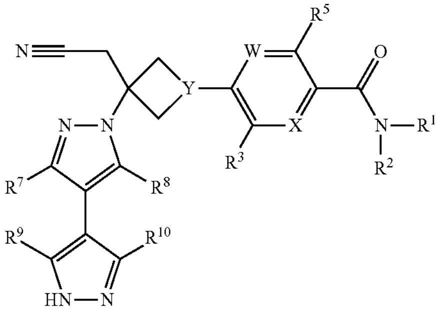

or a pharmaceutically acceptable salt thereof; wherein:

X is N or $CR^4$;

W is N or $CR^6$;

Y is N or CH;

$R^1$ is $C_{1-6}$ alkyl, $C_{1-6}$ haloalkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl, each of which is optionally substituted with 1, 2, or 3 substituents independently selected from fluoro, chloro, $C_{1-3}$ alkyl, —OH, —O($C_{1-3}$ alkyl), —CN, —$CF_3$, —$CHF_2$, —$CH_2F$, —$NH_2$, —NH($C_{1-3}$ alkyl), —N($C_{1-3}$ alkyl)$_2$, —C(═O)N($C_{1-3}$ alkyl)$_2$, —C(═O)NH($C_{1-3}$ alkyl), —C(═O)$NH_2$, —C(═O)O($C_{1-3}$ alkyl), —S(═O)$_2$($C_{1-3}$ alkyl), —S(═O)$_2$($C_{3-6}$ cycloalkyl), —C(═O)($C_{3-6}$ cycloalkyl), and —C(═O)($C_{1-3}$ alkyl);

$R^2$ is H or $C_{1-3}$ alkyl; wherein said $C_{1-3}$ alkyl is optionally substituted by 1, 2, or 3 substituents independently selected from fluoro, chloro, —OH, —O($C_{1-3}$ alkyl), —CN, —$CF_3$, —$CHF_2$, —$CH_2F$, $NH_2$, —NH($C_{1-3}$ alkyl), and —N($C_{1-3}$ alkyl)$_2$; or $R^1$ and $R^2$, together with the nitrogen atom to which they are attached, form a 4-, 5- or 6-membered heterocycloalkyl ring, which is optionally substituted with 1, 2, or 3 substitutents independently selected from fluoro, —OH, —O($C_{1-3}$ alkyl), —CN, $C_{1-3}$ alkyl, $C_{1-3}$ haloalkyl, —$NH_2$, —NH($C_{1-3}$ alkyl), —N($C_{1-3}$ alkyl)$_2$, and —$CH_2CN$;

$R^3$ is H, F, Cl, —CN, $C_{1-3}$ alkyl, —$OCF_3$, —$CF_3$, or —O($C_{1-3}$ alkyl);

$R^4$ is H, F, Cl, —CN, $C_{1-3}$ alkyl, or —O($C_{1-3}$ alkyl);

$R^5$ is H, F, Cl, —CN, $C_{1-3}$ alkyl, or —O($C_{1-3}$ alkyl);

$R^6$ is H, F, CL, —CN, or $C_{1-3}$ alkyl;

$R^7$ is H, F, Cl, $C_{1-3}$ alkyl, $C_{1-3}$ haloalkyl, —$NR^{17}R^{17a}$, —NHC(═O)$R^{17b}$, —C(═O)$NR^{17a}R^{17b}$, —NHS(═O)$_2R^{17b}$, or—S(═O)$_2NR^{17a}R^{17b}$, wherein said $C_{1-3}$ alkyl is optionally substituted with 1, 2, or 3 substituents selected from F, Cl, —CN, —$CF_3$, —$CHF_2$, —$CH_2F$, —$NH_2$, and OH;

$R^8$ is H, F, Cl, $C_{1-3}$ alkyl, or $C_{1-3}$ haloalkyl;

$R^9$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{10}$ is H, F, Cl, $C_{1-3}$ alkyl, $C_{1-3}$ haloalkyl, cyclopropyl, —CN, —$NH_2$, —NH($C_{1-3}$ alkyl), or —N($C_{1-3}$ alkyl)$_2$, wherein said $C_{1-3}$ alkyl is optionally substituted with 1, 2, or 3 substituents selected from F, chloro, —CN, —$CF_3$, —$CHF_2$, —$CH_2F$, —$NH_2$, and OH;

$R^{17}$ is $C_{1-6}$ alkyl, phenyl or 5-6 membered heteroaryl, each of which is optionally substituted with 1, 2, 3 or 4 substituents independently selected from $R^{27}$;

$R^{17a}$ is H or alkyl;

$R^{17b}$ is $C_{1-3}$ alkyl optionally substituted with 1, 2, or 3 substituents selected from F, chloro, —CN, —$CF_3$, —$CHF_2$, —$CH_2F$, —$NH_2$, and OH and each $R^{27}$ is independently selected from halo, —OH, $NO_2$, —CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $CF_3$—$C_{1-3}$ hydroxyalkyl, $C_{1-3}$ alkoxy-$C_{1-3}$ alkyl, $C_{3-7}$ cycloalkyl, $C_{1-3}$ alkoxy, $C_{1-3}$ haloalkoxy, $H_2N$—, ($C_{1-3}$ alkyl)NH—, ($C_{1-3}$ alkyl)$_2$N—, HS—, $C_{1-3}$ alkyl-S—, $C_{1-3}$ alkyl-S(═O)—, $C_{1-3}$ alkyl-S(═O)$_2$—, carbamyl, $C_{1-3}$ alkylcarbamyl, di($C_{1-3}$ alkyl)carbamyl, carboxy, $C_{1-3}$ alkyl-C(═O)—, $C_{1-4}$ alkoxy-C(═O)—, $C_{1-3}$ alkyl-C(═O)O—, $C_{1-3}$ alkyl-C(═O)NH—, $C_{1-3}$ alkyl-S(═O)$_2$NH—, $H_2N$—$SO_2$—, $C_{1-3}$ alkyl-NH—S(═O)$_2$—, ($C_{1-3}$ alkyl)$_2$N—S(═O)$_2$—, $H_2N$—S(═O)$_2$NH—, $C_{1-3}$ alkyl-NHS(═O)$_2$NH—, ($C_{1-3}$ alkyl)$_2$N—S(═O)$_2$NH—, $H_2N$—C(═O)NH—, $C_{1-3}$ alkyl-NHC(═O)NH—, and ($C_{1-3}$ alkyl)$_2$N—C(═O)NH—.

4. The compound of claim 3, or a pharmaceutically acceptable salt thereof, wherein:

$R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^2$ is H or methyl;

$R^3$ is H, F, or Cl;

$R^4$ is H or F;

$R^5$ is H or F;

$R^6$ is H or F;

$R^7$ is H, methyl, ethyl or HO—$CH_2$—;

$R^8$ is H or methyl;

$R^9$ is H, methyl or ethyl; and $R^{10}$ is H, methyl, ethyl or HO—$CH_2$—.

5. The compound of claim 1, or a pharmaceutically acceptable salt thereof, wherein Y is N.

6. The compound of claim 1, or a pharmaceutically acceptable salt thereof, wherein Y is CH.

7. The compound of claim 1, or a pharmaceutically acceptable salt thereof, wherein X is N.

8. The compound of claim 1, or a pharmaceutically acceptable salt thereof, wherein X is $CR^4$.

9. The compound of claim 8, or a pharmaceutically acceptable salt thereof, wherein $R^4$ is H or F.

10. The compound of claim 1, or a pharmaceutically acceptable salt thereof, wherein $R^1$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl.

11. The compound of claim 1, or a pharmaceutically acceptable salt thereof, wherein $R^1$ is isopropyl, ethyl, 1-methylpropyl, 2,2,2-trifluoro-1-methylethyl, 1-cyclopropylethyl, cyclopropyl, 1-trifluoromethylcyclopropyl, 1-cyclopropyl-2,2,2-trifluoroethyl, 2,2,2-trifluoroethyl, or 2,2-difluoroethyl.

12. The compound of claim 1, or a pharmaceutically acceptable salt thereof, wherein having Formula II:

II

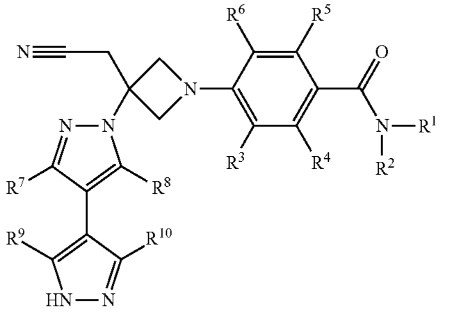

or a pharmaceutically acceptable salt thereof.

13. The compound of claim 1, or a pharmaceutically acceptable salt thereof, wherein having Formula III:

III

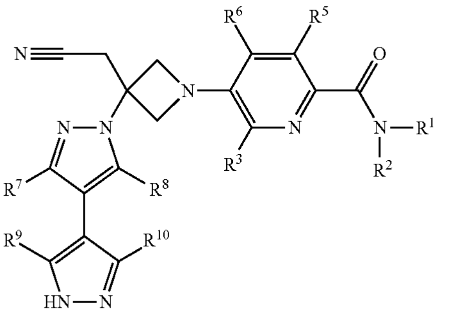

or a pharmaceutically acceptable salt thereof.

14. The compound of claim 1, or a pharmaceutically acceptable salt thereof, wherein, having Formula IV:

IV

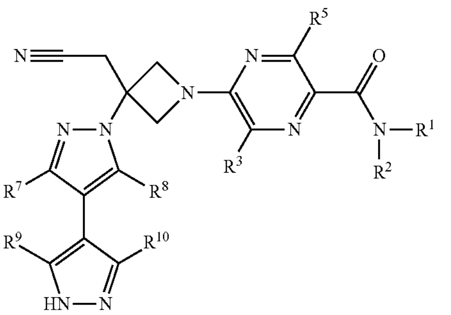

or a pharmaceutically acceptable salt thereof.

15. The compound of claim 1, or a pharmaceutically acceptable salt thereof, wherein, having Formula IIa:

IIa

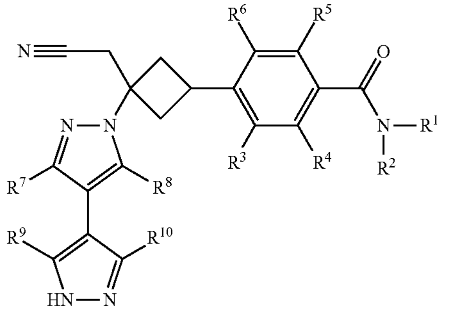

or a pharmaceutically acceptable salt thereof.

16. The compound of claim 1, or a pharmaceutically acceptable salt thereof, wherein, having Formula IIIa:

IIIa

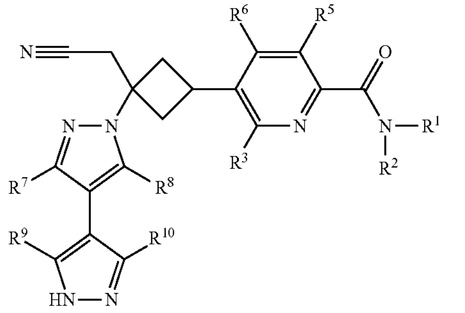

or a pharmaceutically acceptable salt thereof.

17. The compound of claim 1, or a pharmaceutically acceptable salt thereof, wherein, having Formula IVa:

IVa

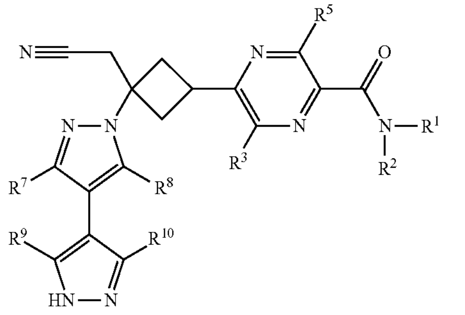

or a pharmaceutically acceptable salt thereof.

18. The compound of claim 1 selected from:

5-[3-(cyanomethyl)-3-(3'-methyl-1H,1'H-4,4'-bipyrazol-1-yl)azetidin-1-yl]-N-[(1S)-2,2,2-trifluoro-1-methylethyl]pyrazine-2-carboxamide;

5-[3-(cyanomethyl)-3-(3'-methyl-1H,1'H-4,4'-bipyrazol-1-yl)azetidin-1-yl]-N-isopropylpyrazine-2-carboxamide;

4-[3-(cyanomethyl)-3-(3'-methyl-1H,1'H-4,4'-bipyrazol-1-yl)azetidin-1-yl]-N-isopropylbenzamide;

4-[3-(cyanomethyl)-3-(3'-methyl-1H,1'H-4,4'-bipyrazol-1-yl)azetidin-1-yl]-2,5-difluoro-N-[(1S)-2,2,2-trifluoro-1-methylethyl]benzamide;

4-[3-(1H,1'H-4,4'-Bipyrazol-1-yl)-3-(cyanomethyl)azetidin-1-yl]-2,5-difluoro-N-[(1S)-2,2,2-trifluoro-1-methylethyl]benzamide;

5-[3-(cyanomethyl)-3-(3,3'-dimethyl-1H,1'H-4,4'-bipyrazol-1-yl)azetidin-1-yl]-N-isopropylpyrazine-2-carboxamide;

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide;

5-[3-(cyanomethyl)-3-(3',5'-dimethyl-1H,1'H-4,4'-bipyrazol-1-yl)azetidin-1-yl]-N-isopropylpyrazine-2-carboxamide;

5-[3-(cyanomethyl)-3-(3',5'-dimethyl-1H,1'H-4,4'-bipyrazol-1-yl)azetidin-1-yl]-N-[(1S)-2,2,2-trifluoro-1-methylethyl]pyrazine-2-carboxamide;

5-[3-(cyanomethyl)-3-(3-methyl-1H,1'H-4,4'-bipyrazol-1-yl)azetidin-1-yl]-N-isopropylpyrazine-2-carboxamide;

5-[3-(cyanomethyl)-3-(3'-ethyl-1H,1'H-4,4'-bipyrazol-1-yl)azetidin-1-yl]-N-[(1S)-2,2,2-trifluoro-1-methylethyl]pyrazine-2-carboxamide;

4-{3-(cyanomethyl)-3-[3'-(hydroxymethyl)-1H,1'H-4,4'-bipyrazol-1-yl]azetidin-1-yl}-2, 5-difluoro-N-[(1S)-2,2,2-trifluoro-1-methylethyl]benzamide;

4-{3-(cyanomethyl)-3-[3-(hydroxymethyl)-3'-methyl-1H,1'H-4,4'-bipyrazol-1-yl]azetidin-1-yl}-2,5-difluoro-N-[(1S)-2,2,2-trifluoro-1-methylethyl]benzamide;

or a pharmaceutically acceptable salt thereof.

19. A composition comprising a compound or salt according to claim 1 and a pharmaceutically acceptable carrier.

20. A method of inhibiting an activity of JAK1 comprising contacting JAK1 with a compound or salt according to claim 1.

21. A method according to claim 20, wherein said compound or salt is selective for JAK1 over JAK2.

22. A method of treating a cancer selected from breast cancer, prostate cancer, lung cancer, renal cancer, colorectal cancer, and pancreatic cancer in a patient in need thereof, comprising administering to said patient a therapeutically effective amount of a compound or salt according to claim 1.

23. The method of claim 22, wherein the cancer is breast cancer.

24. The method of claim 22, wherein the cancer is prostate cancer.

25. The method of claim 22, wherein the cancer is lung cancer.

26. The method of claim 22, wherein the cancer is renal cancer.

27. The method of claim 22, wherein the cancer is colorectal cancer.

28. The method of claim 22, wherein the cancer is pancreatic cancer.

29. The compound of claim 1, which is 5-[3-(cyanomethyl)-3-(3',5'-dimethyl-1H,1'H-4,4'-bipyrazol-1-yl)azetidin-1-yl]-N-[(1S)-2,2,2-trifluoro-1-methylethyl]pyrazine-2-carboxamide, or a pharmaceutically acceptable salt thereof.

30. A method of treating a cancer selected from breast cancer, prostate cancer, lung cancer, renal cancer, colorectal cancer, and pancreatic cancer in a patient in need thereof, comprising administering to said patient a therapeutically effective amount of a compound or salt according to claim 29.

* * * * *